(12) United States Patent
Mirkin et al.

(10) Patent No.: US 9,376,690 B2
(45) Date of Patent: Jun. 28, 2016

(54) TEMPLATED NANOCONJUGATES

(75) Inventors: Chad A. Mirkin, Wilmette, IL (US); David A. Giljohann, Chicago, IL (US); Weston L. Daniel, Evanston, IL (US); Joshua I. Cutler, Evanston, IL (US); Ke Zhang, Chicago, IL (US); Dan Zheng, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 13/504,842

(22) PCT Filed: Nov. 1, 2010

(86) PCT No.: PCT/US2010/055018
§ 371 (c)(1),
(2), (4) Date: Jul. 23, 2012

(87) PCT Pub. No.: WO2011/053940
PCT Pub. Date: May 5, 2011

(65) Prior Publication Data
US 2012/0282186 A1 Nov. 8, 2012

Related U.S. Application Data

(60) Provisional application No. 61/256,640, filed on Oct. 30, 2009, provisional application No. 61/374,550, filed on Aug. 17, 2010, provisional application No. 61/386,846, filed on Sep. 27, 2010.

(51) Int. Cl.
*A61K 9/14* (2006.01)
*C12N 15/88* (2006.01)
(Continued)

(52) U.S. Cl.
CPC .......... *C12N 15/88* (2013.01); *A61K 47/48861* (2013.01); *A61K 49/0002* (2013.01); *B82Y 5/00* (2013.01); *B82Y 15/00* (2013.01); *G01N 33/588* (2013.01)

(58) Field of Classification Search
CPC ..................................................... A61K 9/1694
USPC ........................................................ 424/489
See application file for complete search history.

(56) References Cited

U.S. PATENT DOCUMENTS 3,687,808 A 8/1972 Merigan et al.
4,179,337 A 12/1979 Davis et al.
(Continued)

FOREIGN PATENT DOCUMENTS

EP 1072679 1/2001
EP 1674128 6/2006
(Continued)

OTHER PUBLICATIONS

Abou-Alfa et al., Randomized phase III study of exatecan and gemcitabine compared with gemcitabine alone in untreated advanced pancreatic cancer, J. Clin. Oncol., 24(27):4441-7 (2006).
(Continued)

*Primary Examiner* — Benjamin Packard
(74) *Attorney, Agent, or Firm* — Marshall, Gerstein & Borun LLP

(57) ABSTRACT

The present disclosure is directed to compositions comprising templated nanoconjugates and methods of their use.

45 Claims, 21 Drawing Sheets

(51) Int. Cl.
   *A61K 47/48*     (2006.01)
   *A61K 49/00*     (2006.01)
   *B82Y 5/00*      (2011.01)
   *B82Y 15/00*     (2011.01)
   *G01N 33/58*     (2006.01)

(56) References Cited

U.S. PATENT DOCUMENTS

| | | |
|---|---|---|
| 4,289,872 A | 9/1981 | Denkewalter et al. |
| 4,301,144 A | 11/1981 | Iwashita et al. |
| 4,469,863 A | 9/1984 | Ts'o et al. |
| 4,476,301 A | 10/1984 | Imbach et al. |
| 4,489,055 A | 12/1984 | Couvreur et al. |
| 4,496,689 A | 1/1985 | Mitra |
| 4,587,044 A | 5/1986 | Miller et al. |
| 4,605,735 A | 8/1986 | Miyoshi et al. |
| 4,640,835 A | 2/1987 | Shimizu et al. |
| 4,667,025 A | 5/1987 | Miyoshi et al. |
| 4,670,417 A | 6/1987 | Iwasaki et al. |
| 4,762,779 A | 8/1988 | Snitman |
| 4,789,737 A | 12/1988 | Miyoshi et al. |
| 4,791,192 A | 12/1988 | Nakagawa et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,229,490 A | 7/1993 | Tam |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,270,163 A | 12/1993 | Gold et al. |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,272 A | 10/1995 | Hooykaas |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,547,842 A | 8/1996 | Hogan et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |

(56) References Cited

U.S. PATENT DOCUMENTS

| | | |
|---|---|---|
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,287,860 B1 | 9/2001 | Monia et al. |
| 6,361,944 B1 | 3/2002 | Mirkin et al. |
| 6,403,312 B1 | 6/2002 | Dahiyat et al. |
| 6,417,340 B1 | 7/2002 | Mirkin et al. |
| 6,495,324 B1 | 12/2002 | Mirkin et al. |
| 6,506,564 B1 | 1/2003 | Mirkin et al. |
| 6,544,776 B1 | 4/2003 | Gold et al. |
| 6,582,921 B2 | 6/2003 | Mirkin et al. |
| 6,602,669 B2 | 8/2003 | Letsinger et al. |
| 6,610,491 B2 | 8/2003 | Mirkin et al. |
| 6,656,730 B1 | 12/2003 | Manoharan |
| 6,677,122 B2 | 1/2004 | Mirkin et al. |
| 6,677,153 B2 | 1/2004 | Iversen |
| 6,678,548 B1 | 1/2004 | Echauz et al. |
| 6,682,895 B2 | 1/2004 | Mirkin et al. |
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,812,334 B1 | 11/2004 | Mirkin et al. |
| 6,818,753 B2 | 11/2004 | Mirkin et al. |
| 6,827,979 B2 | 12/2004 | Mirkin et al. |
| 6,828,432 B2 | 12/2004 | Mirkin et al. |
| 6,844,161 B2 | 1/2005 | Siani et al. |
| 6,861,221 B2 | 3/2005 | Mirkin et al. |
| 6,878,814 B2 | 4/2005 | Mirkin et al. |
| 6,974,669 B2 | 12/2005 | Mirkin et al. |
| 6,991,900 B2 | 1/2006 | Shizuya |
| 7,098,320 B1 | 8/2006 | Mirkin et al. |
| 7,223,833 B1 | 5/2007 | Nielsen et al. |
| 7,238,472 B2 | 7/2007 | Mirkin et al. |
| 7,323,309 B2 | 1/2008 | Mirkin et al. |
| 7,332,586 B2 | 2/2008 | Franzen et al. |
| 7,611,728 B2 | 11/2009 | Kidane et al. |
| 7,638,557 B2 | 12/2009 | Lipkin et al. |
| 7,667,004 B2 | 2/2010 | Zhong et al. |
| 7,727,969 B2 | 6/2010 | Farokhzad et al. |
| 2002/0172953 A1 | 11/2002 | Mirkin et al. |
| 2003/0147966 A1 | 8/2003 | Franzen et al. |
| 2003/0181412 A1 | 9/2003 | Erikson |
| 2004/0219565 A1 | 11/2004 | Kauppinen et al. |
| 2004/0247680 A1 | 12/2004 | Farokhzad et al. |
| 2004/0248099 A1 | 12/2004 | Goppelt et al. |
| 2005/0059016 A1 | 3/2005 | Ecker et al. |
| 2005/0074753 A1 | 4/2005 | Goldsborough |
| 2005/0096263 A1 | 5/2005 | Keay et al. |
| 2005/0136258 A1 | 6/2005 | Nie et al. |
| 2005/0197315 A1 | 9/2005 | Taira et al. |
| 2005/0214782 A1 | 9/2005 | Chen et al. |
| 2005/0244858 A1 | 11/2005 | Rossi et al. |
| 2006/0008907 A1 | 1/2006 | Friedman et al. |
| 2006/0019917 A1 | 1/2006 | Guerciolini et al. |
| 2006/0025363 A1 | 2/2006 | Breitenbach et al. |
| 2006/0035344 A1 | 2/2006 | Pachuk et al. |
| 2006/0105343 A1 | 5/2006 | Zetter et al. |
| 2006/0159619 A1* | 7/2006 | Becker et al. ............... 424/1.69 |
| 2006/0159921 A1 | 7/2006 | Murthy et al. |
| 2006/0183247 A1 | 8/2006 | Kim et al. |
| 2006/0188560 A1 | 8/2006 | Cheresh et al. |
| 2006/0233712 A1 | 10/2006 | Penades et al. |
| 2006/0252037 A1 | 11/2006 | Kolesnick et al. |
| 2006/0275371 A1 | 12/2006 | Dai et al. |
| 2007/0105139 A1 | 5/2007 | Nishigaki et al. |
| 2008/0057128 A1 | 3/2008 | Li et al. |
| 2008/0194463 A1 | 8/2008 | Weller et al. |
| 2008/0213177 A1 | 9/2008 | Rademacher et al. |
| 2008/0220072 A1 | 9/2008 | Unger et al. |
| 2008/0279946 A1 | 11/2008 | Hainfeld |
| 2008/0305106 A1 | 12/2008 | Brennan et al. |
| 2008/0306016 A1 | 12/2008 | Mirkin et al. |
| 2008/0317749 A1 | 12/2008 | Kastelein et al. |
| 2008/0317768 A1 | 12/2008 | Bianchi |
| 2009/0035576 A1 | 2/2009 | Prasad et al. |
| 2009/0081244 A1 | 3/2009 | Glenn et al. |
| 2009/0148384 A1 | 6/2009 | Fischer et al. |
| 2009/0148535 A1 | 6/2009 | Bamdad |
| 2009/0155173 A1 | 6/2009 | Scherman et al. |
| 2009/0209629 A1 | 8/2009 | Mirkin et al. |
| 2009/0286853 A1 | 11/2009 | Gryaznov et al. |
| 2010/0167051 A1 | 7/2010 | Goja et al. |
| 2010/0183504 A1 | 7/2010 | Chen |
| 2010/0183634 A1 | 7/2010 | Luo et al. |
| 2010/0291707 A1 | 11/2010 | Mirkin et al. |
| 2011/0172404 A1 | 7/2011 | Luo et al. |
| 2011/0262976 A1 | 10/2011 | Kandula et al. |

FOREIGN PATENT DOCUMENTS

| | | |
|---|---|---|
| JP | 2003-327641 A | 11/2003 |
| WO | WO-89/02439 | 3/1989 |
| WO | WO-93/07883 | 4/1993 |
| WO | WO-93/21259 | 10/1993 |
| WO | WO-95/06731 | 3/1995 |
| WO | WO-95/11910 | 5/1995 |
| WO | WO-97/12896 | 4/1997 |
| WO | WO-98/04740 | 2/1998 |
| WO | WO-98/39352 | 9/1998 |
| WO | WO-98/47343 | 10/1998 |
| WO | WO-99/11655 | 3/1999 |
| WO | WO-99/14226 | 3/1999 |
| WO | WO-00/43045 | 7/2000 |
| WO | WO-01/00876 | 1/2001 |
| WO | WO-01/49869 | 7/2001 |
| WO | WO-01/51665 | 7/2001 |
| WO | WO-01/73123 | 10/2001 |
| WO | WO-02/44321 | 6/2002 |
| WO | WO-02/096262 | 12/2002 |
| WO | WO-03/008539 | 1/2003 |
| WO | WO-03/051278 | 6/2003 |
| WO | WO-03/057175 | 7/2003 |
| WO | WO-2005/099889 A1 | 10/2005 |
| WO | WO-2005/116226 | 12/2005 |
| WO | WO-2006/012695 | 2/2006 |
| WO | WO-2006/045541 | 5/2006 |
| WO | WO-2006/064451 A2 | 6/2006 |
| WO | WO-2006/064453 A2 | 6/2006 |
| WO | WO-2006/138145 A1 | 12/2006 |
| WO | WO-2007/047455 A2 | 4/2007 |

(56) References Cited

FOREIGN PATENT DOCUMENTS

| WO | WO-2008/098248 A2 | 8/2008 |
|----|-------------------|--------|
| WO | WO-2008/141289 A1 | 11/2008 |
| WO | WO-2008/151049 A2 | 12/2008 |
| WO | WO-2009/115579 A1 | 9/2009 |
| WO | WO-2010/060110 A1 | 5/2010 |
| WO | WO-2010/081049 A1 | 7/2010 |
| WO | WO-2010/120420 A1 | 10/2010 |
| WO | WO-2011/017690 A2 | 2/2011 |

OTHER PUBLICATIONS

Agasti et al., Photoregulated release of caged anticancer drugs from gold nanoparticles, J. Am. Chem. Soc., 131(16):5728-9 (2009).

Agrawal et al., Antisence therapeutics: Is it as simple as complementary base recognition? Mol. Med. Today, 6: 72-81 (2000).

Ahmadi et al., Shape-controlled synthesis of colloidal platinum nanoparticles. Science, 272(5270): 1924-6 (1996).

Aime et al., Insights into the use of paramagnetic Gd(III) complexes in MR-molecular imaging investigations, J. Magn. Reson. Imaging, 16(4):394-406 (2002).

Aime et al., Pushing the sensitivity envelope of lanthanide-based magnetic resonance imaging (MRI) contrast agents for molecular imaging applications, Acc. Chem. Res., 42(7):822-31 (2009).

Alivisatos, The use of nanocrystals in biological detection, Nat. Biotechnol., 22(1):47-52 (2004).

Allara et al., Spontaneously organized molecular assemblies. 1. Formation, dynamics, and physical properties of n-Alkanoic acids adsorbed from solution on an oxidized aluminum surface, Langmuir, 1:45-52 (1985).

Allara et al., The study of the gas-solid interaction of acetic acid with a cuprous oxide surface using reflection-absorption spectroscopy, J. Colloid Interface Sci., 49:410-21 (1974).

Alric et al., Gadolinium chelate coated gold nanoparticles as contrast agents for both X-ray computed tomography and magnetic resonance imaging, J. Am. Chem. Soc., 130(18):5908-15 (2008).

Altieri, Survivin, versatile modulation of cell division and apoptosis in cancer, Oncogene, 22: 8581-9 (2003).

Altschul et al., Basic local alignment search tool, J. Mol. Biol., 215(3):403-10 (1990).

Amirkhanov et al., Design of (Gd-D03A)n-polydiamidopropanoyl-peptide nucleic acid-D(Cys-Ser-Lys-Cys) magnetic resonance contrast agents, Biopolymers, 89(12):1061-76 (2008).

Angelini et al., Reversal of P-glycoprotein-mediated multidrug resistance in human sarcoma MES-SA/Dx-5 cells by nonsteroidal anti-inflammatory drugs, Oncol. Rep., 20(4):731-5 (2008).

Aynie, et al., Spongelike alginate nanoparticles as a new potential system for the delivery of antisense oligonucleotides. Antisense Nucl. Acid Drug Dev., 9: 301-12 (1999).

Bahnemann, Photochemical Conversion and Storage of Solar Energy, Pelizetti and Schiavello (Eds.) pp. 251-276 (1991).

Baker et al., Dendrimer-mediated cell transfection in vitro. Meth. Molec. Biol., 245: 67-81 (2004).

Balasubramanian et al., Biodistribution of gold nanoparticles and gene expression changes in the liver and spleen after intravenous administration in rats, Biomaterials, 31 (8):2034-42 (2010).

Bardeesy et al., Pancreatic cancer biology and genetics, Nat. Rev. Cancer, 2(12):897-909 (2002).

Bath et al., DNA nanomachines, Nat. Nanotechnol., 2: 275-84 (2007).

Baudhuim, Photochemical conversion and storage of solar energy. Kluwer Academic Publishers. 251-76 (1990).

Baudhuin et al., Molecular interactions between colloidal gold, proteins, and living cells. Chapter 1: 1-17 (1989).

Berton, et al., Highly loaded nanoparticulate carrier using an hydrophobic antisense oligonucleotide complex, Eur. J. Pharma. Sci., 9: 163-70 (1999).

Besch et al., Characterization and quantification of triple helix formation in chromosomal DNA. J. Mol. Biol., 341: 979-89 (2004).

Bharali et al., Organically modified silica nanoparticles: a nonviral vector for in vivo gene delivery and expression in the brain. Proc. Natl. Acad. Sci. USA, 102(32): 11539-44 (2005).

Biancone et al., Magnetic resonance imaging of gadolinium-labeled pancreatic islets for experimental transplantation, NMR Biomed., 20(1):40-8 (2007).

Bielinska et al., DNA complexing with polyamidoamine dendrimers: implications for transfection. Bioconjug Chem., 10(5): 843-50 (1999).

Birck et al., Mutation and allelic loss of the PTEN/MMAC1 gene in primary and metastatic melanoma biopsies, J. Invest. Dermatol., 114: 277-80 (2000).

Bisht et al., Polymeric nanoparticle-encapsulated curcumin ("nanocurcumin"): a novel strategy for human cancer therapy, J. Nanobiotechnology, 5:3 (2007) (18 pages).

Bowman et al., Inhibition of HIV fusion with multivalent gold nanoparticles, J. Am. Chem. Soc., 130(22):6896-7 (2008).

Bramhill, Bacterial cell division, Annu. Rev. Cell Dev. Biol., 13: 395-424 (1997).

Bratu et al., Visualizing the distribution and transport of mRNAs in living cells, Proc. Natl. Acad. Sci. USA, 100: 13308-13 (2003).

Brown et al., Surface treatment of the hydrophobic drug danazol to improve drug dissolution, Int. J. Pharmaceutics, 165:227-37 (1998).

Brus, Quantum crystallites and nonlinear optics. Appl. Phys. A. 53(6): 465-74 (1991).

Burwell, Modified silica gels as adsorbents and catalysts, Chem. Tech., 4:370-7 (1974).

Cao et al., Raman dye-labeled nanoparticle probes for proteins, J. Am. Chem. Soc., 125(48):14676-7 (2003).

Capaccioli et al., Cationic lipids improve antisense oligonucleotide uptake and prevent degradation in cultured cells and inhuman serum, Biochem. Biophys. Res. Commun., 197(2): 818-25 (1993).

Caravan et al., The interaction of MS-325 with human serum albumin and its effect on proton relaxation rates, J. Am. Chem. Soc., 124(12):3152-62 (2002).

Caravan, Strategies for increasing the sensitivity of gadolinium based MRI contrast agents, Chem. Soc. Rev., 35(6):512-23 (2006).

Castoldi et al., A sensitive array for microRNA expression profiling (miChip) based on locked nucleic acids (LNA), RNA. 12: 913-20 (2006).

Chari et al., Immunoconjugates containing novel maytansinoids: promising anticancer drugs, Cancer Res., 52(1):127-31 (1992).

Charreyre et al., Fluorescence energy transfer study of the conformation of oligonucleotides covalently bound to polystyrene latex particles. Langmuir, 13: 3103-10 (1997).

Chavany et al., Polyalkylcyanoacrylate nanoparticles as polymeric carriers for antisense oligonucleotides, Pharma. Res., 9(4): 441-9 (1992).

Chavany, et al., Adsorption of oligonucleotides onto polyisohexylcyanoacrylate nanoparticles protects them against nucleases and increases their cellular uptake. Pharma. Res., 11(9): 1370-8 (1994).

Chen et al., Kinetics and thermodynamics of DNA hybridization on gold nanoparticles, Nucl. Acids Res., 37: 3756-65 (2009).

Chen et al., MDR 1 activation is the predominant resistance mechanism selected by vinblastine in MES-SA cells, Br. J. Cancer, 83(7):892-8 (2000).

Cheung et al., Akt3 and mutant V600E B-Raf cooperate to promote early melanoma development, Cancer Res., 68:3429-39 (2008).

Chirila et al., The use of synthetic polymers for delivery of therapeutic antisense oligodeoxynucleotides. Biomaterials, 23: 321-42 (2002).

Chithrani et al., Determining the size and shape dependence of gold nanoparticle uptake into mammalian cells, Nano Lett., 6(4):662-8 (2006).

Chithrani et al., Elucidating the mechanism of cellular uptake and removal of protein-coated gold nanoparticles of different sizes and shapes. Nano Lett., 7: 1542-50 (2007).

Chompoosor et al., Charge dependence of ligand release and monolayer stability of gold nanoparticles by biogenic thiols, Bioconjugate Chem., 19:1342-5 (2008).

Chrisey et al., Covalent attachment of synthetic DNA to self-assembled monolayer films, Nucl. Acids Res., 24: 3031-9 (1996).

(56) References Cited

OTHER PUBLICATIONS

Cload et al., Polyether tethered oligonucleotide probes. J. Am. Chem. Soc., 113(16): 6324-6 (1991).
Cook, Medicinal chemistry of antisense oligonucleotides—future opportunities. Anticancer Drug Des., 6(6):585-607 (1991).
Crawford et al., A novel B-RAF inhibitor blocks interleukin-8 (IL-8) synthesis in human melanoma xenografts, revealing IL-8 as a potential pharmacodynamic biomarker, *Mol. Cancer Ther.*, 7:492-9 (2008).
Crawford et al., Peptide aptamers: Tools for biology and drug discovery. 2(1): 72-9 (2003).
Crich et al., Improved route for the visualization of stem cells labeled with a Gd-/Eu-chelate as dual (MRI and fluorescence) agent, Magn. Reson. Med., 51(5):938-44 (2004).
Crooke et al., Progress in antisense technology. Ann. Rev. Med., 55: 61-95 (2004).
Curtis et al., A morphology-selective copper organosol. Angew. Chem. Int. Ed. Engl., 27: 1530-3 (1988).
Daniel et al., Gold nanoparticles: assembly, supramolecular chemistry, quantum-size-related properties, and applications toward biology, catalysis, and nanotechnology. Chem Rev., 104(1): 293-346 (2004).
Dankort et al., A new mouse model to explore the initiation, progression, and therapy of BRAFV600E-induced lung tumors, Genes Dev., 21: 379-84 (2007).
Dankort et al., Braf(V600E) cooperates with Pten loss to induce metastatic melanoma, Nat Genet., 41: 544-52 (2009).
Davies et al., A novel AKT3 mutation in melanoma tumours and cell lines, Br. J. Cancer, 99: 1265-8 (2008).
Debouttiere et al., Design of gold nanoparticles for magnetic resonance imaging, Adv. Funct. Mater., 16:2330-9 (2006).
Demers et al., Combinatorial templates generated by dip-pen nanolithography for the formation of two-dimensional particle arrays, Angew. Chem. Int. Ed., 40: 3071-3 (2003).
DeMesmaeker et al., Antisense oligonucleotides. Acc. Chem. Res., 28(9): 366-74 (1995).
DeMesmaeker et al., Backbone modifications in oligonucleotides and peptide nucleic acid systems, Curr. Opin. Struct. Biol., 5:343-55 (1995).
Deutsch et al., Synthesis of congeners and prodrugs. 3. Water-soluble prodrugs of taxol with potent antitumor activity, J. Med. Chem., 32(4):788-92 (1989).
Devlin et al., Random peptide libraries: a source of specific protein binding molecules, Science, 249: 404-6 (1990).
Dhar et al., Polyvalent oligonucleotide gold nanoparticle conjugates as delivery vehicles for platinum(IV) warheads. *J. Am. Chem. Soc.*, 131(41): 14652-3 (2009).
Dhar et al., Targeted single wall carbon nanotube mediated Pt(IV) prodrug delivery using folate as a homing device. *J. Am. Chem. Soc.*, 130(34): 11467-76 (2008).
Dhomen et al., BRAF signaling and targeted therapies in melanoma, Hematol. Oncol. Clin. North Am., 23: 529-45, ix (2009).
Donachie, The cell cycle of *Escherichia coli.*, *Annu. Rev. Microbiol.*, 47: 199-230 (1993).
Dreyfus et al., Simple quantitative model for the reversible associate of DNA coated colloids, Phys. Rev. Lett., 102: 048301 (2009).
Dubertret et al., Single-mismatch detection using gold-quenched fluorescent oligonucleotides, Nat. Biotechnol., 19: 365-70 (2001).
Duimstra et al., A gadolinium chelate for detection of beta-glucuronidase: a self-immolative approach, J. Am. Chem. Soc., 127(37):12847-55 (2005).
Dulkeith et al., Gold nanoparticles quench fluorescence by phase induced radiative rate suppression, Nano Lett., 5: 585-9 (2005).
Durand et al., Circular dichroism studies of an oligodeoxyribonucleotide containing a hairpin loop made of a hexaethylene glycol chain: conformation and stability. Nucl. Acids Res., 18(21): 6353-9 (1990).
Dykxhoorn et al., Killing the messenger: short RNAs that silence gene expression, Nat. Rev. Mol. Cell Biol., 4(6):457-67 (2003).
Eckstein (ed.), Oligonucleotides and Analogues, 1st Ed., New York, NY: Oxford University Press (1991).
Elaissari et al., Effect of charge nature on the adsorption of single-stranded DNA fragments onto latex particles. J. Colloid Interface Sci., 202: 251-60 (1998).
Elghanian et al., Selective colorimetric detection of polynucleotides based on the distance-dependent optical properties of gold nanoparticles, Science, 277(5329):1078-81 (1997).
Eltekova et al., Adsorption of aromatic compounds from solutions in titanium dioxide and silica, Langmuir, 3:951-7 (1987).
Endres et al., DNA-TiO2 nanoconjugates labeled with magnetic resonance contrast agents, J. Am. Chem. Soc., 129(51):15760-1 and supplementary information (2007).
Englisch et al., Chemically modified oligonucleotides as probes and inhibitors, *Ang. Chem. Int Ed.*, 30:613-29 (1991).
Enustun et al., Coagulation of colloidal gold, J Am Chem Soc, 85:3317-28 (1963).
Examination Report from European Application No. 08729548.1, dated Jan. 19, 2010.
Fahy et al., Design and synthesis of polyacrylamide-based oligonucleotide supports for use in nucleic acid diagnostics, Nucl. Acids Res., 21: 1819-26 (1993).
Fattal et al., Biodegradable polyalkylcyanoacrylate nanoparticles for the delivery of oligonucleotides. J. Control Rel., 53(1-3): 137-43 (1998).
Faulds et al., Evaluation of surface-enhanced resonance Raman scattering for quantitative DNA analysis. Anal. Chem., 76: 412-7 (2004).
Femino et al., Visualization of single RNA transcripts in situ. Science, 280: 585-90 (1998).
Ferentz et al., Disulfide-crosslinked oligonucleotides. J. Am. Chem. Soc., 113(10): 4000-2 (1991).
Final Office Action issued in connection with U.S. Appl. No. 11/917,680, dated Nov. 10, 2010.
Final Office Action issued in connection with U.S. Appl. No. 11/917,680, dated Nov. 10, 2011.
Final Office Action issued in connection with U.S. Appl. No. 12/130,643, dated Jun. 16, 2011.
Flandroy et al., (D, L)Polyactide microspheres as embolic agent. *Neuroradiology*, 32: 311-5 (1990).
Freier et al., The ups and downs of nucleic acid duplex stability: structure-stability studies on chemically-modified DNA:RNA duplexes, Nucleic Acids Res., 25:4429-43 (1997).
Frens, Controlled nucleation for the regulation of the particle size in monodisperse gold suspensions. *Nat. Phys. Sci.*, 241: 20-2 (1973).
Frens, Particle size and sol stability in metal colloids, Kolloid-Zeitschrift und Zeitschrift fur Polymere, 250(7):736-41 (1972).
Frullano et al., Multimodal MRI contrast agents, J. Biol. Inorg. Chem., 12(7):939-40 (2007).
Gao et al., Secondary structure effects on DNA hybridization kinetics: a solution versus surface comparison. Nucl. Acids Res., 34: 3370-7 (2006).
Gavrieli et al., Identification of programmed cell death in situ via specific labeling of nuclear DNA fragmentation, J. Cell Biol., 119(3):493-501 (1992).
Gerdes et al., Experimental determination and system level analysis of essential genes in *Escherichia coli* MG1655. *J. Bacteriol.*, 185: 5673-84 (2003).
Gestwicki et al., Influencing receptor-ligand binding mechanisms with multivalent ligand architecture. J. Am. Chem. Soc., 124: 14922-33 (2002).
Ghosh et al., Gold nanoparticles in delivery applications, Adv. Drug Deliv. Rev. 60(11):1307-15 (2008).
Gibson et al., Paclitaxel-functionalized gold nanoparticles, J. Am. Chem. Soc., 129(37):11653-61 (2007).
Gidwani et al., Hybridization kinetics of double-stranded DNA probes for rapid molecular analysis. Analyst, 134: 1675-81 (2009).
Giljohann et al., Gene regulation with polyvalent siRNA-nanoparticle conjugates, J.Am. Chem. Soc., 131(6):2072-3 (2009).
Giljohann et al., Oligonucleotide loading determines cellular uptake of DNA-modified gold nanoparticles, Nano. Lett., 7(12):3818-21 (2007).
Goel et al., Melanocytic nevus-like hyperplasia and melanoma in transgenic BRAFV600E mice. Oncogene, 28: 2289-98 (2009).

(56) References Cited

OTHER PUBLICATIONS

Grabar et al., Preparation and characterization of Au colloid monolayers, Anal. Chem., 67:735-43 (1995).
Guo et al., CELL-SELEX: Novel perspectives of aptamer-based therapeutics, Int. J. Mol. Sci., 9: 668-78 (2008).
Hale et al., Recruitment of ZipA to the septal ring of *Escherichia coli* is dependent on FtsZ and independent of FtsA. *J. Bacteriol.*, 181: 167-76 (1999).
Hames et al. (eds.), Gene Probes 1, New York: IRL Press (1995).
Hamilton et al., A species of small antisense RNA in post-transcriptional gene silencing in plants. Science, 286: 950-2 (1999).
Hammond et al., An RNA-directed nuclease mediates post-transcriptional gene silencing in *Drosophilia* cells. Nature, 404: 293-6 (2000).
Han et al., A gold nanoparticle based approach for screening triplex DNA binders, J. Am. Chem. Soc., 128(15):4954-5 (2006).
Hayashi, Ultrafine particles, Physics Today, pp. 44-60 (Dec. 1987).
Hayashi, Ultrafine particles, Vac. Sci. Technol. A, 5(4):1375-84 (1987).
Hayat, (Ed.) Colloidal Gold: Principles, Methods, and Applications, vol. 1, Table of Contents, pp. v-xvii; vol. 2, Table of Contents pp. v-xix; vol. 3, Table of Contents, pp. v-xiv, Academic Press, San Diego (1989-1991).
He et al., Colloidal Au-enhanced surface plasmon resonance for ultrasensitive detection of DNA hybridization. J. Am. Chem. Soc., 122(38): 9071-7 (2000).
Hegner et al., Modified DNA immobilized on bioreactive self-assembled monolayer on gold for dynamic force microscopy imaging in aqueous buffer solution, J. Vac. Sci. Technol. B, 14(2):1418-21 (1996).
Henglein et al., Absorption spectrum and some chemical reactions of colloidal platinum in aqueous solution. J. Phys. Chem., 99(38): 14129-36 (1995).
Henglein, Mechanism of reactions on colloidal microelectrodes and size quantization effects. Top. Curr. Chem., 143: 113-80 (1998).
Henglein, Small-particle research: physicochemical properties of extremely small colloidal metal and semiconductor particles. Chem. Rev., 89(8): 1861-73 (1989).
Hickman et al., Combining spontaneous molecular assembly with microfabrication to pattern surfaces: selective binding of isonitriles to platinum microwires and characterization by electrochemistry and surface spectroscopy, J. Am. Chem. Soc., 111:7271-2 (1989).
Holen et al., Positional effects of short interfering RNAs targeting the human coagulation trigger tissue factor. *Nucl. Acids Res.*, 30: 1757-66 (2002).
Hu et al., Advances in high-field magnetic resonance imaging, Annu. Rev. Biomed.Eng., 6:157-84 (2004).
Hubbard, Electrochemistry of well-defined sufaces, Acc. Chem. Res., 13:177-84 (1980).
Hurst et al., "Multisegmented one-dimensional nanorods prepared by hard-template synthetic methods," Angew. Chem. Int. Ed. Engl., 45:2672-2692 (2006).
Hurst et al., Maximizing DNA loading on a range of gold nanoparticle sizes, Anal. Chem., 78(24):8313-8 (2006).
Hussain et al., A novel anionic dendrimer for improved cellular delivery of antisense oligonucleotides. J. Controlled Rel., 99: 139-55 (2004).
Iler, The surface chemistry of silica (chapter 6), In: Iler, Chemistry of Silica, New York: John Wiley & Sons (1979).
International Preliminary Report on Patentability for International Application No. PCT/US2006/022325, dated Dec. 17, 2007.
International Preliminary Report on Patentability for International Application No. PCT/US2008/053603, dated Aug. 11, 2009.
International Preliminary Report on Patentability for International Application No. PCT/US2008/065366, dated Dec. 1, 2009.
International Preliminary Report on Patentability for International application No. PCT/US2009/065822, dated May 24, 2011.
International Preliminary Report on Patentability for International Application No. PCT/US2010/020558, dated Jul. 12, 2011.
International Preliminary Report on Patentability, PCT/US2010/27363, dated Oct. 18, 2011.
International Preliminary Report on Patentability for International Application No. PCT/US2010/044453, dated Feb. 7, 2012.
International Preliminary Report on Patentability for International Application No. PCT/US2010/044844, dated Feb. 7, 2012.
International Preliminary Report on Patentability, PCT/US2010/47591, dated Mar. 6, 2012.
International Preliminary Report on Patentability for corresponding international application No. PCT/US2010/47594, dated Mar. 6, 2012.
International Preliminary Report on Patentability for International Application No. PCT/US2010/55018, dated May 1, 2012.
International Search Report and Written Opinion for International Application No. PCT/US2006/022325, dated Oct. 20, 2006.
International Search Report and Written Opinion for International Application No. PCT/US2008/053603, dated Jul. 30, 2008.
International Search Report and Written Opinion for International Application No. PCT/US2008/065366, dated Aug. 28, 2008.
International Search Report and Written Opinion for International Application No. PCT/US2008/065822, dated Mar. 5, 2010.
International Search Report and Written Opinion for International Application No. PCT/US2010/020558, dated Mar. 9, 2010.
International Search Report and Written Opinion for International Application No. PCT/US2010/044453, dated Apr. 29, 2011.
International Search Report and Written Opinion for International Application No. PCT/US2010/044844, dated Apr. 27, 2011.
International Search Report and Written Opinion for International Application No. PCT/US2010/27363, dated Apr. 15, 2010.
International Search Report and Written Opinion for International Application No. PCT/US2010/47591, dated Oct. 4, 2010.
International Search Report and Written Opinion for corresponding international application No. PCT/US2010/47594, mailing date Oct. 20, 2010.
International Search Report and Written Opinion for International Application No. PCT/US2010/55018, dated Dec. 9, 2010.
Introducing Antisense Oligonucleotides into Cells, Innovation & Precision in Nucleic Acid Synthesis, Integrated DNA Technologies (2005).
Jackson et al., *Escherichia coli* O157:H7 diarrhoea associated with well water and infected cattle on an Ontario farm, *Epidemiol. Infect.*, 120:17-20 (1998).
Jackson et al., How do microRNAs regulate gene expression?, Sci STKE, 2007(367):re1 (2007).
Jaschke et al., Automated incorporation of polyethylene glycol in synthetic oligonucleotides. Tetrahedron Lett., 34: 301-4 (1993).
Jason et al., Toxicology of antisense therapeutics. Toxicol. Appl. Pharmacol., 201(1): 66-83 (2004).
Jen et al., A nonviral transfection approach in vitro: the design of a gold nanoparticle vector joint with microelectromechanical systems. Langmuir, 20(4): 1369-74 (2004).
Jeong et al., Novel intracellular delivery system of antisense oligonucleotide by self-assembled hybrid micelles composed of DNA/PEG conjugate and cationic fusogenic peptide. Bioconjugate Chem., 14: 473-9 (2003).
Jin et al., What controls the melting properties of DNA-linked gold nanoparticle assemblies? J. Am. Chem. Soc., 125: 1643 (2003).
Kalman et al., Potentiometric and relaxometric properties of a gadolinium-based MRI contrast agent for sensing tissue pH, Inorg. Chem., 46(13):5260-70 (2007).
Katz et al., Integrated nanoparticle-biomolecule hybrid systems: synthesis, properties, and applications, Angew. Chem. Int. Ed., 43: 6042-108 (2004).
Katz, The reversible reaction of sodium thymonucleate and mercuric chloride, J. Am. Chem. Soc., 74:2238-45 (1951).
Kim et al., Biodegradable quantum dot nanocomposites enable live cell labeling and imaging of cytoplasmic targets, Nano Lett., 8(11):3887-92 (2008).
Kloosterman et al., In situ detection of miRNAs in animal embryos using LNA-modified oligonucleotide probes, Nat. Methods, 3: 27-9 (2006).
Kolarova et al., Preparation of magnetic oligo (dT) particles, Biotechniques, 20: 196-8 (1996).
Kopylov et al., Combinatorial chemistry of nucleic acids: SELEX, Mol. Biol., 34: 940-54 (2000).

(56) References Cited

OTHER PUBLICATIONS

Kosturko et al., The crystal and molecular structure of a 2:1 complex of 1-methylthymine-mercury(II), Biochemistry, 13:3949-52 (1974).
Kroschwitz (ed.), *The Concise Encyclopedia of Polymer Science and Engineering*, pp. 858-859, New York: John Wiley & Sons (1990).
Krutzfeldt et al., Silencing of microRNAs in vivo with 'antagomirs', Nature, 438(7068):685-9 (2005).
Kukowska-Latallo et al., Efficient transfer of genetic material into mammalian cells using Starburst polyamidoamine dendrimers, Proc. Natl. Acad. Sci. USA, 93: 4897-902 (1996).
Landfester et al., From polymeric particles to multifunctional nanocapsules for biomedical applications using the miniemulsion process, J. Polymer Sci. Part A, 48(3):493-515 (2010).
Lannutti et al., Human angiostatin inhibits murine hemangioendothelioma tumor growth in vivo, Cancer Res., 57: 5277-80 (1997).
Lebedeva et al., Antisense oligonucleotides: Promise and reality. Annu. Rev. Pharmacol. Toxicol., 41: 403-19 (2001).
Lee et al., Adsorption of ordered zirconium phosphonate multilayer films on silicon and gold surfaces, J. Phys. Chem., 92:2597-601 (1988).
Lee et al., Chip-based scanometric detection of mercuric ion using DNA-functionalized gold nanoparticles, Anal. Chem., 80(17):6805-8 (2008).
Lee et al., Colorimetric detection of mercuric ion (Hg2+) in aqueous media using DNA-functionalized gold nanoparticles, Angew. Chem. Int. Ed. Engl., 46(22):4093-6 (2007).
Lemaigre et al., Transcriptional control of genes that regulate glycolysis and gluconeogenesis in adult liver, *Biochem. J.*, 303: 1-14 (1994).
Leslie et al., A new tool for oligonucleotides import into cells. Clin. Chem., 55: 609-10 (2009).
Leunissen et al., Switchable self-protected attractions in DNA-functionalized colloids. Nat. Mater., 8: 590-95 (2009).
Li et al., A calcium-sensitive magnetic resonance imaging contrast agent, J. Am. Chem. Soc., 121:1413-4 (1999).
Lin et al., Effector/memory but not naive regulatory T cells are responsible for the loss of concomitant tumor immunity. J. Immunol., 182: 6095-104 (2009).
Lin et al., Modeling genomic diversity and tumor dependency in malignant melanoma. Cancer Res., 68: 664-73 (2003).
Lipshutz et al., High density synthetic oligonucleotide arrays. Nanotechnology, 14: R15-27 (2003).
Liu et al., Accelerated color change of gold nanoparticles assembled by DNAzymes for simple and fast colorimetric Pb2+ detection. J. Am. Chem. Soc., 126: 12298-305 (2004).
Liu et al., ARDB—Antibiotic Resistance Genes Database. *Nucl. Acids Res.*, 37: D443-7 (2009).
Liu et al., Argonaute2 is the catalytic engine of mammalian RNAi. Science, 305(5689): 1437-41 (2004).
Liu et al., Cross-linked polynorbornene-coated gold nanoparticles: dependence of particle stability on cross-linking position and cross-linker structure, Langmuir, 24(19):11169-74 (2008).
Liu et al., De-N-acetyl GM3 promotes melanoma cell migration and invasion through urokinase plasminogen activator receptor signaling-dependent MMP-2 activation. Cancer Res., 69: 8662-9 (2009).
Liu et al., New poly(d-glucaramidoamine)s induce DNA nanoparticle formation and efficient gene delivery into mammalian cells. J. Am. Chem. Soc., 126: 7422-3 (2004).
Liu et al., Rational design of "turn-on" allosteric DNAzyme catalytic beacons for aqueous mercury ions with ultrahigh sensitivity and selectivity, Angew. Chem. Int. Ed. Engl., 46(60):7587-90 (2007).
Liu et al., Synthesis, stability, and cellular internalization of gold nanoparticles containing mixed peptide-poly(ethylene glycol) monolayers. Anal. Chem., 79: 2221-9 (2007).
Llovet et al., Arterial embolisation or chemoembolisation versus symptomatic treatment in patients with unresectable hepatocellular carcinoma: a randomised controlled trial, Lancet, 359(9319):1734-9 (2002).

Loeken, Effects of mutation of the CREB binding site of the somatostatin promoter on cyclic AMP responsiveness in CV-1 cells. *Gene Expr.*, 3: 253-64 (1993).
Love et al., Self-assembled monolayers of thiolates on metals as a form of nanotechnology. Chem. Rev., 105: 1103-69 (2005).
Lutkenhaus et al., Bacterial cell division and the Z ring. *Annu. Rev. Biochem.*, 66: 93-116 (1997).
Lytton-Jean et al., A thermodynamic investigation into the binding properties of DNA functionalized gold nanoparticle probes and molecular fluorophore probes. J. Am. Chem Soc., 127: 12754-5 (2005).
Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res., 21: 2585-9 (1993).
Ma et al., Design and synthesis of RNA miniduplexes via a synthetic linker approach. Biochemistry, 32(7): 1751-8 (1993).
Major et al., Bioresponsive, cell-penetrating, and multimeric MR contrast agents, Acc. Chem. Res., 42(7):893-903 (2009).
Major et al., The synthesis and in vitro testing of a zinc-activated MRI contrast agent, Proc. Natl. Acad. Sci. USA, 104(35):13881-6 (2007).
Maoz et al., Penetration-controlled reactions in organized monolayer assemblies. 1. Aqueous permanganate interaction with monolayer and multilayer films of long-chain surfactants, Langmuir, 3:1034-44 (1987).
Maoz et al., Penetration-controlled reactions in organized monolayer assemblies. 2. Aqueous permanganate interaction with self-assembling monolayers of long-chain surfactants, Langmuir, 3:1045-51 (1987).
Marinakos et al., Gold nanoparticles as templates for the synthesis of hollow nanometer-sized conductive polymer capsules, Adv. Mater, 11:34-37 (1999).
Marinakos et al., Template synthesis of one-dimensional Au, Au—poly(pyrrole), and poly(pyrrole) nanoparticle arrays, Chem Mater, 10:1214-19 (1998).
Martin et al., 38. Ein neuer zugang zu 2'-O-alkylribonucleosiden und eigenschaften deren oligonucleotide, *Helv. Chim. Acta*, 78: 486-504 (1995) [English abstract only.].
Martinez et al., Locked nucleic acid based beacons for surface interaction studies and biosensor development. Anal. Chem., 81: 3448-54 (2009).
Maruyama, et al., Nanoparticle DNA carrier with poly(L-lysine) grafted polysaccharide copolymer and poly(D,L-lactic acid). Bioconjugate Chem., 8: 735-742 (1997).
Massart, Preparation of aqueous magnetic liquids in alkaline and acidic media. IEEE Transactions on Magnetics. 17(2): 1247-8 (1981).
Matijevic (ed.), Fine particles part II: Formation mechanisms and applications, MRS Bulletin, pp. 16-47 (Jan. 1990).
Matsuura et al., Construction and characterization of protein libraries composed of secondary structure modules. Protein Sci., 11: 2631-43 (2002).
Matteucci et al., Synthesis of deoxyoligonucleotides on a polymer support, J. Am. Chem. Soc., 103:3185-3191 (1981).
Mattson et al., A practical approach to crosslinking. *Molec. Biol. Rep.*, 17: 167-83 (1993).
Maxwell et al., Self-assembled nanoparticle probes for recognition and detection of biomolecules. J. Am. Chem. Soc., 124: 9606-12 (2002).
Maye et al., A simple method for kinetic control of DNA-induced nanoparticle assembly. J. Am. Chem. Soc., 128: 14020-1 (2006).
Mayer (ed.), Nucleic Acid and Peptide Aptamers: Methods and Protocols (Humana Press, 2009).
McCurdy et al., Deoxyligonucleotides with inverted polarity: Synthesis and use in triple-helix formation. Nucleosides & Nucleotides, 10: 287-90 (1991).
McGehee et al., Differentiation-specific element: a cis-acting developmental switch required for the sustained transcriptional expression of the angiotensinogen gene during hormonal-induced differentiation of 3T3-L1 fibroblasts to adipocytes. Mol. Endocrinol., 7: 551-60 (1993).

(56) References Cited

OTHER PUBLICATIONS

McKenzie et al., Sequence-specific DNA detection using high-affinity LNA-functionalized gold nanoparticles. Small, 3(11): 1866-8 (2007).
McManus et al., Gene silencing in mammals by small interfering RNAs. Nat. Rev. Genet., 3(10): 737-47 (2002).
Mendell, MicroRNAs: critical regulators of development, cellular physiology and malignancy, Cell Cycle, 4(9):1179-84 (2005).
Merbach et al. (eds.), The Chemistry of Contrast Agents in Medical Magnetic Resonance Imaging, 1st ed., New York: Wiley (2001).
Miller et al., Antisense oligonucleotides: Strategies for delivery. PSTT, 1(9): 377-86 (1998).
Milne et al., An approach to gene-specific transcription inhibition using oligonucleotides complementary to the template strand of the open complex. *Proc. Natl. Acad. Sci. USA*, 97(7): 3136-41 (2000).
Mirkin et al., A DNA-based method for rationally assembling nanoparticles into macroscopic materials, Nature, 382(6592):607-9 (1996).
Mittal, Improving the efficiency of RNA interference in mammals, Nat. Rev. Genet., 5(5):355-65 (2004).
Modo et al. (eds.), Molecular and Cellular MR Imaging, Florida: CRC Press (2007).
Modo et al., Mapping transplanted stem cell migration after a stroke: a serial, in vivo magnetic resonance imaging study, Neuroimage, 21(1):311-7 (2004).
Moriggi et al., Gold nanoparticles functionalized with gadolinium chelates as high-relaxivity MRI contrast agents, J. Am. Chem. Soc., 131(31):10828-9 (2009).
Mucic et al., Synthesis and characterization of DNA with ferrocenyl groups attached to their 5'-termini: electrochemical characterization of a redox-active nucleotide monolayer, Chem. Comm., 555-7 (1996).
Myers et al., A cyclopentane conformational restraint for a peptide nucleic acid: design, asymmetric synthesis, and improved binding affinity to DNA and RNA. Org Lett., 5(15): 2695-8 (2003).
Nam et al., Nanoparticle-based bio-bar codes for the ultrasensitive detection of proteins. Science, 301: 1884-6 (2003).
Nielsen et al., Sequence-selective recognition of DNA by strand displacement with a thymine-substituted polyamide, Science, 254:1497-1500 (1991).
Nitin et al., Peptide-linked molecular beacons for efficient delivery and rapid mRNA detection in living cells. Nucl. Acids Res., 32: e58 (2004).
Nitin, et al. "Oligonucleotide-Coated Metallic Nanoparticles as a Flexible Platform for Molecular Imaging Agents," Bioconjugate Chem. 18:2090-2096 (2007).
Non-Final Office Action issued in connection with U.S. Appl. No. 11/917,680, dated Jun. 8, 2011.
Non-Final Office Action issued in connection with U.S. Appl. No. 12/130,643, dated Jan. 13, 2011.
Non-Final Office Action issued in connection with U.S. Appl. No. 12/526,560, dated Mar. 15, 2012.
Non-Final Office Action issued in connection with U.S. Appl. No. 12/625,537, dated May 23, 2012.
Non-Final Office Action issued in connection with U.S. Appl. No. 12/684,836, dated Jan. 6, 2012.
Non-Final Office Action issued in connection with U.S. Appl. No. 12/684,836, dated May 17, 2012.
Non-Final Office Action issued in connection with U.S. Appl. No. 12/724,395, dated Feb. 17, 2012.
Notice of Allowance issued in connection with U.S. Appl. No. 11/917,680, dated Apr. 26, 2012.
Nuzzo et al., Spontaneously organized molecular assemblies. 3. Preparation and properties of solution adsorbed monolayers of organic disulfides on gold surfaces, J. Am. Chem. Soc., 109:2358-68 (1987).
Nykypanchuk et al., DNA-guided crystallization of colloidal nanoparticles. Nature, 451: 549-52 (2008).
O'Meara et al., Capture of single-stranded DNA assisted by oligonucleotide modules. Anal. Biochem., 255: 195-203 (1998).
O'Reilly et al., Identification of an activating transcription factor (ATF) binding site in the human transforming growth factor-beta 2 promoter. *J. Biol. Chem.*, 267: 19938-43 (1992).
Ohuchi et al., In vitro method for the generation of protein libraries using PCR amplification of a single DNA molecule and coupled transcription/translation, Nucl. Acids Res., 26: 4339-46 (1998).
Olshaysky et al., Organometallic synthesis of gallium-arsenide crystallites, exhibiting quantum confinement. J. Am. Chem. Soc., 112(25): 9438-9 (1990).
Ono et al., DNA triplex formation of oligonucleotide analogues consisting of linker groups and octamer segments that have opposite sugar-phosphate backbone polarities. Biochemistry, 30(41): 9914-2 (1991).
Opalinska et al., Nucleic-acid therapeutics: basic principles and recent applications. Nat. Rev. Drug Discov., 1: 503-14 (2002).
Ow Sullivan et al., Development of a novel gene delivery scaffold utilizing colloidal gold-polyethylenimine conjugates for DNA condensation. Gene Ther., 10(22): 1882-90 (2003).
Ozpolat et al., Nanomedicine based approaches for the delivery of siRNA in cancer, J. Intern. Med., 267(1):44-53 (2010).
Paciotti et al., Colloidal gold: a novel nanoparticle vector for tumor directed drug delivery, Drug Deliv., 11(3):169-83 (2004).
Parak et al., Biological applications of colloidal nanocrystals, Nanotechnol., 14: R15-27 (2003).
Park et al., Array-based electrical detection of DNA with nanoparticle probes. Science, 295: 1503-6 (2002).
Park et al., DNA-programmable nanoparticle cystrallization. Nature, 451: 553-6 (2008).
Park et al., Gold nanoparticles functionalised by Gd-complex of DTPA-bis(amide) conjugate of glutathione as an MRI contrast agent, Bioorg. Med. Chem. Lett., 18(23):6135-7 (2008).
Parrish et al., Functional anatomy of a dsRNA trigger: Differential requirement for the two trigger strands in RNA interference. Mol. Cell, 6: 1077-87 (2000).
Patel et al., Peptide antisense nanoparticles. Proc. Natl. Acad. Sci. USA, 105: 17222-6 (2008).
Patel et al., Scavenger receptors mediate cellular uptake of polyvalent oligonucleotide-functionalized gold nanoparticles, Bioconjug. Chem., 21(12):2250-6 (2010).
Patil et al., DNA-based therapeutics and DNA delivery systems: a comprehensive review. AAPS J., 7(1): E61-77 (2005).
Paunesku et al., Gadolinium-conjugated TiO2-DNA oligonucleotide nanoconjugates show prolonged intracellular retention period and T1-weighted contrast enhancement in magnetic resonance images, Nanomedicine, 4(3):201-7 (2008).
Peng et al., Real-time detection of gene expression in cancer cells using molecular beacon imaging: New strategies for cancer research. Cancer Res., 65: 1909-17 (2005).
Penn et al., Nanoparticles for bioanalysis. Curr. Opin. Chem. Biol., 7: 609-15 (2003).
Peracchi, Prospects for antiviral ribozymes and deoxyribozymes. *Rev. Med. Virol.*, 14: 47-64 (2004).
Perlette et al., Real-time monitoring of intracellular mRNA hybridization inside single living cells. Anal. Chem., 73: 5544-50 (2001).
Pon, Solid-phase supports for oligonucleotide synthesis. *Meth. Molec. Biol.*, 20: 465-96 (1993).
Prausnitz et al., Transdermal drug delivery, Nat. Biotechnol., 26: 1261-8 (2008).
Prigodich et al., Nano-flares for mRNA regulation and detection. ACS Nano, 3: 2147-52 (2009).
Prime et al., Self-assembled organic monolayers; Model systems for studing adsorption of proteins at surfaces. Science, 252: 1164-7 (1991).
Raj et al., Stochastic mRNA synthesis in mammalian cells. PLoS Biol., 4(10): e309 (2006).
Rethore et al., Preparation of chitosan/polyglutamic acid spheres based on the use of polystyrene template as nonviral gene carrier. *Tissue Engineering*, 15(4): 605-13 (2009).
Riccelli et al., Hybridization of single-stranded DNA targets to immobilized complementary DNA probes: comparison of hairpin versus linear capture probes. Nucl. Acids Res., 29: 996-1004 (2001).

(56) References Cited

OTHER PUBLICATIONS

Richardson et al., Tethered oligonucleotide probes. A strategy for the recognition of structured RNA. J. Am. Chem. Soc., 113(13): 5109-11 (1991).
Rihova et al., Receptor-mediated targeted drug or toxin delivery. Adv. Drug Deliv. Rev., 29(3): 273-89 (1998).
Rizzo et al., Chimeric RNA-DNA molecular beacon assay for ribonuclease H activity. Mol. Cell Probes, 16: 277-83 (2002).
Rosi et al., Nanostructures in biodiagnostics, Chem. Rev., 105(4):1547-62 (2005).
Rosi et al., Oligonucleotide-modified gold nanoparticles for intracellular gene regulation, Science, 312(5776):1027-30 (2006).
Sadauskas et al., Protracted elimination of gold nanoparticles from mouse liver, Nanomedicine, 5(2):162-9 (2009).
Sambrook et al., Molecular Cloning: A Laboratory Manual, 2nd ed. (1989).
Sandhu et al., Gold nanoparticle-mediated transfection of mammalian cells. Bioconjugate Chem., 13: 3-6 (2002).
Sanghvi, Heterocyclic base modifications in nucleic acids and their applications in antisense oligonucleotides, Chapter 15 in Crooke et al. (eds.), *Antisense Research and Applications*, CRC Press (1993).
Santangelo et al., Dual FRET molecular beacons for mRNA detection in living cells. Nucl. Acids Res., 32:e57 (2004).
Santangelo et al., Nanostructured probes for RNA detection in living cells. Ann. Biomed. Eng., 34:39-50 (2006).
Schifferlers et al., Cancer siRNA therapy by tumor selective delivery with ligand-targeted sterically stabilized nanoparticle. *Nucl. Acid Res.*, 32(19): e149 (2004).
Schmid, G. (ed.) Clusters and Colloids (VCH, Weinheim, 1994).
Seela et al., Oligodeoxyribonucleotides containing 1,3-propanediol as nucleoside substitute. Nucl. Acids Res., 15(7): 3113-29 (1987).
Seelig et al., Catalyzed relaxation of a metastable DNA fuel. J. Am. Chem. Soc., 128: 12211-20 (2006).
Seferos et al., Locked nucleic acid-nanoparticle conjugates. Chembiochem., 8: 1230-2 (2007).
Seferos et al., Nano-flares: probes for transfection and mRNA detection in living cells. J. Am. Chem. Soc., 129: 15477-9 (2007).
Seferos et al., Polyvalent DNA nanoparticle conjugates stabilize nucleic acids, Nano Lett., 9(1):308-11 (2009).
Sharma et al., Mutant V599EB-Raf regulates growth and vascular development of malignant melanoma tumors. Cancer Res., 65: 2412-21 (2005).
Sharma et al., Targeting Akt3 signaling in malignant melanoma using isoselenocyanates. Clin. Cancer Res., 15:.1674-85 (2009).
Sharma et al., Targeting mitogen-activated protein kinase/extracellular signal-regulated kinase kinase in the mutant (V600E) B-Raf signaling cascade effectively inhibits melanoma lung metastases. Cancer Res., 66: 8200-9 (2006).
Sharp et al., RNA interference—2001. Genes Dev., 15: 485-90 (2001).
Simmel et al., DNA nanodevices. Small, 1: 284-99 (2005).
Smith et al., Bioconjugated quantum dots for in vivo molecular and cellular imaging, Adv. Drug Deliv. Rev., 60(11):1226-40 (2008).
Sokol et al., Real time detection of DNA.RNA hybridization in living cells. Proc. Natl. Acad. Sci. USA, 95: 11538-43 (1998).
Song et al., Synthesis of multimeric MR contrast agents for cellular imaging, J. Am. Chem. Soc., 130(21):6662-3 (2008).
Soriaga et al., "Determination of the orientation of aromatic molecules adsorbed on platinum electrodes. The effect of solute concentration." J. Am. Chem. Soc., 104:3937-3945 (1982).
Srivastava et al., Use of riboprobes for northern blotting analysis. Biotechniques, 11(5): Abstract (1991).
Stahl et al., Deregulated Akt3 activity promotes development of malignant melanoma, Cancer Res., 64: 7002-10 (2004).
Stephenson et al., Inhibition of Rous sarcoma viral RNA translation by a specific oligodeoxyribonucleotide. Proc. Natl. Acad. Sci. USA, 75(1): 285-8 (1978).
Stoermer et al., Distance-dependent emission from dye-labeled oligonucleotides on striped Au/Ag nanowires: effect of secondary structure and hybridization efficiency. J. Am. Chem. Soc., 128: 13243-54 (2006).
Stoeva et al., Multiplexed detection of protein cancer markers with biobarcoded nanoparticle probes. J. Am. Chem. Soc., 128: 8378-9 (2006).
Storhoff et al., One-pot colorimetric differentiation of polynucleotides with single base imperfections using gold nanoparticle probes, J. Am. Chem. Soc., 120:1959-64 (1998).
Storhoff et al., What controls the optical properties of DNA-linked gold nanoparticle assemblies? J. Am. Chem. Soc., 122: 4640-50 (2000).
Sun et al., Ganglioside loss promotes survival primarily by activating integrin-linked kinase/Akt without phosphoinositide 3-OH kinase signaling. J. Invest. Dermatol., 119: 107-17 (2002).
Sundaram et al., Particle-mediated delivery of recombinant expression vectors to rabbit skin induces high-titered polyclonal antisera (and circumvents purification of a protein immunogen). Nucl. Acids Res., 24(7): 1375-7 (1996).
Taton et al., Scanometric DNA array detection with nanoparticle probes, Science, 289(5485):1757-60 (2000).
Thomas et al., Conjugation to gold nanoparticles enhances polyethylenimine's transfer of plasmid DNA into mammalian cells. Proc. Natl. Acad. Sci. USA, 100(16): 9138-43 (2003).
Thomas, The interaction of HgCl2 with sodium thymonucleate, J. Am. Chem. Soc., 76:6032-4 (1954).
Thompkins et al., The study of the gas-solid interaction of acetic acid with a cuprous oxide surface using reflection-absorption spectroscopy. J. Colloid Interface Sci., 49: 410-21 (1974).
Thurn et al., Labeling TiO2 nanoparticles with dyes for optical fluorescence microscopy and determination of TiO2-DNA nanoconjugate stability, Small, 5(11):1318-25 (2009).
Timmons et al., Investigation of fatty acid monolayers on metals by contact potential measurements, J. Phys. Chem., 69:984-90 (1965).
Tkachenko et al., Cellular trajectories of peptide-modified gold particle complexes: comparison of nuclear localization signals and peptide transduction domains. Bioconjugate Chem., 15(3): 482-90 (2004).
Tkachenko et al., Multifunctional gold nanoparticle-peptide complexes for nuclear targeting. J. Am. Chem. Soc., 125: 4700-1 (2003).
Tondelli, et al., Highly efficient cellular uptake of c-myb antisense oligonucleotides through specifically designed polymeric nanospheres. Nucl. Acids Res., 26: 5425-31 (1998).
Treisman, The SRE: a growth factor responsive transcriptional regulator. *Semin. Cancer Biol.*, 1: 47-58 (1990).
Tsao et al., Genetic interaction between NRAS and BRAF mutations and PTEN/MMAC1 inactivation in melanoma. J. Invest. Dermatol., 122: 337-41 (2004).
Tuerk et al., Systematic evolution of ligands by exponential enrichment: RNA ligands to bacteriophage T4 DNA polymerase. Science, 249: 505-10 (1990).
Turberfield et al., DNA fuel for free-running nanomachines. Phys. Rev. Lett., 90: 118102 (2003).
Tyagi et al., Molecular beacons: Probes that fluoresce upon hybridization. Nat. Biotechnol., 14: 303-8 (1996).
Uchida et al., GaAs nanocrystals prepared in quinoline. *J. Phys. Chem.* 95(14): 5382-4 (1991).
Vasiliskov et al., Parallel multiplex thermodynamic analysis of coaxial base stacking in DNA duplexes by oligodeoxyribonucleotide microchips. Nucl. Acids Res., 29: 2303-13 (2001).
Virmani et al., Comparison of two different methods for inoculating VX2 tumors in rabbit livers and hind limbs, J. Vasc. Interv. Radiol., 19(6):931-6 (2008).
Wagner et al., Gene inhibition using antisense oligodeoxynucleotides. Nature, 372: 333-5 (1994).
Wang et al., Ganglioside GM3 inhibits matrix metalloproteinase-9 activation and disrupts its association with integrin, J. Biol. Chem., 278: 25591-9 (2003).
Wang et al., Ganglioside GM3 promotes carcinoma cell proliferation via urokinase plasminogen activator-induced extracellular signal-regulated kinase-independent p70S6 kinase signaling, J. Invest. Dermatol., 126: 2687-96 (2006).

(56) References Cited

OTHER PUBLICATIONS

Wang et al., Inhibition of integrin-linked kinase/protein kinase B/Akt signaling: mechanism for ganglioside-induced apoptosis. J. Biol. Chem., 276: 44504-11 (2001).
Wang et al., Locked nucleic acid molecular beacons. J. Am. Chem. Soc., 127: 15664-5 (2005).
Wang et al., Molecular engineering of DNA: molecular beacons. Angew. Chem., Int. Ed., 48: 856-70 (2009).
Wang et al., Nanometer-sized semiconductor clusters: materials synthesis, quantum size effects, and photophysical properties. J. Phys. Chem., 95(2): 525-32 (1991).
Wang et al., Nanoparticles for multiplex diagnostics and imaging. Nanomedicine (Lond.), 1: 413-26 (2006).
Wang et al., Speeding up a single-molecule DNA device with a simple catalyst. Phys. Rev. E Stat. Nonlin. Soft Matter. Phys., 72: 051918 (2005).
Wang et al., Superparamagnetic sub-5 nm Fe@C nanoparticles: isolation, structure, magnetic properties, and directed assembly, Nano Lett., 8(11):3761-5 (2008).
Warnmark et al., Activation functions 1 and 2 of nuclear receptors: molecular strategies for transcriptional activation, Mol. Endocrinol., 17(10):1901-9 (2003).
Wasserman et al., Structure and reactivity of alkylsiloxane monolayers formed by reaction of alkyltrichlorosilanes on silicon substrates, Langmuir, 5:1074-87 (1989).
Watson et al. (Eds.), *Molecular Biology of the Gene*, 4th ed., The Benjamin/Cummings Publishing Company Inc. (1987).
Wei et al., A study of the relationships between oligonucleotide properties and hybridization signal intensities from NimbleGen microarray datasets. Nucl. Acids Res., 36: 2926-38 (2008).
Wellbrock et al., V599EB-RAF is an oncogene in melanocytes. Cancer Res., 64: 2338-42 (2004).
Weller, Colloidal Semiconductor Q-particles: Chemistry in the transition region between solid state and molecules. Angew. Chem. Int. Ed. Engl., 32(1): 41-53 (1993).
Whitesides, Proceedings of the Robert A. Welch Foundation 39th Conference on Chemical Research Nanophase Chemistry, Houston, Tex., pp. 109-121 (1995).
Wikipedia entry on Aspirin, Last modified on Oct. 6, 2010 (online). Retrieved on Oct. 7, 2010). Retrieved from the Internet: <URL: http://en.wikipedia.org/wiki/Aspirin>.
Wikipedia entry on Phenylbutazone. Last modified on Sep. 20, 2010. Online. (Retrieved on Oct. 7, 2010). Retrieved from the Internet: <URL:http://en.wikipedia.org/wiki/Phenylbutazone>.
Wikipedia entry on Warfarin. Last modified on Oct. 5, 2010. (Online) (Retrieved on Oct. 8, 2010). Retrieved from the Internet: <URL:http://en.wikpedia.org/wiki/Warfarin>.
Winter et al., Molecular imaging by MRI, Curr. Cardiol. Rep. 8(1):65-9 (2006).
Wolf et al., Rapid hybridization kinetics of DNA attached to submicron latex particles. Nucl. Acids Res., 15: 2911-26 (1987).
Xia, Nanomaterials at work in biomedical research, Nat. Mater., 7(10):758-60 (2008).
Xu et al., A gold-nanoparticle-based real-time colorimetric screening method for endonuclease activity and inhibition, Angew. Chem. Int. Ed. Engl., 46(19):3468-70 (2007).
Xu et al., Homogeneous detection of nucleic acids based upon the light scattering properties of silver-coated nanoparticle probes, Anal. Chem., 79(17):6650-4 (2007).
Xu et al., Thermodynamics of DNA hybridization on gold nanoparticles. J. Am. Chem. Soc., 127(38): 13227-31 (2005).
Yamane et al., On the complexing of desoxyribonucleic acid (DNA) by mercuric ion, J. Am. Chem. Soc., 83:2599-607 (1961).
Yan et al., Aptamers and aptamer targeted delivery. RNA Biol., 6: 316-20 (2009).
Yang et al., Evidence that processed small dsRNAs may mediate sequence-specific mRNA degradation during RNAi in *Drosophila* embryos. Curr. Biol., 10: 1191-200 (2000).

Ye et al., Characterization of a silencer regulatory element in the human interferon-gamma promoter. *J. Biol. Chem.*, 269: 25728-34 (1994).
Yin Win et al., Effects of particle size and surface coating on cellular uptake of polymeric nonparticles for oral delivery of anticancer drugs. Biomaterials, 26: 2713-22 (2005).
You et al., Detection and identification of proteins using nanoparticle-fluorescent polymer 'chemical nose' sensors. Nat. Nanotechnol., 2: 318-23 (2007).
You et al., Engineering the nanoparticle-biomacromolecule interface. Soft Matter, 2: 190-204 (2006).
Zabner et al., Cellular and molecular barriers to gene transfer by a cationic lipid. J. Biol. Chem., 270: 18997-9007 (1995).
Zamecnik et al., Inhibition of Rous sarcoma virus replication and cell transformation by a specific oligodeoxynucleotide. Proc. Natl. Acad. Sci. USA, 75(1): 280-4 (1978).
Zamore et al., RNAi: double-stranded Rna directs the ATP-dependent cleavage of mRNA at 21 to 23 nucleotide intervals. Cell, 101: 25-33 (2000).
Zhang et al., An extremely stable and orthogonal DNA base pair with a simplified three-carbon backbone, J. Am. Chem. Soc., 127:74-5 (2005).
Zhang et al., Control of DNA strand displacement kinetics using toehold exchange. J. Am. Chem. Soc., 131: 17303-14 (2009).
Zhang et al., PowerBlast: A new network BLAST application for interactive or automated sequence analysis and annotation. Genome, 7: 649-56 (1997).
Zhang et al., Single-quantum-dot-based DNA sensor. Nat. Mater., 4: 826-31 (2005).
Zhao et al., A rapid bioassay for single bacterial cell quantitation using bioconjugated nanoparticles, Proc. Natl. Acad. Sci. USA, 101 (42):15027-32 (2004).
Zheng et al., Aptamer nano-flares for molecular detection in living cells. Nano Lett., 9: 3258-61 (2009).
Zimmer, Antisense oligonucleotide delivery with polyhexylcyanoacrylate nanoparticles as carriers. Methods, 18: 286-95 (1999).
Zimmerman et al., "A novel silver(1)-mediated DNA base pair," J. Am. Chem. Soc., 124:13684-13685 (2002).
Cha et al., Hepatocellular carcinoma: current management, Curr. Probl. Surg., 47(1):10-67 (2010).
Chu et al., Effects of photoactivated 5-aminolevulinic acid hexyl ester on MDR1 over-expressing human uterine sarcoma cells, Toxicology Lett., 181:7-12 (2008).
Connor et al., Gold nanoparticles are taken up by human cells but do not cause acute cytotoxicity, Small, 1(3):325-7 (2005).
Giljohann et al., Gold nanoparticles for biology and medicine, Angew. Chem. Int. Ed. Engl., 49:3280-94 (2010).
Hashmi et al., Gold-catalyzed organic reactions, Chem. Rev., 107(7):3180-211 (2007).
Jin et al., Radiosensitization of paclitaxel, etanidazole and paclitaxel +etanidazole nanoparticles on hypoxic human tumor cells in vitro, Biomaterials, 28:3724-30 (2007).
Kan et al., Role of Kupffer cells in iodized oil embolization, Invest. Radiol., 29(11):990-3 (1994).
Patra et al., Targeted delivery of gemcitabine to pancreatic adenocarcinoma using cetuximab as a targeting agent, Cancer Res., 68(6):1970-8 (2008).
Ries et al., SEER Cancer Statistics Review 1975-2005, Cancer of the Pancreas Table 22.8, Bethesda, MD: National Cancer Institute (2008).
Skwarczynski et al., Paclitaxel prodrugs: toward smarter delivery of anticancer agents, J. Med. Chem., 49(25):7253-69 (2006).
Zhang et al., A novel paclitaxel-loaded poly(e-caprolactone)/ Poloxamer 188 blend nanoparticle overcoming multidrug resistance for cancer treatment, Acta Biomaterialia, 6:2045-52 (2010).
Alivisatos et al., "Organization of 'nanocrystal molecules' using DNA," Nature, 382: 609-11 (1996).
Anton et al., "Design and production of nanoparticles formulated from nano-emulsion templates—a review," J. Control Release, 128(3):185-99 (2008).

(56) References Cited

OTHER PUBLICATIONS

Cheng et al., "Tandem synthesis of core-shell brush copolymers and their transformation to peripherally cross-linked and hollowed nanostructures," J. Am. Chem. Soc., 128(21):6808-9 (2006).
Choi et al., "Hollow spherical nanocapsules of poly(pyrrole) as a promising support for Pt/Ru nanoparticles based catalyst," Mater. Chem., 120(1):18-22 (2010).
Fukuda et al., "Effective Transformation of Unactivated Alkynes into Ketones or Acetals by Means of Au(III) Catalyst," J. Org. Chem., 56(11):3729-31 (1991).
Fukuda et al., "Efficient Transformation of Methyl Propargyl Ethers into $\alpha,\beta$-Unsaturated Ketones," Bull. Chem. Soc. Jpn., 64:2013-2015 (1991).
Furstner et al., "Catalytic carbophilic activation: catalysis by platinum and gold pi acids," Angew Chem Int Ed Engl., 46(19):3410-49 (2007).
Goodrich et al., "Non-coding-RNA regulators of RNA polymerase II transcription," Nat. Rev. Mol. Cell Biol., 7(8):612-6 (2006).
Hashmi et al., "Gold catalysis," Angew Chem Int Ed Engl., 45(47):7896-936 (2006).
Hu et al., "Hollow chitosan/poly(acrylic acid) nanospheres as drug carriers," Biomacromolecules, 8(4):1069-76 (2007).
Hwu et al., "Targeted Paclitaxel by conjugation to iron oxide and gold nanoparticles, J. Am. Chem. Soc.," 131(1):66-8 (2009).
Kan et al., "Distribution and effect of iodized poppyseed oil in the liver after hepatic artery embolization: experimental study in several animal species," Radiology, 186(3):861-6 (1993).
Kasuya et al., "Chapter 8—Bio-nanocapsule-liposome conjugates for in vivo pinpoint drug and gene delivery," Methods Enzymol., 464:147-66 (2009).
Kim et al., "Direct synthesis of polymer nanocapsules with a noncovalently tailorable surface," Angew. Chem. Int. Ed. Engl., 46(19):3471-4 (2007).
Kim et al., "Direct synthesis of polymer nanocapsules: self-assembly of polymer hollow spheres through irreversible covalent bond formation," J. Am. Chem. Soc., 132(28):9908-19 (2010).
Kim et al., "Facile, template-free synthesis of stimuli-responsive polymer nanocapsules for targeted drug delivery," Angew. Chem. Int. Ed. Engl., 49(26):4405-8 (2010).
Kondo et al., "Nanotube formation through the continuous one-dimensional fusion of hollow nanocapsules composed of layer-by-layer poly(lactic acid) stereocomplex films," J. Am. Chem. Soc., 132(24):8236-7 (2010).
Lewis, "Controlled release of bioactive agents from lactide/glycolide polymer", pp. 1-41, IN: Chasin et al. (eds.), Biodegradable Polymers as Drug Delivery Systems, Marcel Dekker (1990).
Li et al., "Dual-reactive surfactant used for synthesis of functional nanocapsules in miniemulsion," J. Am. Chem. Soc., 132(23):7823-5 (2010).
Li et al., "Gold-catalyzed organic transformations," Chem. Rev., 108(8):3239-65 (2008).
Li et al., "Reversible and chemically programmable micelle assembly with DNA block-copolymer amiphiphiles," Nano Lett., 4(6):1055-8 (2004).
Link et al., "Size and Temperature Dependence of the Plasmon Absorption of Colloidal Gold Nanoparticles," J. Phys. Chem. B, 103(21):4212-7 (1999).
Liu et al., "DNA-based micelles: synthesis, micellar properties and size-dependent cell permeability," Chemistry, 16(12):3791-7 (2010).
Moughton et al., "Hollow nanostructures from self-assembled supramolecular metallo-triblock copolymers," Soft Matter, 5(12):2361-70 (2009).
Ohishi et al., "Hepatocellular carcinoma detected by iodized oil. Use of anticancer agents, Radiology," 154(1):25-9 (1985).
Okayasu et al., "Selective and persistent deposition and gradual drainage of iodized oil, Lipiodol in the hepatocellular carcinoma after injection into the feeding hepatic artery," Am. J. Clin. Pathol., 90(5):536-44 (1988).
Rethore et al., "Use of templates to fabricate nanoscale spherical structures for defined architectural control," Small, 6(4):488-98 (2010).
Rostovtsev, et al. "A Stepwise Huisgen Cycloaddition Process: Copper(I)-Catalyzed Regioselective "Ligation" of Azides and Terminal Alkynes," Angew. Chem. Int. Ed. 41(14):2596-2599 (2002).
Sharma et al., "Characterization of MRI contrast agent-loaded polymeric nanocapsules as versatile vehicle for targeted imaging," Contrast Media Mol. Imaging, 5(2):59-69 (2010).
Shu et al., "Gradient cross-linked biodegradable polyelectrolyte nanocapsules for intracellular protein drug delivery," Biomaterials, 31(23):6039-49 (2010).
Storz et al., "An abundance of RNA regulators," Annu. Rev. Biochem., 74:199-217 (2005).
Sugihara et al., "One-pot synthesis of biomimetic shell cross-linked micelles and nanocages by ATRP in alcohol/water mixtures," Angew. Chem. Int. Ed. Engl., 48(20):3500-3 (2010).
Tan et al., "Facile synthesis of hybrid silica nanocapsules by interfacial templating condensation and their application in fluorescence imaging," Chem. Commun. (Camb.), Nov. 7(41):6240-2 (2009).
Thaxton et al., "Templated Spherical High Density Lipoprotein Nanoparticles," J. Am. Chem. Soc. 131 (4): 1384-5 (2009).
Turner et al., "Nanoscale Cage-like Structures Derived from Polyisoprene-Containing Shell Cross-linked Nanoparticle Templates," Nano Lett., 4(4):683-8 (2004).
Zhang et al., "Structure-Activity Relationships of Cationic Shell-crosslinked Knedel-like Nanoarticles: Shell Composition and Transfection Efficiency/Cytotoxicity," Biomaterials 31:1805 (2010).
Zhang et al., "Cationic shell-crosslinked knedel-like nanoparticles for highly efficient gene and oligonucleotide transfection of mammalian cells," Biomaterials, 30(5):968-77 (2009).
Zhang et al., "Self-assembled monolayers of terminal alkynes on gold," J. Am. Chem. Soc., 129(16):4876-7 (2007).

\* cited by examiner

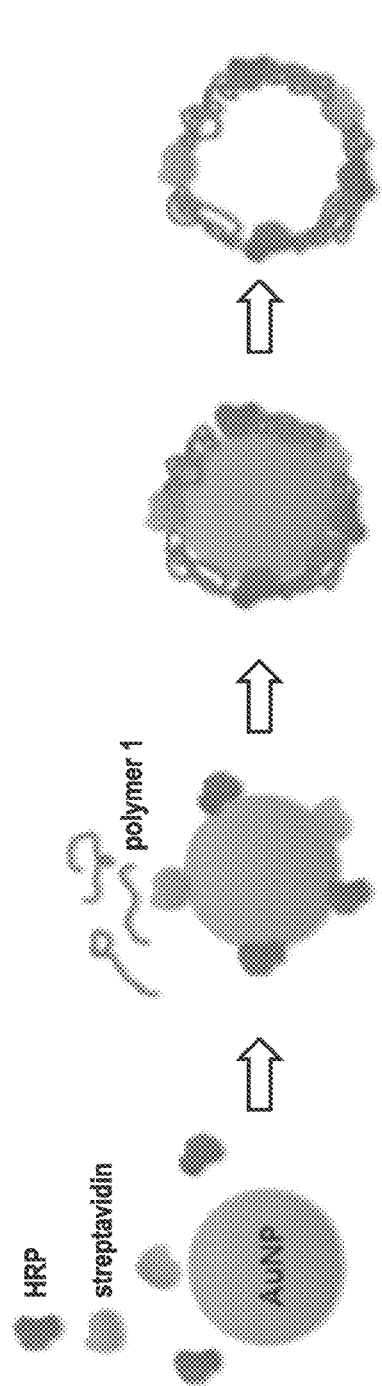
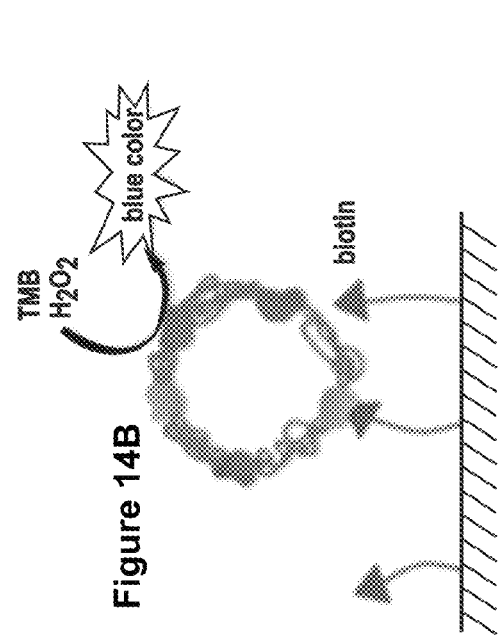
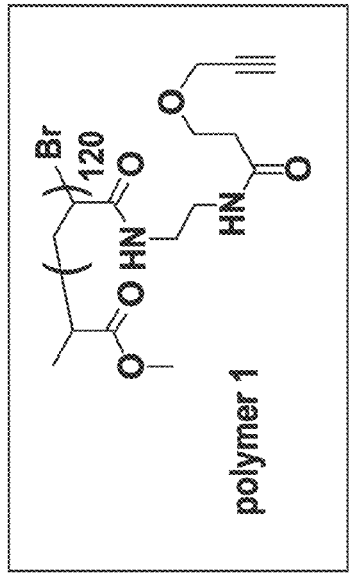
Figure 14A
Figure 14B

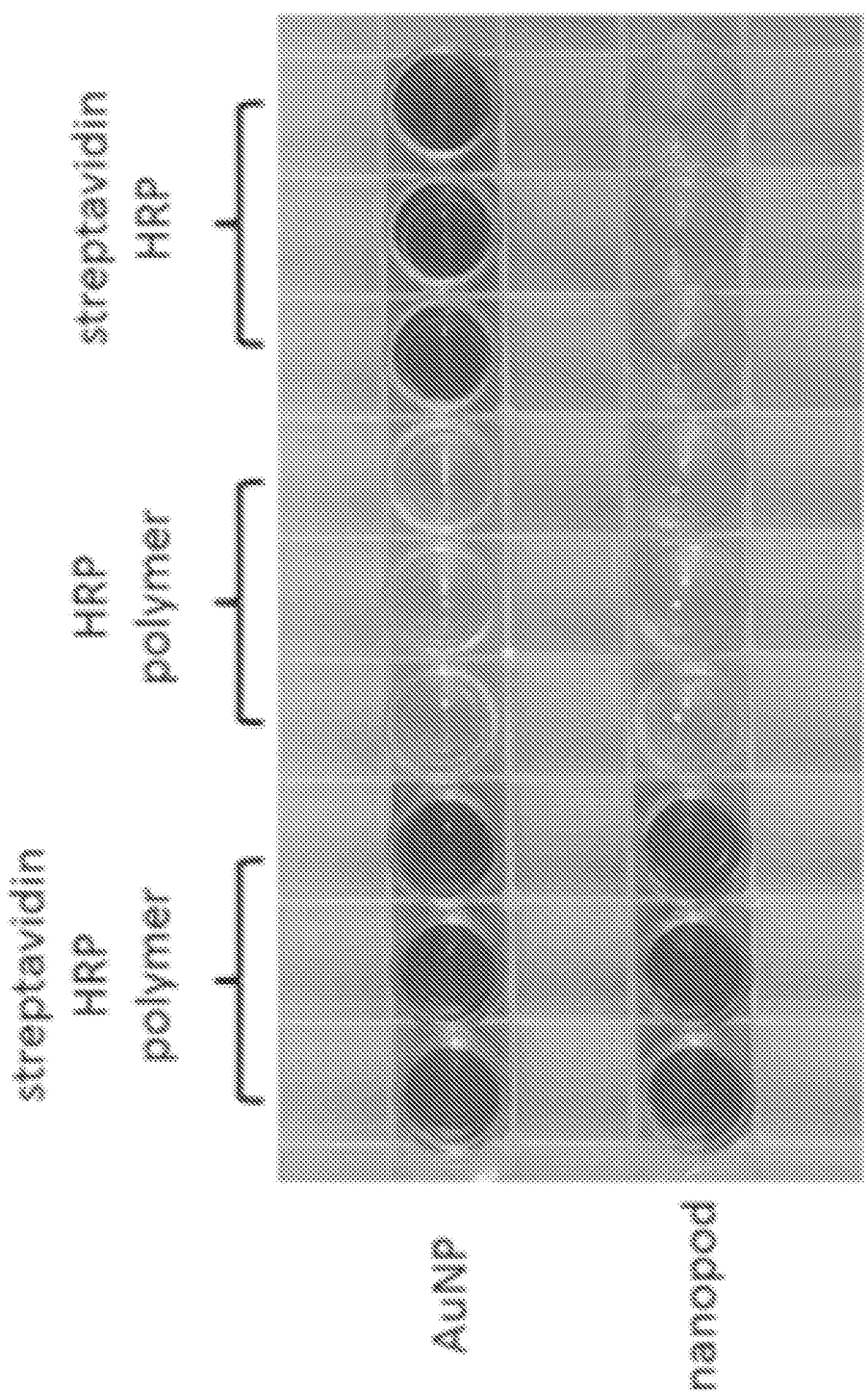

TEMPLATED NANOCONJUGATES

CROSS-REFERENCE TO RELATED APPLICATIONS

This application is a U.S. National Phase of International Application No. PCT/US2010/055018 filed Nov. 1, 2010, which claims the priority benefit under 35 U.S.C. §119(e) of U.S. Provisional Application No. 61/256,640, filed Oct. 30, 2009, U.S. Provisional Application No. 61/374,550, filed Aug. 17, 2010 and U.S. Provisional Application No. 61/386,846, filed Sep. 27, 2010, the disclosures of which are incorporated herein by reference in their entirety.

STATEMENT OF GOVERNMENT INTEREST

This invention was made with government support under Grant Number W911NF-09-1-0069, awarded by the U.S. Army RDECOM, and Grant Number U54 CA119341, awarded by the National Institutes of Health (NCI-CCNE). The government has certain rights in the invention.

FIELD OF THE INVENTION

The present disclosure is directed to compositions comprising templated nanoconjugates and methods of their use.

BACKGROUND OF THE INVENTION

Nucleic acids that regulate gene expression are widely considered to be potential therapeutics as well as important tools for gene function analysis. The potential of nucleic acid methods lies in their ability to regulate gene pathways by recognizing and binding complementary targets present in cells. However, the delivery of nucleic acids into mammalian cells remains a major challenge, as cells are naturally resistant to nucleic acid uptake. Additionally, they have a variety of mechanisms that degrade and destroy foreign nucleic acids both inside and outside the cell. Therefore, the creation of vectors that can non-toxically penetrate cellular membranes and deliver programmed nucleic acids without the aid of external transfection agents is necessary for the extension of these technologies to therapeutic application.

Polyvalent inorganic nanomaterials are now recognized as potential therapeutic agents in vivo, and in some cases are already FDA cleared for use as diagnostic tools [Rosi et al., Chem. Rev. 105 (4): 1547-1562 (2005); Taton et al., Science 289 (5485): 1757-1760 (2000)]. Because the surface of these particles can be associated with biomolecules through a variety of attachment strategies, they can be engineered through the choice of their surface ligands, to interact with well-known biological systems and pathways. For example, by modifying gold nanoparticles with a dense shell of duplexed siRNA, it possible to engage RNAi gene silencing in mammalian cells [Giljohann et al., J. Am. Chem. Soc. 131 (6): 2072-2073 (2009)]. These particles are particularly effective as RNAi gene regulation agents because they exhibit high cellular uptake without transfection agents [Rosi et al., Science 312 (5776): 1027-1030 (2006)], lack of acute toxicity, resistance to nuclease degradation [Seferos et al., Nano Lett. 9(1): 308-11 (2009)] and high stability in biological media. It is important to note that a growing body of work suggests that the gold nanoparticle-polynucleotide conjugate's ability to perform these various functions stems solely from the tightly packed arrangement of polynucleotides on the particles' surface [Giljohann et al., Nano Lett. 7 (12): 3818-21 (2007)]. In another example, a biomimetic synthetic high density lipoprotein (HDL) nanoconjugate can be constructed by modifying gold nanoparticles with a dense shell of phospholipids and APO1A, which is a biologically relevant protein [Thaxton et al., J. Am. Chem. Soc. 131 (4): 1384-5 (2009)]. HDL is a dynamic serum molecule protective against the development of atherosclerosis and resultant illnesses such as heart disease and stroke. Like biogenic HDL, this synthetic construct is capable of binding cholesterol in its hydrophobic phospholipid shell. Importantly, in both of these cases and many others, it is the dense polyvalent arrangement of biological ligands on the surface of inorganic nanoparticles that imparts their unique ability to interact with biological systems, regardless of their core material.

Although biological-inorganic nanomaterial hybrids possess desirable attributes, such as those used for diagnostics and therapeutics, concerns have arisen over the clearance/persistence and toxicity of the core material in vivo. Because these concerns are widely recognized as limitations for the use of nanomaterials in vivo, a universal approach is needed to create soft nanomaterials with tailorable surface functionalities that would maintain the properties of their inorganic nanoparticle bioconjugate counterparts. Attempts have been made to address these problems through a number of synthetic strategies, which includes micellar structures [Li et al., Nano Lett. 4 (6): 1055-1058 (2004); Liu et al., Chem-Eur J 16 (12): 3791-3797 (2010)].

Hollow nanoconjugates have attracted significant interest in recent years due to their unique chemical, physical, and biological properties, which suggest a wide range of applications in drug/gene delivery [Shu et al., Biomaterials 31: 6039 (2010); Kim et al., Angew. Chem. Int. Ed. 49: 4405 (2010); Kasuya et al., In Meth. Enzymol.; Nejat, D., Ed.; Academic Press: 2009; Vol. Volume 464, p 147], imaging [Sharma et al., Contrast Media Mol. Imaging 5: 59 (2010); Tan et al., J. Chem. Commun. 6240 (2009)], and catalysis [Choi et al., Chem. Phys. 120: 18 (2010)]. Accordingly, a variety of methods have been developed to synthesize these structures based upon emulsion polymerizations [Anton et al., J. Controlled Release 128: 185 (2008); Landfester et al., J. Polym. Sci. Part A: Polym. Chem. 48: 493 (2010); Li et al., J. Am. Chem. Soc. 132: 7823 (2010)], layer-by-layer processes [Kondo et al., J. Am. Chem. Soc. 132: 8236 (2010)], crosslinking of micelles [Turner et al., Nano Lett. 4: 683 (2004); Sugihara et al., Angew. Chem. Int. Ed. 49: 3500 (2010); Moughton et al., Soft Matter 5: 2361 (2009)], molecular or nanoparticle self-assembly [Kim et al., Angew. Chem. Int. Ed. 46: 3471 (2007); Kim et al., J. Am. Chem. Soc. 132(28): 9908-19 (2010)], and sacrificial template techniques [Réthoré et al., Small 6: 488 (2010)]. Among them, the templating method is particularly powerful in that it transfers the ability to control the size and shape of the template to the product, for which desired homogeneity and morphology can be otherwise difficult to achieve. In a typical templated synthesis, a sacrificial core is chosen, upon which preferred materials containing latent crosslinking moieties are coated. Following the stabilization of the coating through chemical crosslinking, the template is removed, leaving the desired hollow nanoparticle. This additional crosslinking step can be easily achieved for compositionally simple molecules, such as poly(acrylic acid) or chitosan [Cheng et al., J. Am. Chem. Soc. 128: 6808 (2006); Hu et al., Biomacromolecules 8: 1069 (2007)]. However, for systems containing sensitive and/or biologically functional structures, conventional crosslinking chemistries may not be sufficiently orthogonal to prevent the loss of their activity.

SUMMARY OF THE INVENTION

The present disclosure provides compositions comprising templated nanoconjugates and methods of their use. Disclosed herein are methods for creating nanoconjugates, with or without a surface. In one aspect, biomolecules bearing one or more moieties that can be crosslinked are activated, which initiates crosslinking reactions between biomolecules. In some aspects, the activation is spontaneous. After the reaction is complete, the surface is optionally be dissolved and the resulting hollow structures retain the shape of the surface. The hollow structures without the surface exhibit properties of the nanoconjugate in which the surface remains intact.

Thus, the disclosure provides a plurality of nanoconjugates, each nanoconjugate having a defined structure and comprising a plurality of crosslinked biomolecules in a monolayer, a surface providing a template upon which the structure is assembled, wherein the surface is optionally at least partially removed after the structure has been defined.

In various aspects, the nanoparticle is selected from the group consisting of a gold nanoparticle, a silver nanoparticle, a platinum nanoparticle, an aluminum nanoparticle, a palladium nanoparticle, a copper nanoparticle, a cobalt nanoparticle, an indium nanoparticle, and a nickel nanoparticle.

In an embodiment, the disclosure provides a nanoconjugate wherein each biomolecule in the plurality of biomolecules is the same. In another embodiment, the disclosure provides a nanoconjugate wherein at least two of the biomolecules in the plurality of biomolecules are different.

In various embodiments, the biomolecule is selected from the group consisting of a polynucleotide, peptide, polypeptide, phospholipid, oligosaccharide, small molecule, therapeutic agent, contrast agent and combinations thereof.

In further embodiments, the plurality of nanoconjugates is monodisperse. In various aspects, the monodispersity is such that there is about 25% variation in the diameter of the plurality of nanoconjugates, or wherein the monodispersity is such that there is about 10% variation in the diameter of the plurality of nanoconjugates, or wherein the monodispersity is such that there is about 1% variation in the diameter of the plurality of nanoconjugates.

In some embodiments, the density of crosslinked biomolecules on the surface is sufficient for cooperative behavior between the biomolecules. In various aspects, a plurality of nanoconjugates are provided wherein density of crosslinked biomolecules on the surface is about 2 pmol/cm$^2$, or wherein density of crosslinked biomolecules on the surface is about 100 pmol/cm$^2$.

In a further aspect of the disclosure, a plurality of nanoconjugates is provided wherein the plurality of nanoconjugates further comprises an additional agent. In various aspects, the additional agent is selected from the group consisting of a polynucleotide, peptide, polypeptide, phospholipid, oligosaccharide, metal complex, small molecule, therapeutic agent, contrast agent and combinations thereof.

In one embodiment, the additional agent is associated with at least one biomolecule of the plurality of biomolecules. In various aspects, the additional agent is associated with at least one biomolecule of the plurality of biomolecules through hybridization, while in additional aspects the additional agents is covalently or noncovalently associated with at least one biomolecule of the plurality of biomolecules. In a further aspect, the additional molecule is entrapped in the crosslinked biomolecules of at least one of the plurality of nanoconjugates.

The disclosure also provides, in various embodiments, a plurality of nanoconjugates wherein at least one nanoconjugate in the plurality of nanoconjugates is hollow in the absence of the surface, or wherein a majority of the nanoconjugates in the plurality of nanoconjugates is hollow in the absence of the surface, or wherein substantially all of the nanoconjugates in the plurality of nanoconjugates are hollow in the absence of the surface.

In one embodiment, a plurality of nanoconjugates is provided wherein in at least one of the plurality of nanoconjugates, an additional agent is encapsulated in the nanoconjugate which is otherwise hollow.

Also provided by the disclosure, in one embodiment, is a method of crosslinking a structured nanoconjugate, the method comprising the step of activating a first biomolecule by contacting the first biomolecule with a surface, the activation allowing the first biomolecule to crosslink to a second biomolecule. In one aspect, the surface provides a template upon which the structure is assembled, while in another aspect the surface is a nanoparticle. In various aspects, the nanoparticle is selected from the group consisting of a sphere, a rod and a prism.

The methods provided by the disclosure also provide, in various aspects, that the nanoparticle is metallic, and in further aspects that the nanoparticle is a colloidal metal. Thus, in still further aspects, the nanoparticle is selected from the group consisting of a gold nanoparticle, a silver nanoparticle, a platinum nanoparticle, an aluminum nanoparticle, a palladium nanoparticle, a copper nanoparticle, a cobalt nanoparticle, an indium nanoparticle, and a nickel nanoparticle.

The disclosure also provides that in various embodiments of any of the methods described herein, the surface is at least partially removed after the crosslinking.

Further provided by the disclosure, and in some aspects, are methods wherein the first biomolecule and the second biomolecule are selected from the group consisting of a polynucleotide, peptide, polypeptide, phospholipid, oligosaccharide, small molecule, therapeutic agent, contrast agent and combinations thereof. In further aspects, the first biomolecule and the second biomolecule comprise at least one alkyne moiety, or the first biomolecule and the second biomolecule each comprise about 10 alkyne moieties.

Regarding the alkyne moiety, the disclosure provides in various aspects that the alkyne moiety is activated upon contact with the surface. In one aspect, the activation renders the alkyne susceptible to a nucleophile, and in various embodiments the nucleophile is selected from the group consisting of water, an alcohol, an amine, a thiol, an ester, a thioester, urea, an amide, an aldehyde, a carbonate, a carbamate, an intramolecular hydroxyl group, a methyl ether group, a benzylic ether group, a carboxylic acid, a ketone, an imine, phenol, 2-pyrrolidone, an indole, acetic acid, a β-ketoester and combinations thereof.

In various embodiments of the disclosure, activation causes crosslinking of the first biomolecule to the second biomolecule.

In some aspects, the first biomolecule is a polynucleotide, and in further aspects the second biomolecule is a polynucleotide. In still further aspects, the polynucleotide is a DNA polynucleotide or a RNA polynucleotide.

The disclosure also provides, in various embodiments, that the polynucleotide is about 5 to about 100 nucleotides in length, about 5 to about 90 nucleotides in length. about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, or about 5 to about 10 nucleotides in length.

In another embodiment, the additional agent is added to the first biomolecule and the second biomolecule during the crosslinking step, while in another embodiment the additional agent is added to the nanoconjugate after formation of the nanoconjugate but before removal of the surface. In a further embodiment, the additional agent is added to the nanoconjugate after formation of the nanoconjugate and after removal of the surface.

In another aspect, a composition is provided comprising a polyvalent nanoconjugate comprising a surface, the nanoconjugate further comprising a plurality of polynucleotides wherein a spacer end of each of the polynucleotides in the plurality is modified such that contacting the plurality of polynucleotides with a chemical crosslinks the plurality of polynucleotides, wherein the surface is optionally at least partially removed after the crosslinking. In various aspects of the composition, the nanoconjugate comprises a nanoparticle, and in further aspects the nanoparticle is selected from the group consisting of a sphere, a rod and a prism.

Accordingly, in still further aspects of the composition, the nanoparticle is metallic. In one aspect, the nanoparticle is a colloidal metal. In various embodiments of the composition, the nanoparticle is selected from the group consisting of a gold nanoparticle, a silver nanoparticle, a platinum nanoparticle, an aluminum nanoparticle, a palladium nanoparticle, a copper nanoparticle, a cobalt nanoparticle, an indium nanoparticle, and a nickel nanoparticle.

In various embodiments, the modification is selected from the group consisting of an amine, amide, alcohol, ester, aldehyde, ketone, thiol, disulfide, carboxylic acid, phenol, imidazole, hydrazine, hydrazone, azide and an alkyne. In one aspect, the modification is an amine-modified nucleotide, and in a further aspect the amine-modified phosphoramidite nucleotide is an amine-modified thymidine phosphoramidite (TN).

In further embodiments, the chemical is selected from the group consisting of Disuccinimidyl glutarate, Disuccinimidyl suberate, Bis[sulfosuccinimidyl] suberate, Tris-succinimidyl aminotriacetate, succinimidyl 4-hydrazinonicotinate acetone hydrazone, succinimidyl 4-hydrazidoterephthalate hydrochloride, succinimidyl 4-formylbenzoate, Dithiobis [succinimidyl propionate], 3,3'-Dithiobis[sulfosuccinimidylpropionate], Disuccinimidyl tartarate, Bis[2-(succinimidooxycarbonyloxy)ethyl]sulfone, Ethylene glycol bis [succinimidylsuccinate], Ethylene glycol bis [sulfosuccinimidylsuccinate], Dimethyl adipimidate.2 HCl, Dimethyl pimelimidate.2 HCl, Dimethyl Suberimidate.2 HCl, 1,5-Difluoro-2,4-dinitrobenzene, β-[Tris(hydroxymethyl)phosphino]propionic acid, Bis-Maleimidoethane, 1,4-bismaleimidobutane, Bismaleimidohexane, Tris[2-maleimidoethyl]amine, 1,8-Bis-maleimido-diethyleneglycol, 1,11-Bis-maleimido-triethyleneglycol, 1,4 bismaleimidyl-2,3-dihydroxybutane, Dithio-bismaleimidoethane, 1,4-Di-[3'-(2'-pyridyldithio)-propionamido]butane, 1,6-Hexane-bisvinylsulfone, Bis-[b-(4-Azidosalicylamido)ethyl]disulfide, N-(a-Maleimidoacetoxy) succinimide ester, N-[β-Maleimidopropyloxy]succinimide ester, N[g-Maleimidobutyryloxy] succinimide ester, N-[g-Maleimidobutyryloxy]sulfosuccinimide ester, m-Maleimidobenzoyl-N-hydroxysuccinimide ester, m-Maleimidobenzoyl-N-hydroxysulfosuccinimide ester, Succinimidyl 4-[N-maleimidomethyl]cyclohexane-1-carboxylate, Sulfosuccinimidyl 4-[N-maleimidomethyl]cyclohexane-1-carboxylate, N-e-Maleimidocaproyloxy]succinimide ester, N-e-Maleimidocaproyloxy]sulfosuccinimide ester, Succinimidyl 4-[p-maleimidophenyl]butyrate, Sulfosuccinimidyl 4-[p-maleimidophenyl]butyrate, Succinimidyl-6-[β-maleimidopropionamido]hexanoate, Succinimidyl-4-[N-Maleimidomethyl]cyclohexane-1-carboxy-[6-amidocaproate], N-[k-Maleimidoundecanoyloxy] sulfosuccinimide ester, N-Succinimidyl 3-(2-pyridyldithio)-propionate, Succinimidyl 6-(3-[2-pyridyldithio]-propionamido)hexanoate, 4-Succinimidyloxycarbonyl-methyl-a-[2-pyridyldithio]toluene, 4-Sulfosuccinimidyl-6-methyl-a-(2-pyridyldithio)toluamido]hexanoate), N-Succinimidyl iodoacetate, Succinimidyl 3-[bromoacetamido]propionate, N-Succinimidyl[4-iodoacetyl]aminobenzoate, N-Sulfosuccinimidyl[4-iodoacetyl]aminobenzoate, N-Hydroxysuccinimidyl-4-azidosalicylic acid, N-5-Azido-2-nitrobenzoyloxysuccinimide, N-Hydroxysulfosuccinimidyl-4-azidobenzoate, Sulfosuccinimidyl[4-azidosalicylamido]-hexanoate, N-Succinimidyl-6-(4'-azido-2'-nitrophenylamino)hexanoate, N-Sulfosuccinimidyl-6-(4'-azido-2'-nitrophenylamino)hexanoate, Sulfosuccinimidyl-(perfluoroazidobenzamido)-ethyl-1,3'-dithioproprionate, Sulfosuccinimidyl-2-(m-azido-o-nitrobenzamido)-ethyl-1, 3'-proprionate, Sulfosuccinimidyl 2-[7-amino-4-methylcoumarin-3-acetamido]ethyl-1,3'dithiopropionate, Succinimidyl 4,4'-azipentanoate, Succinimidyl 6-(4,4'-azipentanamido)hexanoate, Succinimidyl 2-([4,4'-azipentanamido]ethyl)-1,3'-dithioproprionate, Sulfosuccinimidyl 4,4'-azipentanoate, Sulfosuccinimidyl 6-(4,4'-azipentanamido)hexanoate, Sulfosuccinimidyl 2-([4, 4'-azipentanamido]ethyl)-1,3'-dithioproprionate, Dicyclohexylcarbodiimide, 1-Ethyl-3-[3-dimethylaminopropyl]carbodiimide Hydrochloride, N-[4-(p-Azidosalicylamido) butyl]-3'-(2'-pyridyldithio)propionamide, N-[β-Maleimidopropionic acid]hydrazide, trifluoroacetic acid salt, [N-e-Maleimidocaproic acid]hydrazide, trifluoroacetic acid salt, 4-(4-N-Maleimidophenyl)butyric acid hydrazide hydrochloride, N-[k-Maleimidoundecanoic acid]hydrazide, 3-(2-Pyridyldithio)propionyl hydrazide, p-Azidobenzoyl hydrazide, N-[p-Maleimidophenyl]isocyanate and Succinimidyl-[4-(psoralen-8-yloxy)]-butyrate.

In another aspect, the plurality of polynucleotides comprise DNA polynucleotides, RNA polynucleotides or a combination thereof, and in various embodiments the polynucleotide is about 5 to about 100 nucleotides in length, about 5 to about 90 nucleotides in length. about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, or about 5 to about 10 nucleotides in length.

In further embodiments, the disclosure also provides methods of making any of the nanoconjugates of the disclosure using a method described herein.

In another aspect of the disclosure a method of detecting a target molecule is provided comprising contacting the target molecule with any of the nanoconjugate compositions described herein, wherein contact between the target molecule and the composition results in a detectable change. In various aspects, the detecting is in vitro or the detecting is in vivo.

The disclosure also provides, in various aspects, a method of inhibiting expression of a gene product encoded by a target polynucleotide comprising contacting the target polynucleotide with any of the nanoconjugate compositions described herein under conditions sufficient to inhibit expression of the gene product. In various aspects, expression of the gene product is inhibited in vivo or expression of the gene product is inhibited in vitro. In a further aspect, expression of the gene product is inhibited by at least about 5%.

The disclosure additionally provides, in various embodiments, compositions of the disclosure made by any of the methods described herein.

DESCRIPTION OF THE DRAWINGS

FIG. 14A depicts the construction of proteonanoconjugates containing streptavidin and HRP. FIG. 14B depicts a surface-based chromogenic analysis of the HRP activity of the proteonanoconjugate.

FIG. 15 shows HRP-catalyzed chromogenic analysis of proteonanoconjugates, showing successful incorporation of streptavidin and HRP into the nanoconjugate shell and retention of the protein function.

DETAILED DESCRIPTION OF THE INVENTION

Figure 1:
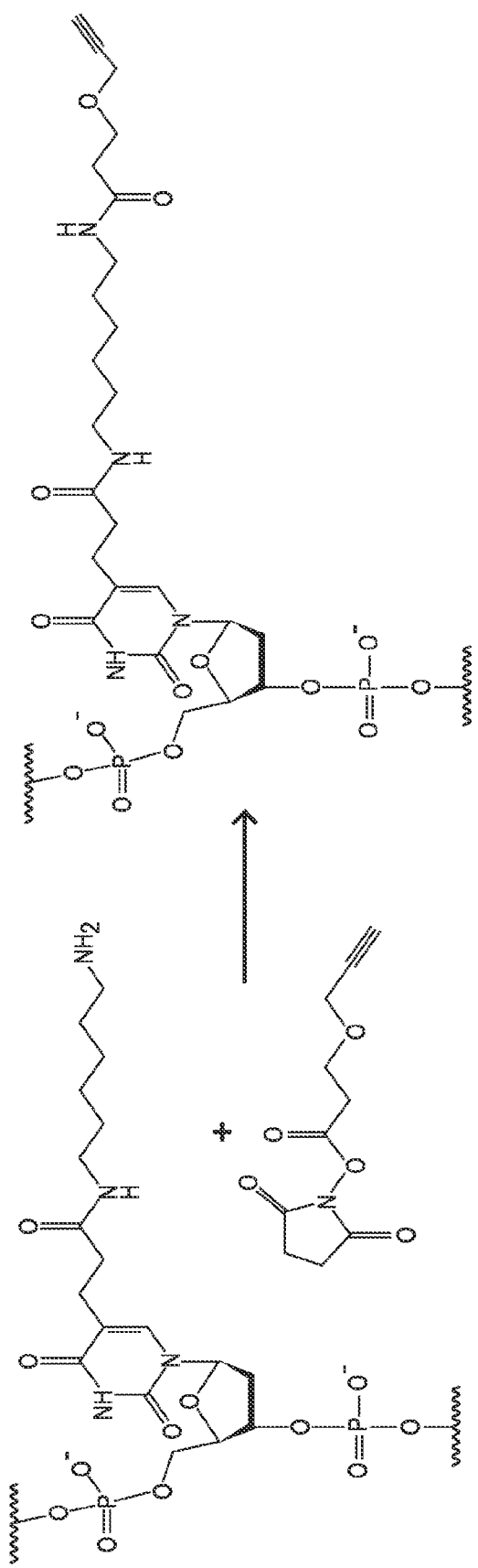
FIG. 1 depicts modification of amine-modified DNA with an alkyne-NHS ester.

Provided herein are compositions comprising a plurality of nanoconjugates, each nanoconjugate having a defined structure and comprising a plurality of crosslinked biomolecules in a monolayer, the structure defined by a surface and the plurality of nanoconjugates being monodisperse, wherein the presence of the surface is optional after the structure has been defined.

The nanoconjugates disclosed are effective alternatives to functionalized nanoparticles as described in, for example, Rosi et al., Chem. Rev. 105(4): 1547-1562 (2005), Taton et al., Science 289(5485): 1757-1760 (2000), PCT/US2006/022325 and U.S. Pat. No. 6,361,944 because they exhibit high cellular uptake without transfection agents, lack acute toxicity, exhibit resistance to nuclease degradation and have high stability in biological media. The combination of these properties is significant since, despite the tremendously high uptake of biomolecule-functionalized nanoparticles, they exhibit no toxicity in the cell types tested thus far (see Table 1, below), and this property is critical for therapeutic agent delivery applications for reducing off-target effects.

TABLE 1

| Cell Type | Designation or Source |
| --- | --- |
| Breast | SKBR3, MDA-MB-321, AU-565 |
| Brain | U87, LN229 |
| Bladder | HT-1376, 5637, T24 |
| Colon | LS513 |
| Cervix | HeLa, SiHa |
| Skin | C166, KB, MCF, 10A |
| Kidney | MDCK |
| Blood | Sup T1, Jurkat |
| Leukemia | K562 |
| Liver | HepG2 |
| Kidney | 293T |
| Ovary | CHO |
| Macrophage | RAW 264.7 |
| Hippocampus Neurons | primary, rat |
| Astrocytes | primary, rat |
| Glial Cells | primary, rat |
| Bladder | primary, human |
| Erythrocytes | primary, mouse |
| Peripheral Blood Mononuclear Cell | primary, mouse |
| T-Cells | primary, human |
| Beta Islets | primary, mouse |
| Skin | primary, mouse |

The disclosure thus provides compositions and methods relating to the generation of nanoconjugates. In one aspect, the nanoconjugate comprises biomolecules that are crosslinked to each other and attached to a surface. In some aspects, the surface is dissolved leaving a hollow nanoconjugate. Thus, a nanoconjugate comprising a biomolecule and/or non-biomolecule as used herein can will be understood to mean either a nanoconjugate in which the surface is retained, or a nanoconjugate in which the surface has been dissolved as described herein. A nanoconjugate in which the surface has been dissolved is referred to herein as a hollow nanoconjugate or hollow particle.

Accordingly, a plurality of nanoconjugates is provided wherein each nanoconjugate has a defined structure and comprises a plurality of crosslinked biomolecules in a monolayer. The structure of each nanoconjugate is defined by (i) the surface that was used in the manufacture of the nanoconjugates (ii) the type of biomolecules forming the nanoconjugate, and (iii) the degree and type of crosslinking between individual biomolecules on and/or around the surface. While the surface is integral for producing the nanoconjugates, the surface is not integral to maintaining the structure of the nanoconjugates. Thus in alternative embodiments, the plurality of nanoconjugates either includes the surface used in their production or the plurality includes a partial surface, or the plurality does not include the surface.

The term "surface" means the structure on or around which the nanoconjugate forms.

As used herein, a "biomolecule" is understood to include a polynucleotide, peptide, polypeptide, phospholipid, oligosaccharide, small molecule, therapeutic agent, contrast agent and combinations thereof.

It is noted here that, as used in this specification and the appended claims, the singular forms "a," "an," and "the" include plural reference unless the context clearly dictates otherwise.

It is also noted that the term "about" as used herein is understood to mean approximately.

It is further noted that the terms "attached," "conjugated" and "functionalized" are used interchangeably herein and refer to the association of a polynucleotide, peptide, polypeptide, phospholipid, oligosaccharide, metal complex, small molecule, therapeutic agent, contrast agent and combinations thereof with a surface.

As used herein, a "majority" means greater than 50% of a population (for example and without limitation, a population of biomolecules or a population of nanoconjugates). Also as used herein, "substantially all" means 90% or greater of a population.

Nanoconjugates

Biomolecules/Non-Biomolecules

The basic component of nanoconjugates provided is a plurality of biomolecules. In alternative embodiments, however, nanoconjugates are provided wherein one or more non-biomolecules are included in the plurality of biomolecules. Because of the methods of production, the resulting nanoconjugates are at most a monolayer of biomolecules or mixture of biomolecules and non-biomolecules. As used herein, a "monolayer" means that only a single stratum of biomolecules and/or non-biomolecules is crosslinked at the surface of a nanoconjugate.

A biomolecule as used herein includes without limitation a polynucleotide, peptide, polypeptide, phospholipid, oligosaccharide, small molecule, therapeutic agent, contrast agent and combinations thereof.

A non-biomolecule as used herein includes without limitation a diluent molecule, a metal complex and any non-carbon containing molecule known in the art.

In various aspects of the nanoconjugate, all of the biomolecules are identical, or in the alternative, at least two biomolecules are different. Likewise, when a non-biomolecule is included, in one aspect all of the non-biomolecules are identical, and in another aspect at least two of the non-biomolecules are different. Combinations, wherein all biomolecules are identical and all non-biomolecules are identical are contemplated, along with mixtures wherein at least two biomolecules are combined with non-biomolecules that are all identical, all biomolecules are identical and at least two non-biomolecules are different, and at least two different biomolecules are combined with at least two different non-biomolecules.

A biomolecule and/or non-biomolecule as used herein will be understood to either be a structural biomolecule and/or structural non-biomolecule that are integral to the nanoconjugate structure, or a non-structural biomolecule and/or non-structural non-biomolecule that are not integral to the nanoconjugate structure. In some aspects wherein the biomolecule and/or non-biomolecule is non-structural, the biomolecule and/or non-biomolecule do not contain a crosslinking moiety. In this disclosure, non-structural biomolecules and non-structural non-biomolecules are referred to as additional agents.

Structure

The "structure" of a nanoconjugate is understood to be defined, in various aspects, by (i) the surface that was used in the manufacture of the nanoconjugates (ii) the type of biomolecules forming the nanoconjugate, and/or (iii) the degree and type of crosslinking between individual biomolecules on and/or around the surface.

In every aspect of the nanoconjugate provided, the biomolecules, with or without a non-biomolecule, are crosslinked. Crosslinking between biomolecules, with or without a non-biomolecule, is effected at a moiety on each biomolecule that can crosslink. If the nanoconjugate includes both biomolecules and non-biomolecules as structural components, the biomolecules and non-biomolecules are in some aspects conjugated together. It will be appreciated that some degree of intramolecular crosslinking may arise in formation of a nanoconjugate in instances wherein a biomolecule and/or non-biomolecule includes multiple crosslinking moieties.

In some aspects, a crosslinking moiety is a moiety that can become activated to crosslink. An activated moiety means that the crosslinking moiety present on a biomolecule, and/or non-biomolecule when present, is in a state that makes the moiety able to crosslink to another biomolecule, and/or non-biomolecule when present, that also contains a crosslinking moiety. The crosslinking moieties on a plurality of biomolecules and/or non-biomolecules can be the same for every biomolecule and/or non-biomolecules in the plurality, or at least two biomolecules and/or non-biomolecules in the plurality can contain different crosslinking moieties. A single biomolecule and/or non-biomolecule is also contemplated to comprise more than one crosslinking moiety, and those moieties can be the same or different.

In one aspect, the crosslinking moiety is located in the same position in each biomolecule, and/or non-biomolecule when present, which under certain conditions orients all of the biomolecules, and non-biomolecules, in the same direction.

In another aspect, the crosslinking moiety is located in different positions in the biomolecules, and/or non-biomolecules, which under certain conditions can provide mixed orientation of the biomolecules after crosslinking.

Shape

The shape of each nanoconjugate in the plurality is determined by the surface used in its production, and optionally by the biomolecules and/or non-biomolecules used in its production as well as well the degree and type of crosslinking between and among the biomolecules and/or non-biomolecules. The surface is in various aspects planar or three dimensional. Necessarily a planar surface will give rise to a planar nanoconjugate and a three dimensional surface will give rise to a three dimensional shape that mimics the three dimensional surface. When the surface is removed, a nanoconjugate formed with a planar surface will still be planar, and a nanoconjugate formed with a three dimensional surface will have the shape of the three dimensional surface and will be hollow.

Density

Depending on the degree of crosslinking and the amount of starting component, i.e., the biomolecules or mixture of biomolecules and no-biomolecules, in the preparative mixture, the nanoconjugates provided are contemplated to have varying densities. Thus, the surface is, in one aspect, completely covered with crosslinked biomolecules or crosslinked mixture of biomolecules and non-biomolecules, or in an alternative aspects, significantly covered with crosslinked biomolecules or crosslinked mixture of biomolecules and non-biomolecules, or sparsely covered with the crosslinked biomolecules or crosslinked mixture of biomolecules and non-biomolecules. The density of coverage of the surface is, in one aspect, even over the entire surface, or in the alternative, the density is uneven over the surface.

The density of the crosslinked biomolecules or crosslinked mixture of biomolecules and non-biomolecules of the nanoconjugate, and/or the evenness or lack of evenness of the density over the surface will determine the porosity of the nanoconjugate. In various aspects, the porosity determines the ability of the nanoconjugate to entrap additional, non-structural agents, as discussed below, in the interior of the nanoconjugate after the surface is removed.

Additional Agents

With regard to non-structural components, the nanoconjugates provided optionally include an additional agent which in one aspect as discussed above, is entrapped in the interior of a hollow nanoconjugate. Alternatively, the additional agent is embedded, or enmeshed, in the structural crosslinked biomolecules or mixture of crosslinked biomolecules and non-biomolecules or simply associated with one or both surfaces of structural crosslinked biomolecules or mixture of crosslinked biomolecule and non-biomolecules. It is contemplated that this additional agent is in one aspect covalently associated with the nanoconjugate, or in the alternative, non-covalently associated with the nanoconjugate. However, it is understood that the disclosure provides nanoconjugates wherein one or more additional agents are both covalently and non-covalently associated with the nanoconjugate. It will also be understood that non-covalent associations include hybridization (i.e., between polynucleotides), protein binding (i.e., between proteins which can bind) and/or hydrophobic interactions (i.e., between lipids and other agents that include a sufficiently hydrophobic domain). In other aspects, the additional agent is entrapped within the interior of a hollow nanoconjugate. When the nanoconjugate includes this additional agent, it is contemplated in one aspect that all of the additional agents are the same, and in other aspects, at least two of the additional agents are different.

Additional agents contemplated by the disclosure include without limitation a biomolecule, non-biomolecule, detectable marker, a coating, a polymeric agent, a contrast agent, an embolic agent, a short internal complementary polynucleotide (sicPN), a transcriptional regulator, a therapeutic agent, an antibiotic and a targeting moiety. These types of additional agents are discussed in detail below.

Biomolecules/Non-Biomolecules

Biomolecules, and non-biomolecules when present, with the ability to crosslink to other biomolecules and/or non-biomolecules, represent structural components of a nanoconjugate. As noted above, biomolecules, and non-biomolecules are also contemplated as being additional, non-structural agents of a nanoconjugate. As described, biomolecules include a polynucleotide, peptide, polypeptide, phospholipid, oligosaccharide, small molecule, therapeutic agent, contrast agent and combinations thereof.

Common to all structural biomolecules and/or non-biomolecules of the disclosure is that they comprise one or more crosslinking moieties. Non-structural biomolecules and/or non-biomolecules are contemplated that either do or do not possess crosslinking capability, but the non-structural biomolecules and/or non-biomolecules that do crosslink are not integral to maintaining the nanoconjugate structure.

The discussion that follow addresses biomolecules and/or non-biomolecules which are either structural or non-structural. As mentioned above, non-structural biomolecules and non-biomolecules as additional agents are also discussed in detail in a separate section below.

Polynucleotides

Polynucleotides contemplated by the present disclosure include DNA, RNA, modified forms and combinations thereof as defined herein. Accordingly, in some aspects, the nanoconjugate comprises DNA. In some embodiments, the DNA is double stranded, and in further embodiments the DNA is single stranded. In further aspects, the nanoconjugate comprises RNA, and in still further aspects the nanoconjugate comprises double stranded RNA, and in a specific embodiment, the double stranded RNA agent is a small interfering RNA (siRNA). The term "RNA" includes duplexes of two separate strands, as well as single stranded structures. Single stranded RNA also includes RNA with secondary structure. In one aspect, RNA having a hairpin loop in contemplated.

When a nanoconjugate comprise a plurality of structural polynucleotide biomolecules, the polynucleotide is, in some aspects, comprised of a sequence that is sufficiently complementary to a target sequence of a polynucleotide such that hybridization of the polynucleotide that is part of the nanoconjugate and the target polynucleotide takes place. The polynucleotide in various aspects is single stranded or double stranded, as long as the double stranded molecule also includes a single strand sequence that hybridizes to a single strand sequence of the target polynucleotide. In some aspects, hybridization of the polynucleotide that is part of the nanoconjugate can form a triplex structure with a double-stranded target polynucleotide. In another aspect, a triplex structure can be formed by hybridization of a double-stranded polynucleotide that is part of a nanoconjugate to a single-stranded target polynucleotide. Further description of triplex polynucleotide complexes is found in PCT/US2006/40124, which is incorporated herein by reference in its entirety.

In some aspects, polynucleotides contain a spacer as described herein. The spacer, in one aspect, comprises one or more crosslinking moieties that facilitate the crosslinking of one polynucleotide to another polynucleotide.

A "polynucleotide" is understood in the art to comprise individually polymerized nucleotide subunits. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleotides include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. No. 3,687,808, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Surfaces provided that are used to template a polynucleotide, or a modified form thereof, generally comprise a polynucleotide from about 5 nucleotides to about 100 nucleotides in length. More specifically, nanoconjugates comprise polynucleotides that are about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

Polynucleotides, as defined herein, also includes aptamers. The production and use of aptamers is known to those of ordinary skill in the art. In general, aptamers are nucleic acid or peptide binding species capable of tightly binding to and discreetly distinguishing target ligands [Yan et al., RNA Biol. 6(3) 316-320 (2009), incorporated by reference herein in its entirety]. Aptamers, in some embodiments, may be obtained by a technique called the systematic evolution of ligands by exponential enrichment (SELEX) process [Tuerk et al., Science 249:505-10 (1990), U.S. Pat. No. 5,270,163, and U.S. Pat. No. 5,637,459, each of which is incorporated herein by reference in their entirety]. General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyarnaya Biologiya, Vol. 34, No. 6, 2000, pp. 1097-1113, which is incorporated herein by reference in its entirety. In various aspects, an aptamer is between 10-100 nucleotides in length.

Spacers

In certain aspects, nanoconjugates are contemplated which include those wherein a nanoconjugate comprises a biomolecule which further comprises a spacer. The spacer in various aspects comprises one or more crosslinking moieties as described below.

"Spacer" as used herein means a moiety that serves to contain one or more crosslinking moieties, or, in some aspects wherein the nanoconjugate comprises a nanoparticle, increase distance between the nanoparticle and the biomolecule, or to increase distance between individual biomolecules when attached to the nanoparticle in multiple copies. In aspects of the disclosure wherein a nanoconjugate is used for a biological activity, it is contemplated that the spacer does not directly participate in the activity of the biomolecule to which it is attached.

Thus, in some aspects, the spacer is contemplated herein to facilitate crosslinking via one or more crosslinking moieties. Spacers are additionally contemplated, in various aspects, as being located between individual biomolecules in tandem, whether the biomolecules have the same sequence or have different sequences. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, or combinations thereof.

In instances wherein the spacer is a polynucleotide, the length of the spacer in various embodiments at least about 5 nucleotides, at least about 10 nucleotides, 10-30 nucleotides, or even greater than 30 nucleotides. The spacer may have any sequence which does not interfere with the ability of the polynucleotides to become bound to the nanoparticles or to the target polynucleotide. The spacers should not have sequences complementary to each other or to that of the polynucleotides, but may be all or in part complementary to the target polynucleotide. In certain aspects, the bases of the polynucleotide spacer are all adenines, all thymines, all cytidines, all guanines, all uracils, or all some other modified base.

Modified Polynucleotides

As discussed above, modified polynucleotides are contemplated for use in producing nanoconjugates, and are template by a surface. In various aspects, a polynucleotide templated on a surface is completely modified or partially modified. Thus, in various aspects, one or more, or all, sugar and/or one or more or all internucleotide linkages of the nucleotide units in the polynucleotide are replaced with "non-naturally occurring" groups.

In one aspect, this embodiment contemplates a peptide nucleic acid (PNA). In PNA compounds, the sugar-backbone of a polynucleotide is replaced with an amide containing backbone. See, for example U.S. Pat. Nos. 5,539,082; 5,714, 331; and 5,719,262, and Nielsen et al., Science, 1991, 254, 1497-1500, the disclosures of which are herein incorporated by reference.

Other linkages between nucleotides and unnatural nucleotides contemplated for the disclosed polynucleotides include those described in U.S. Pat. Nos. 4,981,957; 5,118, 800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; U.S. Patent Publication No. 20040219565; International Patent Publication Nos. WO 98/39352 and WO 99/14226; Mesmaeker et. al., Current Opinion in Structural Biology 5:343-355 (1995) and Susan M. Freier and Karl-Heinz Altmann, Nucleic Acids Research, 25:4429-4443 (1997), the disclosures of which are incorporated herein by reference.

Specific examples of polynucleotides include those containing modified backbones or non-natural internucleoside linkages. Polynucleotides having modified backbones include those that retain a phosphorus atom in the backbone and those that do not have a phosphorus atom in the backbone. Modified polynucleotides that do not have a phosphorus atom in their internucleoside backbone are considered to be within the meaning of "polynucleotide."

Modified polynucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated.

Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts. In still other embodiments, polynucleotides are provided with phosphorothioate backbones and oligonucleosides with heteroatom backbones, and including —CH2-NH—O—CH2-, —CH2-N(CH3)-O—CH2-, —CH2-O—N(CH3)-CH2-, —CH2-N(CH3)-N(CH3)—CH2- and —O—N(CH3)-CH2-CH2- described in U.S. Pat. Nos. 5,489,677, and 5,602,240. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In various forms, the linkage between two successive monomers in the polynucleotide consists of 2 to 4, desirably 3, groups/atoms selected from —CH2-, —O—, —S—, —NRH—, >C=O, >C=NRH, >C=S, —Si(R")2-, —SO—, —S(O)2-, —P(O)2-, —PO(BH3)-, —P(O,S)—, —P(S)2-, —PO(R")—, —PO(OCH3)-, and —PO(NHRH)—, where RH is selected from hydrogen and C1-4-alkyl, and R" is selected from C1-6-alkyl and phenyl. Illustrative examples of such linkages are —CH2-CH2-CH2-, —CH2-CO—CH2-, —CH2-CHOH—CH2-, —O—CH2-O—, —O—CH2-CH2-, —O—CH2-CH=(including R5 when used as a linkage to a succeeding monomer), —CH2-CH2-O—, —NRH—CH2-CH2-, —CH2-CH2-NRH—, —CH2-NRH—CH2-, —O—CH2-CH2-NRH—, —NRH—CO—O—, —NRH—CO—NRH—, —NRH—CS—NRH—, —NRH—C(=NRH)—NRH—, —NRH—CO—CH2-NRH—O—CO—O—, —O—CO—CH2-O—, —O—CH2-CO—O—, —CH2-CO—NRH—, —O—CO—NRH—, —NRH—CO—CH2-, —O—CH2-CO—NRH—, —O—CH2-CH2-NRH—, —CH=N—O—, —CH2-NRH—O—, —CH2-O—N=(including R5 when used as a linkage to a succeeding monomer), —CH2-O—NRH—, —CO—NRH—CH2-, —CH2-NRH—O—, —CH2-NRH—CO—, —O—NRH—CH2-, —O—NRH, —O—CH2-S—, —S—CH2-O—, —CH2-CH2-S—, —O—CH2-CH2-S—, —S—CH2-CH=(including R5 when used as a linkage to a succeeding monomer), —S—CH2-CH2-, —S—CH2-CH2-O—, —S—CH2-CH2-S—, —CH2-S—CH2-, —CH2-SO—CH2-, —CH2-SO2-CH2-, —O—SO—O—, —O—S(O)2-O—, —O—S(O)2-CH2-, —O—S(O)2-NRH—, —NRH—S(O)2-CH2-; —O—S(O)2-CH2-, —O—P(O)2-O—, —O—P(O,S)—O—, —O—P(S)2-O—, —S—P(O)2-O—, —S—P (O,S)—O—, —S—P(S)2-O—, —O—P(O)2-S—, —O—P(O,S)—S—, —O—P(S)2-S—, —S—P(O)2-S—, —S—P(O,S)—S—, —S—P(S)2-S—, —O—PO(R")—O—, —O—PO(OCH3)-O—, —O—PO(O CH2CH3)-O—, —O—PO(O CH2CH2S—R)—O—, —O—PO(BH3)-O—, —O—PO(NHRN)—O—, —O—P(O)2-NRH H—, —NRH—P(O)2-O—, —O—P(O,NRH)—O—, —CH2-P(O)2-O—, —O—P(O)2-CH2-, and —O—Si(R")2-O—; among which —CH2-CO—NRH—, —CH2-NRH—O—, —S—CH2-O—, —O—P(O)2-O—O—P(=O,S)—O—, —O—P(S)2-O—, —NRH P(O)2-O—, —O—P(O,NRH)—O—, —O—PO(R")—O—, —O—PO(CH3)-O—, and —O—PO(NHRN)—O—, where RH is selected form hydrogen and C1-4-alkyl, and R" is selected from C1-6-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. Patent Application No. 20040219565, the disclosure of which is incorporated by reference herein in its entirety.

Modified polynucleotides may also contain one or more substituted sugar moieties. In certain aspects, polynucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Other embodiments include O[(CH2)nO]mCH3, O(CH2)nOCH3, O(CH2)nNH2, O(CH2)nCH3, O(CH2)nONH2, and O(CH2)nON[(CH2)nCH3]2, where n and m are from 1 to about 10. Other polynucleotides comprise one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In one aspect, a modification includes 2'-methoxyethoxy (2'-O—CH2CH2OCH3, also known as 2'-O-(2-methoxyethyl) or 2'-MOE) (Martin et al., 1995, Hely. Chim. Acta, 78: 486-504) i.e., an alkoxyalkoxy group. Other modifications include 2'-dimethylaminooxyethoxy, i.e., a O(CH2)2ON(CH3)2 group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH2-O—CH2-N(CH3)2.

Still other modifications include 2'-methoxy (2'-O—CH3), 2'-aminopropoxy (2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. In one aspect, a 2'-arabino modification is 2'-F. Similar modifications may also be made at other positions on the polynucleotide, for example, at the 3' position of the sugar on the 3' terminal nucleotide or in 2'-5' linked polynucleotides and the 5' position of 5' terminal nucleotide. Polynucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265;

5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects a methylene (—CH2-)n group bridging the 2' oxygen atom and the 4' carbon atom wherein n is 1 or 2. LNAs and preparation thereof are described in WO 98/39352 and WO 99/14226, the disclosures of which are incorporated herein by reference.

Polynucleotide Features

Each nanoconjugate provided comprises a plurality of biomolecules, and in various aspects, the biomolecules are polynucleotides. As a result, each nanoconjugate has the ability to bind to a plurality of target polynucleotides having a sufficiently complementary sequence. For example, if a specific polynucleotide is targeted, a single nanoconjugate has the ability to bind to multiple copies of the same molecule. In one aspect, methods are provided wherein the nanoconjugate comprises identical polynucleotides, i.e., each polynucleotide has the same length and the same sequence. In other aspects, the nanoconjugate comprises two or more polynucleotides which are not identical, i.e., at least one of the polynucleotides of the nanoconjugate differ from at least one other polynucleotide of the nanoconjugate in that it has a different length and/or a different sequence. In aspects wherein a nanoconjugate comprises different polynucleotides, these different polynucleotides bind to the same single target polynucleotide but at different locations, or bind to different target polynucleotides which encode different gene products. Accordingly, in various aspects, a single nanoconjugate may be used in a method to inhibit expression of more than one gene product. Polynucleotides are thus used to target specific polynucleotides, whether at one or more specific regions in the target polynucleotide, or over the entire length of the target polynucleotide as the need may be to effect a desired level of inhibition of gene expression.

Accordingly, in one aspect, the polynucleotides are designed with knowledge of the target sequence. Alternatively, a polynucleotide in a nanoconjugate need not hybridize to a target biomolecule in order to achieve a desired effect as described herein. Regardless, methods of making polynucleotides of a predetermined sequence are well-known. See, for example, Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are contemplated for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

Alternatively, polynucleotides are selected from a library. Preparation of libraries of this type is well known in the art. See, for example, Oligonucleotide libraries: United States Patent Application 20050214782, published Sep. 29, 2005.

Polynucleotides contemplated for production of a nanoconjugate include, in one aspect, those which modulate expression of a gene product expressed from a target polynucleotide. Accordingly, antisense polynucleotides which hybridize to a target polynucleotide and inhibit translation, siRNA polynucleotides which hybridize to a target polynucleotide and initiate an RNAse activity (for example RNAse H), triple helix forming polynucleotides which hybridize to double-stranded polynucleotides and inhibit transcription, and ribozymes which hybridize to a target polynucleotide and inhibit translation, are contemplated.

In some aspects, a polynucleotide-based nanoconjugate allows for efficient uptake of the nanoconjugate. In various aspects, the polynucleotide comprises a nucleotide sequence that allows increased uptake efficiency of the nanoconjugate. As used herein, "efficiency" refers to the number or rate of uptake of nanoconjugates in/by a cell. Because the process of nanoconjugates entering and exiting a cell is a dynamic one, efficiency can be increased by taking up more nanoconjugates or by retaining those nanoconjugates that enter the cell for a longer period of time. Similarly, efficiency can be decreased by taking up fewer nanoconjugates or by retaining those nanoconjugates that enter the cell for a shorter period of time.

Thus, the nucleotide sequence can be any nucleotide sequence that is desired may be selected for, in various aspects, increasing or decreasing cellular uptake of a nanoconjugate or gene regulation. The nucleotide sequence, in some aspects, comprises a homopolymeric sequence which affects the efficiency with which the nanoparticle to which the polynucleotide is attached is taken up by a cell. Accordingly, the homopolymeric sequence increases or decreases the efficiency. It is also contemplated that, in various aspects, the nucleotide sequence is a combination of nucleobases, such that it is not strictly a homopolymeric sequence. For example and without limitation, in various aspects, the nucleotide sequence comprises alternating thymidine and uridine residues, two thymidines followed by two uridines or any combination that affects increased uptake is contemplated by the disclosure. In some aspects, the nucleotide sequence affecting uptake efficiency is included as a domain in a polynucleotide comprising additional sequence. This "domain" would serve to function as the feature affecting uptake efficiency, while the additional nucleotide sequence would serve to function, for example and without limitation, to regulate gene expression. In various aspects, the domain in the polynucleotide can be in either a proximal, distal, or center location relative to the nanoconjugate. It is also contemplated that a polynucleotide comprises more than one domain.

The homopolymeric sequence, in some embodiments, increases the efficiency of uptake of the nanoconjugate by a cell. In some aspects, the homopolymeric sequence comprises a sequence of thymidine residues (polyT) or uridine residues (polyU). In further aspects, the polyT or polyU sequence comprises two thymidines or uridines. In various aspects, the polyT or polyU sequence comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 125, about 150, about 175, about 200, about 250, about 300, about 350, about 400, about 450, about 500 or more thymidine or uridine residues.

In some embodiments, it is contemplated that a nanoconjugate comprising a polynucleotide that comprises a homopolymeric sequence is taken up by a cell with greater efficiency than a nanoconjugate comprising the same polynucleotide but lacking the homopolymeric sequence. In various aspects, a nanoconjugate comprising a polynucleotide that comprises a homopolymeric sequence is taken up by a cell about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold or higher, more efficiently than a nanoconjugate comprising the same polynucleotide but lacking the homopolymeric sequence.

In other aspects, the domain is a phosphate polymer (C3 residue). In some aspects, the domain comprises a phosphate polymer (C3 residue) that is comprised of two phosphates. In various aspects, the C3 residue comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 125, about 150, about 175, about 200, about 250, about 300, about 350, about 400, about 450, about 500 or more phosphates.

In some embodiments, it is contemplated that a nanoconjugate comprising a polynucleotide which comprises a domain is taken up by a cell with lower efficiency than a nanoconjugate comprising the same polynucleotide but lacking the domain. In various aspects, a nanoconjugate comprising a polynucleotide which comprises a domain is taken up by a cell about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold or higher, less efficiently than a nanoconjugate comprising the same polynucleotide but lacking the domain.

As used herein, a "conjugation site" is understood to mean a site on a polynucleotide to which a contrast agent is attached. In certain aspects, the disclosure also provides one or more polynucleotides that are part of the nanoconjugate do not comprise a conjugation site while one or more polynucleotides that are part of the same nanoconjugate do comprise a conjugation site. Conjugation of a contrast agent to a nanoconjugate through a conjugation site is generally described in PCT/US2010/44844, which is incorporated herein by reference in its entirety. The disclosure provides, in one aspect, a nanoconjugate comprising a polynucleotide wherein the polynucleotide comprises one to about ten conjugation sites. In another aspect, the polynucleotide comprises five conjugation sites. In general, for a nucleotide, both its backbone (phosphate group) and nucleobase can be modified. Accordingly, the present disclosure contemplates that there are 2n conjugation sites, where n=length of the polynucleotide template. In related aspects, it is contemplated that the composition comprises a nanoconjugate comprising a plurality of polynucleotides. In some aspects, the plurality of polynucleotides comprises at least one polynucleotide to which contrast agents are associated through one or more conjugation sites, as well as at least one polynucleotide that has gene regulatory activity as described herein.

Accordingly, in some embodiments, it is contemplated that one or more polynucleotides that are part of the nanoconjugate is not conjugated to a contrast agent while one or more polynucleotides that are part of the same nanoconjugate are conjugated to a contrast agent.

The present disclosure also provides compositions comprising a nanoconjugate, wherein the nanoconjugate comprises polynucleotides, and further comprising a transcriptional regulator, wherein the transcriptional regulator induces transcription of a target polynucleotide in a target cell.

Polynucleotide Length

Nanoconjugates in the compositions and methods provided comprise, in some embodiments, a polynucleotide, or modified form thereof, which is from about 5 to about 100 nucleotides in length. Methods are also contemplated wherein the polynucleotide is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 or more nucleotides in length are contemplated.

Polynucleotide Copies—Same/Different Sequences

Nanoconjugates are provided which include those wherein a single sequence in a single polynucleotide or multiple copies of the single sequence in a single polynucleotide is part of a nanoconjugate. Thus, in various aspects, a polynucleotide is contemplated with multiple copies of a single sequence are in tandem, for example, two, three, four, five, six, seven eight, nine, ten or more tandem repeats.

Alternatively, the nanoconjugate includes at least two polynucleotides having different sequences. As above, the different polynucleotide sequences are in various aspects arranged in tandem (i.e., on a single polynucleotide) and/or in multiple copies (i.e., on at least two polynucleotides). In methods wherein polynucleotides having different sequences are part of the nanoconjugate, aspects of the disclosure include those wherein the different polynucleotide sequences hybridize to different regions on the same polynucleotide. Alternatively, the different polynucleotide sequences hybridize to different polynucleotides.

Polypeptides

As used herein a "polypeptide" refers to a polymer comprised of amino acid residues. In some aspects of the disclosure, a nanoconjugate comprises a polypeptide as described herein. Polypeptides are understood in the art and include without limitation an antibody, an enzyme, a structural polypeptide and a hormone. In related aspects, the nanoconjugate comprising a polypeptide recognizes and associates with a target molecule and enables detection of the target molecule. A polypeptide of the disclosure can be a biomolecule or an additional agent, each as described herein.

Polypeptides of the present disclosure may be either naturally occurring or non-naturally occurring. Polypeptides optionally include a spacer as described herein above. As described above, a structural; polypeptide has a crosslinking moiety through which the polypeptide is able to crosslink with one or more other biomolecules in the nanoconjugate preparative process. When a polypeptide is an additional agent, the polypeptide need not, but may, include a crosslinking moiety. When the additional polypeptide agent includes a crosslinking moiety, the polypeptide generally does not crosslink to the nanoconjugate in a manner that is required for the nanoconjugate to maintain structural integrity.

Naturally Occurring Polypeptides

Naturally occurring polypeptides include without limitation biologically active polypeptides (including antibodies)

that exist in nature or can be produced in a form that is found in nature by, for example, chemical synthesis or recombinant expression techniques. Naturally occurring polypeptides also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Structural polypeptides contemplated by the disclosure include without limitation actin, tubulin, collagen, elastin, myosin, kinesin and dynein.

Non-Naturally Occurring Polypeptides

Non-naturally occurring polypeptides contemplated by the present disclosure include but are not limited to synthetic polypeptides, as well as fragments, analogs and variants of naturally occurring or non-naturally occurring polypeptides as defined herein. Non-naturally occurring polypeptides also include proteins or protein substances that have D-amino acids, modified, derivatized, or non-naturally occurring amino acids in the D- or L-configuration and/or peptidomimetic units as part of their structure. The term "protein" typically refers to large polypeptides. The term "peptide" typically refers to short polypeptides.

Non-naturally occurring polypeptides are prepared, for example, using an automated polypeptide synthesizer or, alternatively, using recombinant expression techniques using a modified polynucleotide which encodes the desired polypeptide.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, polypeptides are modified by glycosylation, pegylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest.

This group of biomolecules includes antibodies along with fragments and derivatives thereof, including but not limited to Fab' fragments, F(ab)2 fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

Phospholipids

Also contemplated by the disclosure are nanoconjugates comprising phospholipids. As discussed above for other biomolecules, a phospholipid biomolecule includes, in certain aspects, an optional spacer component. A phospholipid that is a structural biomolecule includes a crosslinking moiety as described above for other biomolecules, through which the pohospholipid is able to crosslink to other biomolecules, A phospholipid that is a non-structural biomolecule may, but need not, include a crosslinking moiety.

Lipid and phospholipid-derived hormones are contemplated as structural and non-structural biomolecules, and these compounds derive from lipids such as linoleic acid and arachidonic acid and phospholipids. The main classes are the steroid hormones that derive from cholesterol and the eicosanoids.

In one specific embodiment, a synthetic high density lipoprotein (HDL) nanoconjugate is be constructed by modifying a gold nanoparticle with a dense shell of phospholipids and APO1A. HDL is a dynamic serum nanoconjugate protective against the development of atherosclerosis and resultant illnesses such as heart disease and stroke. Like naturally-occurring HDL, this synthetic construct is capable of binding cholesterol in its hydrophobic phospholipid shell. It is the dense polyvalent arrangement of biological ligands on the surface of inorganic nanoparticles that imparts their unique ability to interact with biological systems, regardless of their core material.

Metal Complexes

A metal complex as defined herein can be a structural non-biomolecule and/or an additional agent, each as described herein. A metal complex optional include a spacer as described herein above.

A "metal complex" as used herein refers to a metal and includes without limitation a platinum compound as described herein, germanium(IV), titanium(IV), tin(IV), ruthenium(III), gold(III), and copper(II). If a metal complex is a structural non-biomolecule, it necessarily will include a crosslinking moiety through which is will crosslink to other biomolecules and/or non-biomolecules. A metal complex that is an additional agent, may, but need not, include a crosslinking moiety.

Oligosaccharides

Oligosaccharides are contemplated by the disclosure to be a structural biomolecule and/or an additional agent, each as described herein.

Oligosaccharides include any carbohydrates comprising between about two to about ten monosaccharides or more connected by either an alpha- or beta-glycosidic link. Oligosaccharides are found throughout nature in both the free and bound form. As discussed above for other biomolecules, a phospholipid biomolecule includes, in certain aspects, an optional spacer component. An oligosaccharide that is a structural biomolecule includes a crosslinking moiety as described above for other biomolecules, through which the oligosaccharide is able to crosslink to other biomolecules, A oligosaccharide that is a non-structural biomolecule may, but need not, include a crosslinking moiety. Oligosaccharides optionally include a spacer as described herein above.

Other Non-Biomolecules

A non-biomolecule as used herein is selected from the group consisting of a diluent molecule, a metal complex as described above and any non-carbon containing molecule known in the art.

Nanoconjugate Structure

As described herein, the structure of each nanoconjugate is defined by (i) the surface that was used in the manufacture of the nanoconjugates (ii) the type of biomolecules forming the nanoconjugate, and (iii) the degree and type of crosslinking between individual biomolecules on and/or around the surface. Also as discussed herein, in every aspect of the nanoconjugate provided, the biomolecules, with or without a non-biomolecule, are crosslinked. The crosslinking is effected through the use of one or more crosslinking moieties.

Crosslinking

Crosslinking moieties contemplated by the disclosure include but are not limited to an amine, amide, alcohol, ester, aldehyde, ketone, thiol, disulfide, carboxylic acid, phenol, imidazole, hydrazine, hydrazone, azide and an alkyne. Any crosslinking moiety can be used, so long as it can be attached to a biomolecule and/or non-biomolecule by a method known to one of skill in the art.

In various embodiments, an alkyne is associated with a biomolecule through a degradable moiety. For example and without limitation, the alkyne in various aspects is associated with a biomolecule through an acid-labile moiety that is degraded upon entry into an endosome inside a cell.

In some aspects, the surface with which a biomolecule is associated acts as a catalyst for the crosslinking moieties. Under appropriate conditions, contact of a crosslinking moiety with the surface will activate the crosslinking moiety, thereby initiating sometimes spontaneous crosslinking between structural biomolecules and/or non-biomolecules. In one specific aspect, the crosslinking moiety is an alkyne and the surface is comprised of gold. In this aspect, and as described herein, the gold surface acts as a catalyst to activate an alkyne crosslinking moiety, thus allowing the crosslink to form between a biomolecule comprising an alkyne crosslinking moiety to another biomolecule comprising an alkyne crosslinking moiety.

Production methods are also contemplated wherein a chemical is used to effect the crosslinking between biomolecules. Chemicals contemplated for use in crosslinking biomolecules are discussed below.

Polynucleotides contemplated for use in the methods include those associated with a nanoconjugate through any means. Regardless of the means by which the polynucleotide is associated with the nanoconjugate, association in various aspects is effected through a 5' linkage, a 3' linkage, some type of internal linkage, or any combination of these attachments and depends on the location of the crosslinking moiety in the polynucleotide. By way of example, a crosslinking moiety on the 3' end of a polynucleotide means that the polynucleotide will associate with the nanoconjugate at its 3' end.

In various aspects, the crosslinking moiety is located in a spacer. A spacer is described herein above, and it is contemplated that a nucleotide in the spacer comprises a crosslinking moiety. In further aspects, a nucleotide in the spacer comprises more than one crosslinking moiety, and the more than one crosslinking moieties are either the same or different. In addition, each nucleotide in a spacer can comprise one or more crosslinking moieties, which can either be the same or different.

In some embodiments, the polynucleotide does not comprise a spacer. In these aspects, the polynucleotide comprises one or more crosslinking moieties along its length. The crosslinking moieties can be the same or different, and each nucleotide in the polynucleotide can comprise one or more crosslinking moieties, and these too can either be the same or different.

In one aspect, a polynucleotide comprises one crosslinking moiety, which can optionally be in a spacer portion of the polynucleotide if a spacer is present. If a polynucleotide consists of one crosslinking moiety, then it is contemplated that the polynucleotide is an additional agent that is crosslinked to a nanoconjugate.

In further aspects, a polynucleotide comprises from about 1 to about 500 crosslinking moieties, or from about 1 to about 100, or from about 5 to about 50, or from about 10 to about 30, or from about 10 to about 20 crosslinking moieties. In various embodiments, the polynucleotide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more crosslinking moieties. In aspects wherein the spacer comprises more than one crosslinking moiety, the moieties can all be the same or they can be different, and any combination of crosslinking moieties may be used.

In one aspect, the crosslinking moiety is located in the same position in each polynucleotide, which under certain conditions orients all of the polynucleotides in the same direction. In some aspects, the direction is such that the 5' and 3' ends of a polynucleotide are diametrically opposed to each other. In these aspects, the spacer end will be more "proximal" with respect to the nanoconjugate surface, while the opposite end will be more "distal" with respect to the nanoconjugate surface. With respect to "proximal" and "distal" and their relationship to the nanoconjugate surface, it will be understood that the location is determined when the surface is present, and prior to its optional at least partial removal. The orienting of polynucleotides in the same direction in a nanoconjugate is useful, for example and without limitation, when a polynucleotide is to be hybridized to a target biomolecule since the nanoconjugate structure provides a polyvalent network of polynucleotides that are positioned to recognize and associate with the target biomolecule.

In another aspect, the crosslinking moiety is located in different positions in the polynucleotides, which under certain conditions can provide mixed orientation of the polynucleotides after crosslinking.

In some embodiments, a biomolecule and/or non-biomolecule comprising a crosslinking moiety is attached to a nanoparticle, wherein the attachment is displaceable. Thus, in one aspect, a crosslinking moiety that associates with a surface can remain in association with the surface, or it can be displaced from the surface through reaction with another crosslinking moiety that is present on another biomolecule and/or non-biomolecule. As previously described, in some embodiments the association of a biomolecule and/or non-biomolecule comprising a crosslinking moiety with a surface results in the crosslinking of the biomolecule and/or non-biomolecule to another biomolecule and/or non-biomolecule that is in association with the surface.

Nanoparticles Providing Shape

The shape of each nanoconjugate in the plurality is determined in part by the surface used in its production, and in part by the biomolecules and/or non-biomolecules used in its production. The surface is in various aspects planar or three dimensional. Thus, in various aspects, the surface is a nanoparticle.

In general, nanoparticles contemplated include any compound or substance with a high loading capacity for a biomolecule to effect the production of a nanoconjugate as described herein, including for example and without limitation, a metal, a semiconductor, and an insulator particle compositions, and a dendrimer (organic versus inorganic).

Thus, nanoparticles are contemplated which comprise a variety of inorganic materials including, but not limited to, metals, semi-conductor materials or ceramics as described in US patent application No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles.

In one embodiment, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, iron, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, TiO2, Sn, SnO2, Si, SiO2, Fe, Fe+4, Fe3O4, Fe2O3, Ag, Cu, Ni, Al, steel, cobalt-chrome alloys, Cd, titanium alloys, AgI, AgBr, HgI2, PbS, PbSe, ZnTe, CdTe, In2S3, In2Se3, Cd3P2, Cd3As2, InAs, and GaAs. Methods of making ZnS, ZnO, TiO2, AgI, AgBr, HgI2, PbS, PbSe, ZnTe, CdTe, In2S3, In2Se3, Cd3P2, Cd3As2, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshaysky, et al., J. Am. Chem. Soc., 112, 9438 (1990); Ushida et al., J. Phys. Chem., 95, 5382 (1992).

In practice, compositions and methods are provided using any suitable nanoparticle suitable for use in methods to the extent they do not interfere with complex formation. The size, shape and chemical composition of the particles contribute to the properties of the resulting nanoconjugate. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles, aggregate particles, isotropic (such as spherical particles) and anisotropic particles (such as non-spherical rods, tetrahedral, prisms) and core-shell particles such as the ones described in U.S. patent application Ser. No. 10/034, 451, filed Dec. 28, 2002 and International application no. PCT/US01/50825, filed Dec. 28, 2002, the disclosures of which are incorporated by reference in their entirety.

Methods of making metal, semiconductor and magnetic nanoparticles are well-known in the art. See, for example, Schmid, G. (ed.) Clusters and Colloids (V C H, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers)

Also as described in US patent application No 20030147966, nanoparticles comprising materials described herein are available commercially from, for example, Ted Pella, Inc. (gold), Amersham Corporation (gold) and Nanoprobes, Inc. (gold), or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in US patent application No 20030147966, nanoparticles contemplated are produced using HAuC14 and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticle Size

In various aspects, methods provided include those utilizing nanoparticles which range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or amount surface area that can be derivatized as described herein.

Biomolecule Density

Nanoconjugates as provided herein have a density of the biomolecules on the surface of the nanoconjugate that is, in various aspects, sufficient to result in cooperative behavior between nanoconjugates and between biomolecules on a single nanoconjugate. In another aspect, the cooperative behavior between the nanoconjugates increases the resistance of the biomolecule to degradation, and provides a sharp melting transition relative to biomolecules that are not part of a nanoconjugate. In one aspect, the uptake of nanoconjugates by a cell is influenced by the density of polynucleotides associated with the nanoparticle. As described in PCT/US2008/65366, incorporated herein by reference in its entirety, a higher density of polynucleotides on the surface of a polynucleotide functionalized nanoparticle is associated with an increased uptake of nanoparticles by a cell. This aspect is likewise contemplated to be a property of nanoconjugates, wherein a higher density of biomolecules that make up a nanoconjugate is associated with an increased uptake of a nanoconjugate by a cell.

A surface density adequate to make the nanoconjugates stable and the conditions necessary to obtain it for a desired combination of nanoconjugates and biomolecules can be determined empirically. Broadly, the smaller the biomolecule and/or non-biomolecule that is used, the higher the surface density of that biomolecule and/or non-biomolecule can be. Generally, a surface density of at least 2 pmol/cm$^2$ will be adequate to provide stable nanoconjugate-compositions. In some aspects, the surface density is at least 15 pmol/cm$^2$. Methods are also provided wherein the biomolecule is present in a nanoconjugate at a surface density of at least 2 pmol/cm2, at least 3 pmol/cm2, at least 4 pmol/cm2, at least 5 pmol/cm2, at least 6 pmol/cm2, at least 7 pmol/cm2, at least 8 pmol/cm2, at least 9 pmol/cm2, at least 10 pmol/cm2, at least about 15 pmol/cm2, at least about 20 pmol/cm2, at least about 25 pmol/cm2, at least about 30 pmol/cm2, at least about 35 pmol/cm2, at least about 40 pmol/cm2, at least about 45 pmol/cm2, at least about 50 pmol/cm2, at least about 55 pmol/cm2, at least about 60 pmol/cm2, at least about 65 pmol/cm2, at least about 70 pmol/cm2, at least about 75 pmol/cm2, at least about 80 pmol/cm2, at least about 85 pmol/cm2, at least about 90 pmol/cm2, at least about 95 pmol/cm2, at least about 100 pmol/cm2, at least about 125 pmol/cm2, at least about 150 pmol/cm2, at least about 175 pmol/cm2, at least about 200 pmol/cm2, at least about 250 pmol/cm2, at least about 300 pmol/cm2, at least about 350 pmol/cm2, at least about 400 pmol/cm2, at least about 450 pmol/cm2, at least about 500 pmol/cm2, at least about 550 pmol/cm2, at least about 600 pmol/cm2, at least about 650 pmol/cm2, at least about 700 pmol/cm2, at least about 750 pmol/cm2, at least about 800 pmol/cm2, at least about 850 pmol/cm2, at least about 900 pmol/cm2, at least about 950 pmol/cm2, at least about 1000 pmol/cm2 or more.

It is contemplated that the density of polynucleotides in a nanoconjugate modulates specific biomolecule and/or non-biomolecule interactions with the polynucleotide on the surface and/or with the nanoconjugate itself. Under various conditions, some polypeptides may be prohibited from interacting with polynucleotides that are part of a nanoconjugate based on steric hindrance caused by the density of polynucleotides. In aspects where interaction of polynucleotides with a biomolecule and/or non-biomolecule that are otherwise precluded by steric hindrance is desirable, the density of polynucleotides in the nanoconjugate is decreased to allow the biomolecule and/or non-biomolecule to interact with the polynucleotide.

Nanoparticles of larger diameter are, in some aspects, contemplated to be templated with a greater number of polynucleotides [Hurst et al., Analytical Chemistry 78(24): 8313-8318 (2006)] during nanoconjugate production. In some aspects, therefore, the number of polynucleotides used in the production of a nanoconjugate is from about 10 to about 25,000 polynucleotides per nanoconjugate. In further aspects, the number of polynucleotides used in the production of a nanoconjugate is from about 50 to about 10,000 polynucleotides per nanoconjugate, and in still further aspects the number of polynucleotides used in the production of a nanoconjugate is from about 200 to about 5,000 polynucleotides per nanoconjugate. In various aspects, the number of polynucleotides used in the production of a nanoconjugate is about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 525, about 530, about 535, about 540, about 545, about 550, about 555, about 560, about 565, about 570, about 575, about 580, about 585, about 590, about 595, about 600, about 605, about 610, about 615, about 620, about 625, about 630, about 635, about 640, about 645, about 650, about 655, about 660, about 665, about 670, about 675, about 680, about 685, about 690, about 695, about 700, about 705, about 710, about 715, about 720, about 725, about 730, about 735, about 740, about 745, about 750, about 755, about 760, about 765, about 770, about 775, about 780, about 785, about 790, about 795, about 800, about 805, about 810, about 815, about 820, about 825, about 830, about 835, about 840, about 845, about 850, about 855, about 860, about 865, about 870, about 875, about 880, about 885, about 890, about 895, about 900, about 905, about 910, about 915, about 920, about 925, about 930, about 935, about 940, about 945, about 950, about 955, about 960, about 965, about 970, about 975, about 980, about 985, about 990, about 995, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, about 5100, about 5200, about 5300, about 5400, about 5500, about 5600, about 5700, about 5800, about 5900, about 6000, about 6100, about 6200, about 6300, about 6400, about 6500, about 6600, about 6700, about 6800, about 6900, about 7000, about 7100, about 7200, about 7300, about 7400, about 7500, about 7600, about 7700, about 7800, about 7900, about 8000, about 8100, about 8200, about 8300, about 8400, about 8500, about 8600, about 8700, about 8800, about 8900, about 9000, about 9100, about 9200, about 9300, about 9400, about 9500, about 9600, about 9700, about 9800, about 9900, about 10000, about 10100, about 10200, about 10300, about 10400, about 10500, about 10600, about 10700, about 10800, about 10900, about 11000, about 11100, about 11200, about 11300, about 11400, about 11500, about 11600, about 11700, about 11800, about 11900, about 12000, about 12100, about 12200, about 12300, about 12400, about 12500, about 12600, about 12700, about 12800, about 12900, about 13000, about 13100, about 13200, about 13300, about 13400, about 13500, about 13600, about 13700, about 13800, about 13900, about 14000, about 14100, about 14200, about 14300, about 14400, about 14500, about 14600, about 14700, about 14800, about 14900, about 15000, about 15100, about 15200, about 15300, about 15400, about 15500, about 15600, about 15700, about 15800, about 15900, about 16000, about 16100, about 16200, about 16300, about 16400, about 16500, about 16600, about 16700, about 16800, about 16900, about 17000, about 17100, about 17200, about 17300, about 17400, about 17500, about 17600, about 17700, about 17800, about 17900, about 18000, about 18100, about 18200, about 18300, about 18400, about 18500, about 18600, about 18700, about 18800, about 18900, about 19000, about 19100, about 19200, about 19300, about 19400, about 19500, about 19600, about 19700, about 19800, about 19900, about 20000, about 20100, about 20200, about 20300, about 20400, about 20500, about 20600, about 20700, about 20800, about 20900, about 21000, about 21100, about 21200, about 21300, about 21400, about 21500, about 21600, about 21700, about 21800, about 21900, about 22000, about 22100, about 22200, about 22300, about 22400, about 22500, about 22600, about 22700, about 22800, about 22900, about 23000, about 23100, about 23200, about 23300, about 23400, about 23500, about 23600, about 23700, about 23800, about 23900, about 24000, about 24100, about 24200, about 24300, about 24400, about 24500, about 24600, about 24700, about 24800, about 24900, about 25000 or more per nanoconjugate.

It is also contemplated that polynucleotide surface density modulates the stability of the polynucleotide associated with the nanoconjugate. Thus, in one embodiment, a nanoconjugate comprising a polynucleotide is provided wherein the polynucleotide has a half-life that is at least substantially the same as the half-life of an identical polynucleotide that is not part of a nanoconjugate. In other embodiments, the polynucleotide associated with the nanoparticle has a half-life that is about 5% greater to about 1,000,000-fold greater or more than the half-life of an identical polynucleotide that is not part of a nanoconjugate.

Hollow Nanoconjugates

As described herein, in various aspects the nanoconjugates provided by the disclosure are hollow. The porosity and/or rigidity of a hollow nanoconjugate depends in part on the density of biomolecules, and non-biomolecules when present, that are crosslinked on the surface of a nanoparticle during nanoconjugate production. In general, a lower density of biomolecules crosslinked on the surface of the nanoparticle results in a more porous nanoconjugate, while a higher density of biomolecules crosslinked on the surface of the nanoparticle results in a more rigid nanoconjugate. Porosity and density of a hollow nanoconjugate also depends on the degree and type of crosslinking between biomolecules and/or non-biomolecules.

In some aspects, a hollow nanoconjugate is produced which is then loaded with a desirable additional agent, and the nanoconjugate is then covered with a coating to prevent the escape of the additional agent. The coating, in some aspects, is also an additional agent and is described in more detail below.

Additional Agents

Additional agents contemplated by the disclosure include a biomolecule, non-biomolecule, detectable marker, a coating, a polymeric agent, a contrast agent, an embolic agent, a short internal complementary polynucleotide (sicPN), a transcriptional regulator, a therapeutic agent, an antibiotic and a targeting moiety.

Therapeutic Agents

"Therapeutic agent," "drug" or "active agent" as used herein means any compound useful for therapeutic or diagnostic purposes. The terms as used herein are understood to mean any compound that is administered to a patient for the treatment of a condition that can traverse a cell membrane more efficiently when attached to a nanoparticle or nanoconjugate of the disclosure than when administered in the absence of a nanoparticle or nanoconjugate of the disclosure.

The present disclosure is applicable to any therapeutic agent for which delivery is desired. Non-limiting examples of such active agents as well as hydrophobic drugs are found in U.S. Pat. No. 7,611,728, which is incorporated by reference herein in its entirety.

Compositions and methods disclosed herein, in various embodiments, are provided wherein the nanoconjugate comprises a multiplicity of therapeutic agents. In one aspect, compositions and methods are provided wherein the multiplicity of therapeutic agents are specifically attached to one nanoconjugate. In another aspect, the multiplicity of therapeutic agents is specifically attached to more than one nanoconjugate.

Therapeutic agents useful in the materials and methods of the present disclosure can be determined by one of ordinary skill in the art. For example and without limitation, and as exemplified herein, one can perform a routine in vitro test to determine whether a therapeutic agent is able to traverse the cell membrane of a cell more effectively when attached to a nanoconjugate than in the absence of attachment to the nanoconjugate.

In various embodiments, a drug delivery composition is provided comprising a nanoconjugate and a therapeutic agent, the therapeutic agent being one that is deliverable at a significantly lower level in the absence of attachment of the therapeutic agent to the nanogonjugate compared to the delivery of the therapeutic agent when attached to the nanogonjugate, and wherein the ratio of polynucleotide on the nanogonjugate to the therapeutic agent attached to the nanogonjugate is sufficient to allow transport of the therapeutic agent into a cell. As used herein, "ratio" refers to a number comparison of polynucleotide to therapeutic agent. For example and without limitation, a 1:1 ratio refers to there being one polynucleotide molecule for every therapeutic agent molecule that is attached to a nanogonjugate.

In one embodiment, methods and compositions are provided wherein a therapeutic agent is able to traverse a cell membrane more efficiently when attached to a nanoconjugate than when it is not attached to the nanoconjugate. In various aspects, a therapeutic agent is able to traverse a cell membrane about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold or about 100-fold or more efficiently when attached to a nanoconjugate than when it is not attached to the nanoconjugate.

Therapeutic agents include but are not limited to hydrophilic and hydrophobic compounds. Accordingly, therapeutic agents contemplated by the present disclosure include without limitation drug-like molecules, biomolecules and non-biomolecules.

Protein therapeutic agents include, without limitation peptides, enzymes, structural proteins, receptors and other cellular or circulating proteins as well as fragments and derivatives thereof, the aberrant expression of which gives rise to one or more disorders. Therapeutic agents also include, as one specific embodiment, chemotherapeutic agents. Therapeutic agents also include, in various embodiments, a radioactive material.

In various aspects, protein therapeutic agents include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, erythropoietin (EPO), thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein a, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. Examples of biologic agents include, but are not limited to, immuno-modulating proteins such as cytokines, monoclonal antibodies against tumor antigens, tumor suppressor genes, and cancer vaccines. Examples of interleukins that may be used in conjunction with the compositions and methods of the present invention include, but are not limited to, interleukin 2 (IL-2), and interleukin 4 (IL-4), interleukin 12 (IL-12). Other immuno-modulating agents other than cytokines include, but are not limited to bacillus Calmette-Guerin, levamisole, and octreotide.

As described by the present disclosure, in some aspects therapeutic agents include small molecules. The term "small molecule," as used herein, refers to a chemical compound, for instance a peptidometic that may optionally be derivatized, or any other low molecular weight organic compound, either natural or synthetic. Such small molecules may be a therapeutically deliverable substance or may be further derivatized to facilitate delivery.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

The term "drug-like molecule" is well known to those skilled in the art, and includes the meaning of a compound that has characteristics that make it suitable for use in medicine, for example and without limitation as the active agent in a medicament. Thus, for example and without limitation, a drug-like molecule is a molecule that is synthesized by the techniques of organic chemistry, or by techniques of molecular biology or biochemistry, and is in some aspects a small molecule as defined herein. A drug-like molecule, in various aspects, additionally exhibits features of selective interaction with a particular protein or proteins and is bioavailable and/or able to penetrate cellular membranes either alone or in combination with a composition or method of the present disclosure.

In various embodiments, therapeutic agents described in U.S. Pat. No. 7,667,004 (incorporated by reference herein in its entirety) are contemplated for use in the compositions and methods disclosed herein and include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (e.g., carboplastin, cisplatin and platinum (IV) (Pt (IV))).

Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. Additional antibiotic agents are discussed in detail below.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, imatinib mesylate (or GLEEVEC®), and gemcitabine.

Examples of hormonal agents include, but are not limited to, synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin compounds (e.g., 20(S) camptothecin, topotecan, rubitecan, and irinotecan), taxanes (e.g., paclitaxel and docetaxel).

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin, Pt(IV) and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Additional therapeutic agents contemplated by the present disclosure include, without limitation, the therapeutic agents in Table 2, below.

TABLE 2

| | | | |
|---|---|---|---|
| Abacavir Sulfate | Abbo-Code Index | Abciximab | Abobotulinumtoxina |
| Acamprosate Calcium | Accolate Tablets | Accutane CapsulesF | Acebutolol Hydrochloride |
| Acetadote Injection | Acetaminophen | Acetylcysteine | Acetylsalicyclic Acid |
| *Achillea Millefolium* | Aciphex Tablets | Acitretin | *Aconitum Napellus* |
| Acticin Cream | Actidose With Sorbitol Suspension | Actidose-Aqua Suspension | Actimmune |
| Activase I.V. | Active Calcium Tablets | Activella Tablets | Actonel Tablets |
| Actoplus Met Tablets | Actos Tablets | Acyclovir | Aczone Gel 5% |
| Adalimumab | Adcirca Tablets | Adefovir Dipivoxil | Adenocard IV Injection |
| Adenoscan | Adenosine | Adipex-P Capsules | Adipex-P Tablets |
| Advair Diskus 100/50 | Advair Diskus 250/50 | Advair Diskus 500/50 | Advate |
| Advicor Tablets | Afinitor Tablets | Aggrenox Capsules | Ala (Alpha-Linolenic Acid) |
| Albendazole | Albenza Tablets | Albumin (Human) | Albutein 5% Solution |
| Albutein 25% Solution | Albuterol | Albuterol Sulfate | Aldara Cream, 5% |
| Aldesleukin | Alefacept | Alendronate Sodium | Alferon N Injection |
| Alfuzosin Hydrochloride | Alimta For Injection | Aliskiren | Alitretinoin |

TABLE 2-continued

| | | | |
|---|---|---|---|
| Alkeran For Injection | Alkeran Tablets | Allantoin | Allegra Tablets |
| Allegra-D 12 Hour Extended-Release Tablets | Allegra-D 24 Hour Extended-Release Tablets | *Allium Cepa* | Allopurinol |
| Almotriptan Malate | Aloxi Injection | Alpha Tocopherol Acetate | Alpha-Hydroxy |
| Alpha₁-Proteinase Inhibitor (Human) | Alphagan P Ophthalmic Solution | Alphanate | Alphanine SD |
| Alprazolam | Altabax Ointment | Alteplase | Altretamine |
| Aluminum Hydroxide | Alvimopan | Amantadine Hydrochloride | Ambien Tablets |
| Ambien CR Tablets | Ambisome for Injection | Ambrisentan | Amerge Tablets |
| Amevive | Amicar 500 MG Tablets | Amicar 1000 MG Tablets | Amiloride Hydrochloride |
| Amino Acid Preparations | Aminobenzoate Potassium | Aminohippurate Sodium | Aminosalicyclic Acid |
| 4-Amino-Salicyclic Acid | 5-Amino-Salicyclic Acid | Amitiza Capsules | Amitriptyline Hydrochloride |
| Amlactin Moisturizing Lotion and Cream | Amlactin XL Moisturizing Lotion | Amlodipine Besylate | Amnesteem Capsules |
| Amoxicillin | Amoxil Capsules | Amoxil Tablets | Amphotericin B, Liposomal |
| Amrix Capsules | Anagrelide Hydrochloride | Anakinra | *Ananas Comosus* |
| Anaprox Tablets | Anaprox DS Tablets | Androgel | Angeliq Tablets |
| Angiomax for Injection | Animi-3 Capsules | Antihemophilic Factor (Human) | Antihemophilic Factor (Recombinant) |
| Anti-Inhibitor Coagulant Complex | Antithrombin | Antivenin (Black Widow Spider Antivenin) | Anzemet Injection |
| Anzemet Tablets | Apidra Injection | Apidra Solostar Injection | Aplenzin Extended-Release Tablets |
| Appearex Tablets | Aprepitant | Apriso Capsules | Aralast NP Solvent |
| Aranesp for Injection | Arcalyst for Subcataneous Injection | Argatroban | Aricept Tablets |
| Aricept ODT Tablets | Arixtra Injection | Armodafinil | *Arnica Montana* |
| Aromasin Tablets | Arranon Injection | Arsenic Trioxide | Artemether |
| Asacol Delayed-Release Tablets | Asacol HD Delayed-Release Tablets | Ascorbic Acid | Asenapine |
| Asmanex Twisthaler | Asparaginase | Aspirin | Atacand Tablets |
| Atacand HCT 16-12.5 Tablets | Atacand HCT 32-12.5 Tablets | Atenolol | Atomoxetine Hydrochloride |
| Atopiclair Cream | Atorvastatin Calcium | Atovaquone | Atripla Tablets |
| Atripla Tablets | Atropine Sulfate | Atryn Lyophilized Powder | Attenuvax |
| Augmentin Tablets | Augmentin XR Extended Release Tablets | Authia Cream | Avalide Film-Coated Tablets |
| Avalide Tablets | Avandamet Tablets | Avandaryl Tablets | Avandia Tablets |
| Avapro Tablets | Avastin IV | Avelox I.V. | Avelox Tablets |
| Avinza Capsules | Avita Cream | Avita Gel | Avobenzone |
| Avocado Oil | Avodart Soft Gelatin Capsules | Axert Tablets | Axid Capsules |
| Azasite Ophthalmic Drops | Azelaic Acid | Azilect Tablets | Azithromycin |
| Azmacort Inhalation Aerosol | Azor Tablets | Baclofen | Balsalazide Disodium |
| Balsam Peru | Banzel Tablets | Basiliximab | Bayer Aspirin |
| Bayer Children's Low Dose Aspirin Regimen (81 MG) Chewable Cherry and Orange | BCG, Live (intravesical) | Beclomethasone Dipropionate | Beclomethasone Dipropionate Monohydrate |
| Beconase AQ Nasal Spray | Bee Pollen | Beelith Tablets | *Belladonna* |
| *Belladonna* Alkaloids | *Bellis Perennis* | Benadryl Allergy Ultratab Tablets | Benazepril Hydrochloride |
| Bendamustine Hydrochloride | Bendroflumethiazide | Benefix Vials | Benicar Tablets |
| Benicar HCT Tablets | Bentoquatam | Bentyl Capsules | Bentyl Injection |
| Bentyl Syrup | Bentyl Tablets | Benzoyl Peroxide | Benzyl Alcohol |
| Besifloxacin | Beta-Carotene | Betamethasone | Betamethasone Dipropionate |
| Betamethasone Valerate | Betaseron For SC Injection | Betimol Ophthalmic Solution | Bevacizumab |
| Bevitamel Tablets | Bexarotene | Bexxar | Biaxin Filmtab Tablets |
| Biaxin Granules | Biaxin XL Filmtab Tablets | Bicalutamide | Bicillin C-R Injectable |
| Bicillin L-A Injection | Bilberry | Bimatoprost | Bio-C Tablets |
| Bioflavonoids | Biotin | Bisacodyl | Bismuth Subcitrate Potassium |
| Bisoprolol Fumarate | Bivalirudin | Black Widow Spider Antivenin (Equine) | Boniva Tablets |
| Boostrix Vaccine | Boron | Bortezomib | Bosentan |
| Botox for Injection | Botulinum Toxin Type A | Brevibloc Injection | Brimonidine Tartrate |

TABLE 2-continued

| | | | |
|---|---|---|---|
| Bromelain | Bromocriptine Mesylate | Budesonide | Bumetanide |
| Bupropion Hydrochloride | Buspirone Hydrochloride | Busulfan | Butenafine Hydrochloride |
| Butorphanol Tartrate | Byetta Injection | Bystolic Tablets | Calcijex Injection |
| Calcipotriene | Calcitriol | Calcium | Calcium Ascorbate |
| Calcium Carbonate | Calcium Citrate | Calcium Pantothenate | *Calendula* Pantothenate |
| *Caledula Officinalis* | *Camellia Sinensis* | Campral Tablets | Canakinumab |
| Canasa Rectal Suppositories | Cancidas For Injection | Candesartan Cilexetil | Capastat Sulfate for Injection |
| Capecitabine | Capreomycin Sulfate | Capryloyl Glycine | Captopril |
| Carac Cream 0.5% | Carafate Suspension | Carafate Tablets | Carbamazepine |
| Carbatrol Capsules | Carbidopa | Carbolic Acid | Cardio Basics Tablets |
| Cardioessentials Capsules | Cardizem La Extended Release Tablets | *Carica Papaya* | Carotenoids |
| Carvedilol | Carvedilol Phosphate | Caspofungin Acetate | Castor Oil |
| Catapres-TTS | Cathflo Activase | Cefdinir | Cefixime |
| Ceftazidime | Ceftin Tablets | Ceftriaxone Sodium | Cefuroxime |
| Cefuroxime Axetil | Celebrex Capsules | Celecoxib | Celexa Tablets |
| *Cephaelis Ipecacuanha* | Certolizumbab Pegol | Cervidil Vaginal Insert | Cetirizine Hydrochloride |
| Cetrorelix Acetate | Cetrotide for Injection | Cevimeline Hydrochloride | *Chamomilla* |
| Chantix Tablets | Charcoal, Activated | Chelated Mineral Tablets | Chemet Capsules |
| Chloral Hydrate | Chlorambucil | Chlordiazepoxide | Chlorothiazide |
| Chlorothiazide Sodium | Chloroxylenol | Chlorpheniramine Maleate | Chlorpheniramine Polistriex |
| Chlorpropamide | Chlorthalidone | Cholecalciferol | Choline Bitartrate |
| Choriogonadotropin Alfa | Chromium | Chromium Picolinate | Chromium Polynicotinate |
| Chymotrypsin | Cialis Tablets | Cilastatin Sodium | Cilostazol |
| Cimetidine | Cimetidine Hydrochloride | Cimzia | Cinacalcet Hydrochloride |
| Ciprofloxacin | Ciprofloxacin Hydrochloride | Cisatracurium Besylate | Citalopram Hydrobromide |
| Citranatal 90 DHA | Citranatal Assure | Citranatal Harmony Capsules | Citrantal RX Tablets |
| Citric Acid | Cladribine | Clarinex Tablets | Clarinex Reditabs Tablets |
| Clarinex-D 12-Hour Extended-Release Tablets | Clarinex-D 24-Hour Extended-Release Tablets | Clarithromycin | Clavulanate Potassium |
| Clevidipine Butryate | Cleviprex | Climara Transdermal System | Climara Pro Transdermal System |
| Clindamycin | Clindamycin Phosphate | Clinoril Tablets | Clobetasol Propionate |
| Clofarabine | Clorlar for Intravenous Infusion | Clomipramine Hydrochloride | Clonazepam |
| Clonidine | Clonidine Hydrochloride | Clopidogrel Bisulfate | Clorazepate Dipotassium |
| Clorpactin WCS-90 | Clorpres Tablets | Clotrimazole | Clozapine |
| CM Plex Cream | CM Plex Softgels | Coagulation Factor VIIA, Recombinant | Coartem Tablets |
| Cod Liver Oil | Codeine Phosphate | Coenzyme Q-10 | Colesevelam Hydrochloride |
| Collagen | Collagenase | Colocynthis | Colostrum |
| Combigan Ophthalmic Solution | Combivir Tablets | Comtan Tablets | Comvax |
| Concept DHA Prenatal Multivitamin Supplements | Concept OB Prenatal Multivitamin Supplements | Concerta Extended-Release Tablets | Copaxone for Injection |
| Copper | Copper, Intrauterine | Coquinone 30 Capsules | Cordymax CS-4 Capsules |
| Coreg Tablets | Coreg CR Extended-Release Capsules | Correctol Delayed-Release Tablets, USP | Cosmegen for Injection |
| Cozaar Tablets | Creon Delayed-Release Capsules | Crestor Tablets | Crixivan Capsules |
| Cubicin for Injection | Cupric Oxide | Cuprimine Capsules | Cyclobenzaprine Hydrochloride Cycloserine |
| Cyclosporine | Cymbalta Delayed-Release Capsules | Cysteine | Cytomel Tablets |
| Dacogen Injection | Dactinomycin | D-Alpha Tocopherol | Dalteparin Sodium |
| Dapsone | Daptomycin | Daraprim Tablets | Darbepoetin Alfa |
| Darifenacin | Darvocet-A 500 Tablets | Darvocet-N 50 Tablets | Darvocet-N 100 Tablets |
| Darvon Pulvules | Darvon-N Tablets | Daytrana Transdermal Patch | Ddrops Dietary Supplement |
| Decitabine | Deferasirox | Delatestryl Injection | Demser Capsules |
| Denavir Cream | Denileukin Diftitox | Depakene Capsules | Depakote Delayed Release Tablets |
| Depakote ER Extended Release Tablets | Depakote Sprinkle Capsules | Deprenyl | Derma-Smoothe/FS Topical Oil |
| Dermotic Oil | Desflurane | Desloratadine | Desonide |
| Desvenlafaxine Succinate | Dexamethasone | Dexedrine Spansule Sustained-Release Capsules | Dexlansoprazole |
| Dexmethylphenidate Hydrochloride | Dextroamphetamine Sulfate | Dextromethorphan Hydrobromide | Dextrose |

TABLE 2-continued

| | | | |
|---|---|---|---|
| DHA (Docosahexaenoic Acid) | Diazepam | Diazoxide | Dibasic Sodium Phosphate |
| Dibenzyline Capsules | Diclofenac Epolamine | Diclofenac Potassium | Diclofenac Sodium |
| Dicyclomine Hydrochloride | Didronel Tablets | Dietary Supplement | Digestive Enzymes |
| Digibind for Injection Digoxin | Digoxin Immune Fab (Ovine) | Dilaudid Injection | Dilaudid Tablets |
| Dilaudid-HP Injection | Dilaudid-HP Lyophilized Powder 250 MG | Diltiazem Hydrochloride | Dinoprostone |
| Dioctyl Sodium Sulfosuccinate | Diovan Tablets | Diovan HCT Tablets | Diphenhydramine Hydrochloride |
| Diphenoxylate Hydrochloride | Diphenylhydantoin | Diphtheria & Tetanus Toxoids and Acellular Pertussis Vaccine Adsorbed | Diphtheria and Tetanus Toxoids and Acellular Pertussis Adsorbed and Inactivated Poliovirus Vaccine |
| Dipyridamole | Disocorea | Divalproex Sodium | Divigel |
| Divista Softgel Capsules | Docetaxel | Docosahexanenoic Acid (DHA) | Docusate Sodium |
| Dolasetron Mesylate | Donepezil Hydrochloride | Donnatal Extentabs | Doribax Injection |
| Dornase Alfa | Doryx Delayed-Release Tablets | Dorzolamide Hydrochloride | Doxazosin Mesylate |
| Doxepin Hydrochloride | Doxil Injection | Doxorubicin Hydrochloride Liposome | Doxycycline |
| Doxycycline Hyclate | Dronedarone | Drospirenone | Drotrecogin Alfa (Activated) |
| Duet Tablets | Duet DHA Tablets and Softgel Capsules | Duetact Tablets | Duloxetine Hydrochloride |
| Duraclon Injection | Dutasteride | Dyazide Capsules | Dynacirc CR Controlled Release Tablets |
| Dyrenium Capsules | Dysport for Injection | *Echinacea Angustifolia* | *Echinacea Purpurea* |
| EC-Naprosyn Delayed-Release Tablets | Eculizumab | Edecrin Tablets | Edecrin Sodium Intravenous |
| Edetate Calcium Disodium | E.E.S. 400 Filmtab Tablets | E.E.S. Granules | Efavirenz |
| Effexor XR Extended-Release Capsules | Effient Tablets | Effient Tablets | Eicosapentaenoic Acid (EPA) |
| Eldepryl Capsules | Elidel Cream 1% | Eligard 7.5 MG | Eligard 22.5 MG |
| Eligard 30 MG | Eligard 45 MG | Elitek | Elmiron Capsules |
| Eloxatin for Injection | Elspar for Injection | Elspar for Injection | Eltrombopag |
| Embeda Extended Release Capsules | Emend Capsules | Emend for Injection | Emtricitabine |
| Emtriva Capsules | Emtriva Oral Solution | Enablex Extended-Release Tablets | Enalapril Maleate |
| Enbrel for Injection | Enflurane | Engerix-B Vaccine | Enjuvia Tablets |
| Enoxaparin Sodium | Entacapone | Entereg Capsules | Enzymes, Collagenolytic |
| Enzymes, Debridement | Enzymes, Digestive | Enzymes, Proteolytic | Epinastine Hydrochloride |
| Epinephrine | Epipen Auto-Injector | Epipen 2-Pak | Epipen Jr. Auto-Injector |
| Epipen Jr. 2-Pak | Epivir Oral Solution | Epivir Tablets | Epivir-HBV Oral Solution |
| Epivir-HBV Tablets | Epoetin Alfa | Epogen for Injection | Epoprostenol Sodium |
| Eprosartan Mesylate | Eptifibatide | Epzicom Tablets | Equetro Extended-Release Capsules |
| Erlotinib | Ertapenem | Eryped 200 & Eryped 400 Oral Suspension | Erthromycin Ethylsuccinate |
| Escitalopram Oxalate | Esmolol Hydrochloride | Esomeprazole Magnesium | Esomeprazole Sodium |
| Entrace Tablets | Estradiol | Estradiol Acetate | Estrogens, Conjugated, Synthetic B |
| Estropipate | Estrostep FE Tablets | Etanercept | Ethacrynate Sodium |
| Ethacrynic Acid | Ethinyl Estradiol | Ethosuximide | Editronate Disodium |
| Etoposide | *Euphrasia Officinalis* | Everolimus | Evista Tablets |
| Evoxac Capsules | Exelon Capsules | Exemestane | Exenatide |
| Exforge Tablets | Exforge HCT Tablets | Exjade Tablets | Extavia Kit |
| Ez-Char Activated Charcoal Pellets | Ezetimibe | Factor IX (Human) | Factor IX Complex |
| Famotidine | Fanapt Tablets | Faslodex Injection | Fatty Acids |
| Febuxostat | Feiba VH | Felodipine | Femara Tablets |
| Femcon FE Tablets | Femhrt Tablets | Femtrace Tablets | Fenofibrate |
| Fenoglide Tablets | Fenoprofen Calcium | Fentanyl | Fentanyl Citrate |
| Fentora Tablets | Ferralet 90 Tablets | Ferralet 90 Tablets | Ferrous Fumarate |
| Ferrous Fluconate | Ferrous Sulfate | Fesoterodine Fumarate | Fexofenadine Hydrochloride |
| Fiber | Fiber Supplement | Filgrastim | Finasteride |
| Flebogamma 5% DIF | Flecainide Acetate | Fleet Babylax Suppositories | Fleet Bisacodyl Laxatives |
| Fleet Pedia-Lax Chewable Tablets | Flexbumin 25% I.V. | Flolan for Injection | Flonase Nasal Spray |
| Florical Capsules | Florical Tablets | Flovent Diskus 50 MCG | Flovent Diskus 100 MCG |
| Flovent Diskus 250 MCG | Flovent HFA 44 MCG Inhalation Aerosol | Flovent HFA 110 MCG Inhalation Aerosol | Flovent HFA 250 MCG Inhalation Aerosol |

TABLE 2-continued

| | | | |
|---|---|---|---|
| Fluarix Vaccine | Fludarabine Phosphate | Flulaval Injection Vaccine | Flumazenil |
| Flumist Vaccine | Fluocinolone Acetonide | Fluocinonide | Fluorouracil |
| Fluoxetine | Fluoxetine Hydrochloride | Fluphenazine Hydrochloride | Flurazepam Hydrochloride |
| Flurbiprofen | Fluticasone Furoate | Fluticasone Propionate | Fluvoxamine Maleate |
| Focalin XR Capsules | Folate | Folgard OS Tablets | Folic Acid |
| Follistim AQ Cartridge | Follitropin Alfa | Follitropin Beta | Fondaparinux Sodium |
| Foradil, Aerolizer | Forane Liquid for Inhalation | Formadon Solution | Formaldehyde |
| Formoterol Fumarate | Formoterol Fumarate Dihydrate | Fortaz Injection | Fortaz for Injection |
| Forteo for Injection | Fosamax Tablets | Fosamax Plus D Tablets | Fosamprenavir Calcium |
| Fosaprepitant Dimeglumine | Foscarnet Sodium | Foscavir Injection | Fosrenol Chewable Tablets |
| Fragmin Injection | Frova Tablets | Frovatriptan Succinate | Fulvestrant |
| Furosemide | Gabitril Tablets | Galantamine | Gammagard Liquid |
| Gammagard S/D | Gamunex | *Ganoderma Lucinum* Mushroom Extract | Gardasil Injection |
| Gemcitabine Hydrochloride | Gemtuzumac Ozogamicin | Gemzar for Injection | Gengraf Capsules |
| Genotropin Lyophilized Powder | Geodon Capsules | Geodon for Injection | Glatiramer Acetate |
| Gleevec Tablets | Gliadel Wafer | Glimepiride | Glipizide |
| Glucagon | Glucono-Delta-Lactone | Glucosamine Sulfate | Glutose 15, Glutose 45 (Oral Glucose Gel) |
| Glyburide | Glycerin | Glyceryl Guaiacolate | Glyceryl Trinitrate |
| Glycyrrhestinic Acid | Goldenseal | Golimumab | Gonal-F For Injection |
| Gonal-F RFf for Injection | Gonal-F RFF Pen for Injection | Gordochom Solution | Granisetron Hydrochloride |
| Guaifenesin | Guanfacine Hydrochloride | Haemophilus B Conjugate Vaccine | Haldol Injection |
| Haldol Decanoate Injection | Haloperidol | *Hamamelis Virginiana* | Happycode Spray |
| Havrix Injection Vaccine | Hemin | Hemocyte Tablets | Hemofil M |
| Hepatitis A Vaccine, Inactivated | Hepatitis B Vaccine, Recombinant | HEP-Forte Capsules | Heplive Softgel Capsules |
| Hepsera Tablets | Herbals, Multiple | Herbals with Minerals | Herbals with Vitamins & Minerals |
| Herceptin I.V. | Hexalen Capsules | Histrelin Acetate | Homeopathic Formulation |
| Humalog-Pen and Kwikpen | Humatrope Vials and Cartridges | Humira Injection Syringe and Pen | Humulin 50/50, 100 Units |
| Humulin 70/30 Vial | Humulin N Vial | Humulin R | Humulin R (U-500) |
| Hyalgan Solution | Hycamtin Capsules | Hycamtin for Injection | Hycet Oral Solution |
| *Hydrastis canadensis* | Hydrochlorothiazide | Hydrocodone bitartrate | Hydrocodone polistirex |
| Hydromorphone hydrochloride | Hydroxychloroquine sulfate | Hydroxypropyl cellulose | Hyland's calms forté 4 kids tablets |
| Hyand's calms forté caplets | Hyland's calms forté tablets | Hyland's cold 'n cough 4 kids | Hyland's colic tablets |
| Hyland's earache drops | Hyland's leg cramps PM with quinine tablets | Hyland's leg cramps with quinine caplets | Hyland's leg cramps with quinine tablets |
| Hyland's nerve tonic caplets | Hyland's nerve tonic tablets | Hyland's restful legs tablets | Hyland's sniffles 'n sneezes 4 kids tablets |
| Hyland's teething gel | Hyland's teething tablets | Hyoscine hydrobromide | Hyoscyamine sulfate |
| *Hypericum perforatum* | Hyzaar 50-12.5 tablets | Hyzaar 100-12.5 tablets | Hyzaar 100-25 tablets |
| Ibandronate sodium | Ibuprofen | Ibuprofen Lysine | Ilaris Injection |
| Iloperidone | Imatinib mesylate | Imipenem | Imiquimod |
| Imitrex injection | Imitrex nasal spray | Imitrex tablets | Immune globulin intravenous (human) |
| Immunizen capsules | Immunocal powder sachets | Imodium A-D liquid caplets, and EZ chews | Imodium multi-symptom relief caplets and chewable tablets |
| Implanon implant | Indapamide | Indinavir sulfate | Indocin capsules |
| Indocin I.V. | Indocin oral suspension | Indocin suppositories | Indomethacin |
| Indomethacin sodium trihydrate | Infanrix injection vaccine | Infants' strength products | Infliximab |
| Influenza virus vaccine | Influenza virus vaccine live, intranasal | Innopran XL extended release capsules | Inositol |
| Insulin, human (RDNA origin) | Insulin aspart, human | Insulin aspart, human regular | Insulin aspart protamine, human |
| Insulin detemir (RDNA origin) | Insulin glargine | Insulin glulisine | Insulin Lispro, human |
| Insulin lispro protamine, human | Insulin, human NPH | Insulin, human regular | Insulin, human regular and human NPH mixture |
| Integra F supplement capsules | Integra plus supplement capsules | Integra supplement capsules | Integrilin injection |
| Interferon alfa-2B, recombinant | Interferon alfa-N3 (human leukocyte derived) | Interferon beta-1A | Interferon beta-1B |

TABLE 2-continued

| | | | |
|---|---|---|---|
| Interferon gamma-IB | Intravenous sodium diuril | Intron A for injection | Intuniv extended release tablets |
| Invanz for injection | Invega extended-release tablets | Invega sustenna extended-release injectable suspension | Iodine |
| Iodine I 131 tositumomab | Ipratropium bromide | Iquix ophthalmic solution | Irbesartan |
| Iron Carbonyl | Iron Polysaccharide complex | Isentress Tablets | Isocarboxazid |
| Isoflurane | Isotretinoin | Isradipine | Ivermectin |
| Ivy Block | Janumet Tablets | Januvia Tablets | Kaletra Oral Solution |
| Kaletra Tablets | Kapidex Delayed Release Capsules | Kepivance | Keppra XR Extended-Release Tablets |
| Ketek Tablets | Ketoconazole | Ketoprofen | Ketorolac Tromethamine |
| Ketotifen Fumarate | Kineret Injection | Kinrix Injection Vaccine | Klonopin Tablets |
| Klonopin Wafers | Klor-Con s/Klor-Con 10 Tablets | Klor-Con M20/Flor-Con M10/Klor-Con M15 Tablets | K-Phos Original (Sodium Free) Tablets |
| K-Phos M.F. Tablets | K-Phos Neutral Tablets | K-Phos No. 2 Tablets | Kristalose for Oral Solution |
| Lacosamide | Lacrisert Sterile Ophthalmic Insert | Lactic Acid | Lactulose |
| Lamictal Chewable Dispersible Tablets | Lamictal ODT Orally Disintegrating Tablets | Lamictal Tablets | Lamictal XR Extended-Release Tablets |
| *Laminaria Hyperborea* | Lamivudine | Lamotrigine | Lanoxin Injection |
| Lanoxin Injection Pediatric | Lanoxin Tablets | Lanthanum Carbonate | Lantus Injection |
| Lapatine | L-Arginine | L-Carnitine | L-Cysteine |
| Lepirudin | Letairis Tablets | Letrozole | Leukeran Tablets |
| Leuprolide Acetate | Leustatin Injection | Levaquin Injection | Levaquin Oral Solution |
| Levaquin Tablets | Levaquin in 5% Dextrose Injection | Levemir Injection | Levetiracetam |
| Levitra Tablets | Levitra Tablets (see Schering) | Levocarnitine | Levocetirizine Dihydrochloride |
| Levodopa | Levofloxacin | Levonorgestrel | Levothyroxine Sodium |
| Levoxyl Tablets | Lexapro Oral Suspension | Lexapro Tablets | Lexiscan Injection |
| Lexiva Oral Suspension | Lexiva Tablets | Lialda Tablets | Lidocaine |
| Lidoderm Patch | Lifepak Capsules | Linezolid | Liothyronine Sodium |
| Lipitor Tablets | Lipoic Acid | Lisdexamfetamine Dimesylate | Lisinopril |
| Liver, Dessicated | Liver Fractions | Liver Preparations | L-Lysine |
| Loestrin 24 Fe Tablets | Loperamide Hydrochloride | Lopinavir | Lorazepam |
| Losartan Potassium | Loseasonique Tablets | Lovastatin | Lovaza Capsules |
| Lovenox Injection | Loxapine Hydrochloride | L-Proline | Lubiprostone |
| Lucentis Injection | Lumefantrine | Lumigan Ophthalmic Solution | Lupron Depot 3.75 MG |
| Lupron Depot 7.5 MG | Lupron Depot-3 month 11.25 MG | Lupron Depot-3 month 22.5 MG | Lupron Depot-4 month 30 MG |
| Lupron Depot-Fed 7.5 MG, 11.25 MG and 15 MG | Lutein | Lutropin Alfa | Luveris for Injection |
| Lybrel Tablets | *Lycium Barbarum* | *Lycopodium Clavatum* | Lyrica Capsules |
| Mafenide Acetate | Mag-Al Liquid | Mag-Al Plus | Mag-Al Plus XS |
| Mag-Al Ultimate Strength | Magnesium | Magnesium Carbonate | Magnesium Citrate |
| Magnesium Hydroxide | Magnesium Oxide | Magnesium Sulfate | Malarone Pediatric Tablets |
| Malarone Tablets | Manganese | Manganese Sulfate | Maprotiline Hydrochloride |
| Maraviroc | Marineomega Softgel Capsules | Maritime Pine Extract | Marplan Tablets |
| Mavik Tablets | Maxair Autohaler | Maxalt Tablets | Maxalt-MLT Orally Disintegrating Tablets |
| Maximum Strength Products | Maxzide Tablets | Maxzide-25 MG Tablets | Measles, Mumps, Rubella and Varicella Virus Vaccine, Live |
| Measles, Mumps & Rubella Virus Vaccine, Live | Measles Virus Vaccine, Live | Mechlorethamine Hydrochloride | Meclofenamate Sodium |
| Med Omega Fish Oil | Medizym Tablets | Medroxyprogesterone Acetate | Mega Antioxidant Tablets |
| Megace Es Oral Suspension | Megestrol Acetate | Meili Soft Capsules | Meili Clear Soft Capsules |
| Melatonin | Meloxicam | Melphalan | Melphalan Hydrochloride |
| Memantine Hydrochloride | Menthol | Mephyton Tablets | Mepron Suspension |
| Mercaptopurine | Meribin Capsules | Meridia Capsules | Meropenem |
| Merrem I.V. | Meruvax II | Mesalamine | Metadate CD Capsules |
| Metaxalone | Metformin Hydrochloride | Methadone Hydrochloride | Methenamine Mandelate |
| Methionne | Methotrexate Sodium | Methyclothiazide | Methyl Salicylate |

TABLE 2-continued

| | | | |
|---|---|---|---|
| Methyldopa | Methylnaltrexone Bromide | Methylphenidate | Methylphenidate Hyrdochloride |
| Metoclopramide Hydrochloride | Metolazone | Metoprolol Succinate | Metoprolol Tartrate |
| Metozolov Tablets | Metronidazole | Metyrosine | Mevacor Tablets |
| Micafungin Sodium | Micardis Tablets | Micardis HCT Tablets | Miconazole Nitrate |
| Midodrine Hydrochloride | Milk of Magnesia | Milk of Magnesia Suspension | Milk of Magnesia Concentrate (24% Suspension) |
| Milnacipran Hydrochloride | Mineral Oil | Minerals | Minerals, Multiple |
| Minocycline Hydrochloride | Mirtazapine | Mitoxantrone Hydrochloride | M-M-R II |
| Moban Tablets | Modafinil | Modicon Tablets | Molindone Hydrochloride |
| Molybdenum | Mometasone Furoate | Mometasone Furoate Monohydrate | Monobasic Sodium Phosphate |
| Montelukast Sodium | Morphine Sulfate | Motrin IB Tablets and Caplets | Children's Motrin Dosing Chart |
| Children's Motrin Oral Suspension | Children's Motrin Non-Staining Dye-Free Oral Suspension | Infants' Motrin Concentrated Drops | Infants' Motrin Non-Staining Dye-Free Concentrated Drops |
| Junior Strength Motrin Caplets and Chewable Tablets | Moviprep Oral Solution | Moxatag Tablets | Moxifloxacin Hydrochloride |
| MS Contin Tablets | Multaq Tablets | Multiminerals | Multivitamins |
| Multivitamins with Minerals | Mumps Virus Vaccine, Live | Mumpsvax | Mupirocin |
| Mupirocin Calcium | Muromonab-CD3 | Mustargen for Injection | Mycamine for Injection |
| Mycophenolate Mofetil | Mycophenolic Acid | Myfortic Tablets | Myleran Tablets |
| Mylotarg for Injection | Nadolol | Naftifine Hydrochloride | Nameda Oral Solution |
| Nameda Tablets | Naprosyn Suspension | Naprosyn Tablets | Naproxen |
| Naproxen Sodium | Naratriptan Hydrochloride | Nasacort AQ Nasal Spray | Nascobal Nasal Spray |
| Nasonex Nasal Spray | Natrecor for Injection | Naturethroid Tablets | Nebivolol |
| Nelarabine | Nembutal Sodium Solution, USP | Neoprofen Injection | Neoral Oral Solution |
| Neoral Soft Gelatin Capsules | Neulasta Injection | Neupogen for Injection | Nevirapine |
| Nexium Delayed-Release Capsule | Nexium Delayed-Release Oral Suspension | Nexium I.V. | Niacin |
| Niacinamide | Niaspan Extended-Release Tablets | Nicardipine Hydrochloride | Nicotinic Acid |
| Nifedipine | Nilotnib | Nimbex Injection | Nisoldipine |
| Nitrofurantoin Macrocrystals | Nitrofurantoin Monohydrate | Nitroglycerin | Nitrolingual Pumpspray |
| Nizatidine | Norditropin Cartridges | Norel SR Tablets | Norelgestromin |
| Norethindrone | Norethindrone Acetate | Norflex Injectable | Norfloxacin |
| Norgestimate | Noroxin Tablets | Nortriptyline Hydrochloride | Norvir Oral Solution |
| Norvir Soft Gelatin Capsules | Norwegian Cod Liver Oil | Novantrone for Injection Concentrate | Novolog Injection |
| Novolog Mix 70/30 | Novoseven RT | Noxafil Oral Suspension | Nplate |
| Nucynta Tablets | Nu-Iron 150 Capsules | Nu-Iron Elixir | Nutropin for Injection |
| Nutropin AQ Injection | Nutropin AQ Nuspin Injection | Nutropin AQ Pen Cartridge | Nuvaring |
| Nuvigil Tablets | Nystatin | Octocrylene | Octreotide Acetate |
| Oforta Tablets | Olanzapine | Olive Oil | Olmesartan Medoxomil |
| Olopatadine Hydrochloride | Omalizumab | Omega-3-Acid Ethyl Esters | Omega-3 Acids |
| Omega-3 Polyunsaturates | Omegalife-3 Supplementation | Omerprazole | Omnicef Capsules |
| Omnicef for Oral Suspension | Onabotulinumtoxina | Oncaspar Injection | Ondansetron |
| Ondansetron Hydrochloride | Onglyza Tablets | Onion | Onsolis Film |
| Ontak Vials | Opana Tablets | Opana ER Tablets | Oramorph SR Tablets |
| Orlistat | Orphenadrine Hydrochloride | Ortho-Cept Tablets | Ortho Micronor Tablets |
| Ortho-Novum Tablets | Ortho-Novum 1/50 Tablets | Ortho Tri-Cyclen LO Tablets | orthoclone OKT3 Sterile Solution |
| Ortho-Cyclen Tablets | Oseltamivir Phosphate | Osmoprep Tablets | Ovcon 35 Tablets |
| Ovcon 50 Tablets | Ovidrel Prefilled Syringe For Injection | Oxaliplatin | Oxybenzone |
| Oxybutynin Chloride | Oxycodone Hydrochloride | Oxycontin Tablets | Oxymetazoline Hydrochloride |
| Oxymorphone Hydrochloride | Palifermin | Paliperidone | Palivizumab |
| Palonosetron Hydrochloride | Pancreatin | Pancrelipase | Panhematin For Injection |

TABLE 2-continued

| | | | |
|---|---|---|---|
| Panitumumab | Pantoprazole Sodium | Pantothenate, Calcium | Pantothenic Acid |
| Papain | Parafon Forte DSC | Paricalcitol | Parnate Tablets |
| Paroxetine | Paroxetine Hydrochloride | Paser Granules | Pataday Ophthalmic Solution |
| Patanase Nasal Spray | Paxil Oral Suspension | Paxil Tablets | Paxil CR Controlled-Release Tablets |
| Pediarix Vaccine | Liquid Pedvaxhib | PEG-3350 | Pegasparagase |
| Pegfilgrastim | Peginterferon Alfa-2B | Pegintron Powder For Injection | Pemetrexed Disodium |
| Pemirolast Potassium | Penciclovir | PenicillaminePenicillin G Benzathine | Penicillin G Procaine |
| Pentasa Capsules | Pentobarbital Sodium | Pentosan Polysulfate Sodium | Pentoxifylline |
| Pepcid Tablets | Maximum Strength Pepcid AC Tablets | Percocet Tablets | Percodan Tablets |
| Perforomist Inhalation Solution | Permethrin | Perphenazine | Petrolatum, White |
| Phenazopyridine Hydrochloride | Phenobarbital | Phenol | Phenoxybenzamine Hydrochloride |
| Phentermine Hydrochloride | Phenylazodiamino Pyridine Hydrochloride | Phenylephrine Hydrochloride | Phenyltoloxamine Citrate |
| Phenytek Capsules | Phenytoin Sodium | Extended Phenytoin Sodium Capsules | Phosphorus |
| Photofrin For Injection | Phytonadione | Phytosterols | Pilocarpine Hydrochloride |
| Pimecrolimus | Pindolol | Pink Bismuth | Pioglitazone Hydrochloride |
| Piperacillin Sodium | Pirbuterol Acetate | Piroxicam | Pitcher Plant Distillate |
| Plan B One-Step Tablets | Plasma/Albumin-Free | Plavix Tablets | Pneumococcal Vaccine, Diphtheria Conjugate |
| Pneumococcal Vaccine, Polyvalent | Pneumovax 23 | Policosanol | Poliprosan 20 With Carmustine |
| Poliovirus Vaccine Inactivated | Polyethylene Glycol | Polysaccharide Iron Complex | Porfimer Sodium |
| Posaconazole | Potaba Capsules | Potaba Tablets | Potassium |
| Potassium Acid Phosphate | Potassium Chloride | Potassium Citrate | Potassium Iodide |
| Potassium Phosphate | Pramlintide Acetate | Prasugrel Hydrochloride | Pravastatin Sodium |
| Prazosin Hydrochloride | Prednisolone Sodium Phosphate | Pregabalin | Premarin Intraveous |
| Premarin Tablets | Premphase Tablets | Prempro Tablets | Prenexa Capsules |
| Prevnar | Primaxin I.M. | Primaxin I.V. | Prinivil Tablets |
| Prinzide Tablets | Pristiq Extended-Release Tablets | Proair HFA Inhalation Aerosol | Probenecid |
| Prochlorperazine Maleate | Procosa II Tablets | Procrit For Injection | Profilnine SD |
| Proflavanol 90 Tablets | Progesterone | Proglycem Capsules | Proglycem Suspension |
| Prograf Capsules | Prograf Injection | Proguanil Hydrochloride | Prolastin |
| Proleukin For Injection | Promacta Tablets | Promethazine Hydrochloride | Prometrium Capsules (100 MG, 200 MG) |
| Propafenone Hydrochloride | Propecia Tablets | Propoxyphene Hydrochloride | Propoxyphene Napsylate |
| Propranolol Hydrochloride | Propylene Glycol | Proquad | Proscar Tablets |
| Proteolytic Enzymes | Protonix For Delayed-Release Oral Suspension | Protonix Delayed-Release Tablets | Protonix |
| Protopic Ointment | Proventil HFA Inhalation Aerosol | Provigil Tablets | Prozac Weekly Capsules |
| Prozac Pulvules | Pseudoephedrine Hydrochloride | Pseudoephedrine Sulfate | Pulmicort Flexhaler |
| Pulmozyme Inhalation Solution | *Pulsatilla Pratensis* | Pylera Capsules | Pyridium Tablets |
| Pyrimethamine | Quadrivalent Human Papillomavirum (Types 6, 11, 16, 18) Recombinant Vaccine | Quetiapine Fumarate | Quinapril Hydrochloride |
| Quinine | Quixin Ophthalmic | Qvar Inhalation Aerosol | Raberprazole Sodium |
| Raloxifene Hydrochloride | Raltegravir | Ramelteon | Ranexa Extended-Release Tablets |
| Ranibizumab | Ranitidine Hydrochloride | Ranolazine | Rapamune Oral Solution |
| Rapamune Tablets | Rasagiline Mesylate | Rasburicase | Razadyne Oral Solution |
| Razadyne Tablets | Razadyne ER Extended-Release Capsules | Rebetol Capsules | Rebetol Oral Solution |
| Rebif Prefilled Syringe For Injection | Reclast Injection | Recombinate | Recombivax HB |
| Refacto Vials | Refludan For Injection | Regadenoson | Regular Strength Products |
| Reishimax GLP Capsules | Relenza Inhalation Powder | Relistor Injection | Relistor Injection |
| Remeron Tablets | Remeronsoltab Tablets | Remicade For IV Injection | Renacidin Irrigation |

TABLE 2-continued

| | | | |
|---|---|---|---|
| Reopro Vials | Requip Tablets | Requip XL Tablets | Restasis Ophthalmic Emulsion |
| Retapamulin | Retrovir Capsules | Retrovir IV Infusion | Retrovir Syrup |
| Retrovir Tablets | RH$_9$ (D) Immune Globulin (Human) | *Rhus Toxicodendron* | Ribavirin |
| *Ribes Nigrum* | Riboflavin | Rifaximin | Rilonacept |
| Rilutek Tablets | Riluzole | Risedronate Sodium | Risperdal M-Tab |
| Risperdal Oral Solution | Risperdal Tablets | Risperdal Consta Long-Acting Injection | Risperidone |
| Ritonavir | Rituxan | Rituximab | Rivastigmine Tartrate |
| Rizathiptan Benzoate | Rocephin Injectable Vials | Rocuronium Bromide | Extra Strength Rolaids Softchews Vanilla Crème |
| Romazicon Injection | Romiplostim | Ropinirole Hydrochloride | Rosiglitazone Maleate |
| Rosuvastatin Calcium | Rotarix Oral Suspension | Rotateq | Rotavirus Vaccine, Live, Oral |
| Rotavirus Vaccine, Live, Oral, Pentavalent | Roxanol Oral Solution | Roxicodone Oral Solution | Roxicodone Tablets |
| Rozerem Tablets | Rubella Virus Vaccine, Live | Rufinamide | Rythmol Tablets |
| Rythmol SR Extended Release Capsules | Ryzolt Extended-Release Tablets | Sabril Oral Solution | Sabril Tablets |
| St. Joseph 81 MG Aspirin Chewable and Enteric Coated Tablets | Saizen For Injection | Salagen Tablets | Salmeterol Xinafoate |
| Salmon Oil | Salonpas Arthritis | Salonpas Pain Relief Patch | Sandostatin Injection |
| Sandostatin LAR Depot | Santyl Collagenase Ointment | Saphris Tablets | Sarafem |
| Sarapin Vials | Sarraceniaceae | Savella Tablets | Saxagliptin |
| Scopolamine | Scopolamine Hydrobromide | Seasonique Tablets | Selegiline |
| Selegiline Hydrochloride | Selenium | Selzentry Tablets | *Senna* |
| Sennosides | Sen-Sei-Ro Powder Gold | Sensipar Tablets | Serevent Diskus |
| Seromycin Capsules | Seroquel Tablets | Seroquel XR Extended-Release Tablets | Serostim For Injection |
| Sertraline Hydrochloride | Sevoflurane | Sheep Placenta | Sibutramine Hydrochloride Monohydrate |
| Silicea | Silicone | Simcor Tablets | Simethicone |
| Simponi Injection | Simulect For Injection | Simvastatin | Singulair Tablets |
| Singular Oral Granules | Sirolimus | Sitagliptin Phosphate | Skelaxin Tablets |
| Slo-Niacin Tablets | Sodium | Sodium Acid Phosphate | Sodium Ascorbate |
| Sodium Chloride | Sodium Citrate | Sodium Fluoride | Sodium Hyaluronate |
| Sodium Oxychlorosene | Sodium Phosphate | Sodium Sulfacetamide | Sodium Sulfate |
| Solifenacin Succinate | Soliris Concentrated Solution for Intravenous Infusion | Solodyn Extended Release Tablets | Somatostatin Analogue |
| Somatropin | Somatropin (RDNA Origin) | Son Formula Tablets | Sorbitol |
| Sore Throat Spray | Soriatane Capsules | Sotalol Hydrochloride | Soy Oil |
| Spacer, Inhalation | Spiriva Handihaler | Spironolactone | Spirulina |
| Springcode Spray | Stalevo Tablets | Stavudine | Strattera Capsules |
| Striant Mucoadhesive | Stromectol Tablets | Succimer | Sucralfate |
| Sudafed 12 Hour Nasal Decongestant Non-Drowsy Caplets | Sudafed 24 Hour Non-Drowsy Nasal Decongestant Tablets | Sudafed Nasal Decongestant Tablets | Sudafed PE Nasal Decongestant Tablets |
| Children's Sudafed Nasal Decongestant Liquid | Children's Sudafed PE Nasal Decongestant Liquid | Sudafed OM Sinus Congestion Moisturizing Nasal Spray | Sulfamethoxazole |
| Sulfur | Sulindac | Sumatriptan | Sumatriptan Succinate |
| Sunitinib Malate | Super Omega-3 Softgels | Supprelin La Implant | Suprane Liquid for Inhalation |
| Suprax for Oral Suspension | Suprax Tablets | Sutent Capsules | Symbicort 80/4.5 Inhalation Aerosol |
| Symbicort 160/4.5 Inhalation Aerosol | Symbyax Capsules | Symlin Injection | Symlinpen |
| *Symphytum Officinale* | Synagis Intramuscular Solution | Synthroid Tablets | Syprine Capsules |
| Systane Ultra Lubricant Eye Drops | Tabloid Tablets | Taclonex Ointment | Taclonex Scalp Topical Suspension |
| Tacrolimus | Tadalafil | Tambocor Tablets | Tamiflu Capsules |
| Tamiflu Oral Suspension | Tamoxifen Citrate | Tandem Capsules | Tandem DHA Capsules |
| Tandem F. Capsules | Tandem OB Capsules | Tandem Plus Capsules | Tapentadol Hydrochloride |
| Tarceva Tablets | Targretin Capsules | Tarka Tablets | Tasigna Capsules |
| Taurine | Taxotere Injection Concentrate | Tazobactam Sodium | Tegreen 97 Capsules |
| Tekturna Tablets | Tekturna HCT Tablets | Telithromycin | Telmesteine |
| Telmisartan | Temazepam | Temodar Capsules | Temodar Injection |

TABLE 2-continued

| | | | |
|---|---|---|---|
| Temozolomide | Temsirolimus | Tenecteplase | Tenofovir Disoproxil Fumarate |
| Terazol 3 Vaginal Suppositories | Terazosin Hydrochloride | Terbinafine Hydrochloride | Teriparatide |
| Testosterone | Testosterone Enanthate | Tetrabenazine | Tetracycline Hydrochloride |
| Teveten Tablets | Teveten HCT Tablets | Tev-Tropin for Injection | Theophylline |
| Theophylline Anhydrous | Thiamine Disulfide | Thiamine Mononitrate | Thioguanine |
| Thioridazine Hydrochloride | Thiothixene | Thymus Polypeptide | Thyroid |
| Tiagabine Hydrochloride | Ticarcillin Disodium | Tice BCG | Tigecycline |
| Timentin Add-Vantage | Timentin Injection Galaxy Container | Timentin IV Infusion | Timentin Pharmacy Bulk Package |
| Timolol Hemihydrate | Timolol Maleate | Timoptic In Ocudose | Timoptic Sterile Ophthalmic Solution |
| Tiotropium Bromide | Tizanidine | Tnkase | Tobi Nebulizer Solution for Inhalation |
| Tobramycin | Tocopheryl Acetate | Tolazamide | Tolbutamide |
| Tolectin 200/400/600 | Tolmetin Sodium | Topamax Sprinkle Capsules | Topamax Tablets |
| Topiramate | Topotecan Hydrochloride | Toprol-XL Tablets | Torisel Injection |
| Tositumomab | Toviaz Extended-Release Tablets | Tracleer Tablets | Tramadol Hydrochloride |
| Trandolapril | Tranylcypromine Sulfate | Trastuzumab | Traumeel Ear Drops |
| Traumeel Injection Solution | Traumeel Oral Drops | Traumeel Oral Liquid In Vials | Traumeel Tablets |
| Travatan Z Ophthalmic Solution | Travoprost | Treanda For Injection | Tretinoin |
| Treximet Tablets | Triamcinolone Acetonide | Triamterene | Tribasic Calcium Phosphate |
| Tricitrates Oral Solution | Tricitrates SF Oral Solution | Tricor Tablets | Trientine Hydrochloride |
| Trifluoperazine Hydrochloride | Trihexyphenidyl Hydrochloride | Trilipix Delayed Release Capsules | Trimethoprim |
| Trisenox Injection | Trizivir Tablets | Trusopt Sterile Ophthalmic Solution | Truvada Tablets |
| Trypsin | Tussionex Pennkinetic Extended-Release Suspension | Twinject Auto-Injector | Tygacil for Injection |
| Tykerb Tablets | Regular Strength Tylenol Tables | Tylox Capsules | Uloric Tablets |
| Ultane Liquid For Inhalation | Ultracet Tablets | Ultram Tablets | Ultram ER Extended-Release Tablets |
| Ultrase Capsules | Ultrase MT Capsules | Undecylenic Acid | Uniphyl Tablets |
| Urocit-K Tablets | Uroqid-Acid No. 2 Tablets | Uroxatral Tablets | Urso 250 Tablets |
| Urso Forte Tablets | Ursodiol | Vagifem Tablets | Valacyclovir Hydrochloride |
| Valcyte Tablets | Valcyte For Oral Solution | Valganciclovir Hydrochloride | Valium Tablets |
| Valproic Acid | Valrubicin | Valsartan | Valstar Sterile Solution For Intravesical Instillation |
| Valtrex Caplets | Valturna Tablets | Vanadium | Vantas Implant |
| Vaprisol | Vaqta | Vardenafil Hydrochloride | Varenicline Tartrate |
| Varicella Virus Vaccine, Live | Varivax | Vectribix | Velcade For Injection |
| Venlafaxine Hydrochloride | Ventolin HFA Inhalation Aerosol | Veramyst Nasal Spray | Verapamil Hydrochloride |
| Verteporfin | Vesicare Tablets | Vicodin Tablets | Vicodin ES Tablets |
| Vicodin HP Tablets | Vicoprofen Tablets | Vigabatrin | Vigamox Ophthalmic Solution |
| Vimpat Injection | Vimpat Tablets | Viokase Powder | Viokase Tablets |
| Viramune Oral Suspension | Viramune Tablets | Viread Tablets | Visudyne For Injection |
| Visutein Capsules | Vitamin A | Vitamin B1 | Vitamin B2 |
| Vitamin B6 | Vitamin B12 | Vitamin C | Vitamin D |
| Vitamin D3 | Vitamin E | Vitamin K | Vitamin K1 |
| Vitamins, Multiple | Vitamins, Prenatal | Vitamins with Minerals | *Vitis Vinifera* |
| Von Willebrand Factor (Human) | Vorinostat | Vytorin 10/10 Tablets | Vytorin 10/10 Tablets |
| Vytorin 10/20 Tablets | Vytorin 10/40 Tablets | Vytorin 10/80 Tablets | Vyvanse Capsules |
| Watchhaler | Welchol Tablets | Wellburtrin Tablets | Wellbutrin SR Sustained-Release Tablets |
| Westhroid Tablets | White Petrolatum | Winrho SDF | Xeloda Tablets |
| Xenazine Tablets | Xenical Capsules | Xifaxan Tablets | Xigris Powder For Intravenous Infusion |
| Xolair | Xolair | Xyntha Vials | Xyzal Oral Solution |
| Xyzal Oral Solution | Xyzal Tablets | Xyzal Tablets | Yarrow |
| Yaz Tablets | Yeast | Zafirlukast | Zaleplon |

TABLE 2-continued

| | | | |
|---|---|---|---|
| Zanamivir | Zantac 25 Efferdose Tablets | Zantac 150 Tablets | Zantac 300 Tablets |
| Zantac Injection | Zantac Injection Pharmacy Bulk Package | Zantac Injection Premixed | Zantac Syrup |
| Zeaxanthin | Zeel Injection Solution | Zemplar Capsules | Zemplar Injection |
| Zemuron Injection | Zetia Tablets | Zetia Tablets | Ziagen Oral Solution |
| Ziagen Tablets | Zidovudine | Zinacef For Injection | Zinacef Injection |
| Zinc | Zinc Citrate | Zinc Oxide | Zinc Sulfate |
| Zinc-220 Capsules | Ziprasidone Hydrochloride | Ziprasidone Mesylate | Zipsor 25 MG Liquid Filled Capsules |
| Zocor Tablets | Zofran Injection | Zofran Injection Premixed | Zofran Oral Solution |
| Zofran Tablets | Zofran ODT Orally Disintegrating Tablets | Zoledronic Acid | Zolinza Capsules |
| Zolmitriptan | Zolpidem Tartrate | Zometa For Intravenous Infusion | Zomig Tablets |
| Zomig Nasal Spray | Zomig-ZMT Tablets | Zonegran Capsules | Zonisamide |
| Zorbtive For Injection | Zostavax Injection | Zoster Vaccine Live | Zosyn for Injection |
| Zovirax Capsules | Zovirax Suspension | Zovirax Tablets | Zyban Sustained-Release Tablets |
| Zydone Tablets | Zyprexa Tablets | Zyprexa Intramuscular | Zyprexa Zydis Orally Disintegrating Tablets |
| Zyrtec Allergy Tablets | Zyvox For Oral Suspension | Zyvox Injection | Zyvox Tablets |

Antibiotic Compositions

In some aspects, the additional agent can be an antibiotic composition, or in other aspects the nanoconjugate itself functions as an antibiotic composition. Accordingly, in some embodiments the present disclosure provides antibiotic compositions comprising a nanoconjugate as described herein. Antibiotic compositions as part of functionalized nanoparticles are also described in PCT/US2010/020558, which is incorporated herein by reference in its entirety.

In aspects wherein the nanoconjugate comprises a polynucleotide as either a structural biomolecule or a non-structural additional agent, it is contemplated in certain aspects that the polynucleotide is sufficiently complementary to a target coding or non-coding sequence of a prokaryotic gene that it will hybridize to the target sequence under conditions that allow hybridization. In various embodiments, it is contemplated that hybridization of the nanoconjugate comprising a polynucleotide to a prokaryotic gene inhibits (or prevents) the growth of a prokaryotic cell. Thus, the hybridization of the nanoconjugate comprising a polynucleotide to a prokaryotic gene is contemplated to result in a bacteriostatic or bactericidal effect in aspects wherein the prokaryote is bacteria. In aspects wherein the hybridization occurs in vivo, the growth of the prokaryotic cell is inhibited compared to the growth of the prokaryotic cell in the absence of contact with the polynucleotide-modified nanoparticle.

In some embodiments, hybridization of the nanoconjugate comprising a polynucleotide to a prokaryotic gene inhibits expression of a functional prokaryotic protein encoded by the prokaryotic gene. A "functional prokaryotic protein" as used herein refers to a full length wild type protein encoded by a prokaryotic gene, and in certain aspects, the functional protein is essential for prokaryotic cell growth.

Prokaryotic proteins essential for growth include, but are not limited to, a gram-negative gene product, a gram-positive gene product, cell cycle gene product, a gene product involved in DNA replication, a cell division gene product, a gene product involved in protein synthesis, a bacterial gyrase, and an acyl carrier gene product. These classes are discussed in detail herein below.

The present disclosure also contemplates an antibiotic composition wherein hybridization to a target non-coding sequence of a prokaryotic gene results in expression of a protein encoded by the prokaryotic gene with altered activity. In some embodiments, the antibiotic composition hybridizes to a target non-coding sequence of a prokaryotic gene that confers a resistance to an antibiotic. These genes are known to those of ordinary skill in the art and are discussed, e.g., in Liu et al., Nucleic Acids Research 37: D443-D447, 2009 (incorporated herein by reference in its entirety). In some aspects, hybridization of the antibiotic composition to a target non-coding sequence of a prokaryotic gene that confers a resistance to an antibiotic results in increasing the susceptibility of the prokaryote to an antibiotic. In one aspect, the susceptibility of the prokaryote to the antibiotic is increased compared to the susceptibility of the prokaryote that was not contacted with the antibiotic composition. Relative susceptibility to an antibiotic can be determined by those of ordinary skill in the art using routine techniques as described herein.

Combination Therapy with Antibiotics

In some embodiments, the antibiotic composition comprising the nanoconjugate is formulated for administration in combination with an antibiotic agent, wherein both the nanoconjugate and antibiotic agent are administered in a therapeutically effective amount.

The term "antibiotic agent" as used herein means any of a group of chemical substances having the capacity to inhibit the growth of, or to kill bacteria, and other microorganisms, used chiefly in the treatment of infectious diseases. See, e.g., U.S. Pat. No. 7,638,557 (incorporated by reference herein in its entirety). Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

Biomolecule Markers/Labels

A biomolecule as described herein, in various aspects, optionally comprises a detectable label. Accordingly, the disclosure provides compositions and methods wherein biomolecule complex formation is detected by a detectable change. In one aspect, complex formation gives rise to a color change which is observed with the naked eye or spectroscopically.

Methods for visualizing the detectable change resulting from biomolecule complex formation also include any fluorescent detection method, including without limitation fluorescence microscopy, a microtiter plate reader or fluorescence-activated cell sorting (FACS).

It will be understood that a label contemplated by the disclosure includes any of the fluorophores described herein as well as other detectable labels known in the art. For example, labels also include, but are not limited to, redox active probes, chemiluminescent molecules, radioactive labels, dyes, fluorescent molecules, phosphorescent molecules, imaging and/or contrast agents as described below, quantum dots, as well as any marker which can be detected using spectroscopic means, i.e., those markers detectable using microscopy and cytometry. In aspects of the disclosure wherein a detectable label is to be detected, the disclosure provides that any luminescent, fluorescent, or phosphorescent molecule or particle can be efficiently quenched by noble metal surfaces. Accordingly, each type of molecule is contemplated for use in the compositions and methods disclosed.

Methods of labeling biomolecules with fluorescent molecules and measuring fluorescence are well known in the art.

Suitable fluorescent molecules are also well known in the art and include without limitation 1,8-ANS (1-Anilinonaphthalene-8-sulfonic acid), 1-Anilinonaphthalene-8-sulfonic acid (1,8-ANS), 5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Nissl stain-RNA, Nile Blue, EtOH, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PicoGreen dsDNA quantitation reagent, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, EtOH, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

It is also contemplated by the disclosure that, in some aspects, fluorescent polypeptides are used.

Any detectable polypeptide known in the art is useful in the methods of the disclosure, and in some aspects is a fluorescent protein. In some aspects, the fluorescent protein is selected from the list of proteins in Table 3, below.

TABLE 3

List of fluorescent polypeptides

Green Proteins

| | |
|---|---|
| EGFP | Emerald |
| CoralHue ® Azami Green | CoralHue ® Monomeric Azami Green |
| CopGFP | AceGFP |
| ZsGreen1 | TagGFP |
| TurboGFP | mUKG |

Blue/UV Proteins

| | |
|---|---|
| EBFP | TagBFP |
| Azurite | EBFP2 |
| mKalama1 | GFPuv |
| Sapphire | T-Sapphire |

Cyan Proteins

| | |
|---|---|
| ECFP | Cerulean |
| AmCyan1 | CoralHue ® Midoriishi-Cyan |
| TagCFP | mTFP1 |

Yellow Proteins

| | |
|---|---|
| EYFP | Citrine |
| Venus | PhiYFP |
| TagYFP | Turbo YFP |
| ZsYellow1 | |

Orange Proteins

| | |
|---|---|
| CoralHue ® Kusabira-Orange | CoralHue ® Monomeric Kusabira-Orange |
| mOrange | mKOκ |

Red Proteins

| | |
|---|---|
| TurboFP602 | tdimer2(12) |
| mRFP1 | DsRed-Express |
| DsRed2 | DsRed-Monomer |
| HcRed1 | AsRed2 |
| eqFP611 | mRaspberry |
| mCherry | mStrawberry |
| mTangerine | tdTomato |
| TagRFP | JRed |

Far Red Proteins

| | |
|---|---|
| TurboFP635 | mPlum |
| AQ143 | TagFP635 |
| HcRed-Tandem | |

Large Stokes Shift Proteins

| | |
|---|---|
| CoralHue ® mKeima Red | CoralHue ® dKeima Red |
| CoralHue ® dKeima570 | |

Photoconvertible Proteins

| | |
|---|---|
| CoralHue ® Dronpa | CoralHue ® Kaede (green) |
| CoralHue ® Kaede (red) | CoralHue ® KikGR1 (green) |
| CoralHue ® KikGR1 (red) | KFP-Red |
| PA-GFP | PS-CFP |
| PS-CFP | mEosFP |
| mEosFP | |

Contrast Agents

Disclosed herein are, in various aspects, methods and compositions comprising a nanoconjugate, wherein the biomolecule is a polynucleotide, and wherein the polynucleotide is conjugated to a contrast agent through a conjugation site. In further aspects, a contrast agent is conjugated to any other biomolecule as described herein. As used herein, a "contrast agent" is a compound or other substance introduced into a cell in order to create a difference in the apparent density of various organs and tissues, making it easier to see the delineate adjacent body tissues and organs. It will be understood that conjugation of a contrast agent to any biomolecule described herein is useful in the compositions and methods of the disclosure.

Methods provided by the disclosure include those wherein relaxivity of the contrast agent in association with a nanoconjugate is increased relative to the relaxivity of the contrast agent in the absence of being associated with a nanoparticle. In some aspects, the increase is about 1-fold to about 20-fold. In further aspects, the increase is about 2-fold fold to about 10-fold, and in yet further aspects the increase is about 3-fold.

In some embodiments, the contrast agent is selected from the group consisting of gadolinium, xenon, iron oxide, a manganese chelate (Mn-DPDP) and copper. Thus, in some embodiments the contrast agent is a paramagnetic compound, and in some aspects, the paramagnetic compound is gadolinium.

The present disclosure also contemplates contrast agents that are useful for positron emission tomography (PET) scanning. In some aspects, the PET contrast agent is a radionuclide. In certain embodiments the contrast agent comprises a PET contrast agent comprising a label selected from the group consisting of $^{11}$C, $^{13}$N, $^{18}$F, $^{64}$Cu, $^{68}$Ge, $^{99m}$Tc and $^{82}$Ru. In particular embodiments the contrast agent is a PET contrast agent selected from the group consisting of [$^{11}$C] choline, [$^{18}$F]fluorodeoxyglucose(FDG), [$^{11}$C]methionine, [$^{11}$C]choline, [$^{11}$C]acetate, [$^{18}$F]fluorocholine, $^{64}$Cu chelates, $^{99m}$Tc chelates, and [$^{18}$F]polyethyleneglycol stilbenes.

The disclosure also provides methods wherein a PET contrast agent is introduced into a polynucleotide during the polynucleotide synthesis process or is conjugated to a nucleotide following polynucleotide synthesis. For example and without limitation, nucleotides can be synthesized in which one of the phosphorus atoms is replaced with $^{32}$P or $^{33}$P one of the oxygen atoms in the phosphate group is replaced with $^{35}$S, or one or more of the hydrogen atoms is replaced with $^{3}$H. A functional group containing a radionuclide can also be conjugated to a nucleotide through conjugation sites.

The MRI contrast agents can include, but are not limited to positive contrast agents and/or negative contrast agents. Positive contrast agents cause a reduction in the $T_1$ relaxation time (increased signal intensity on $T_1$ weighted images). They (appearing bright on MRI) are typically small molecular weight compounds containing as their active element Gadolinium, Manganese, or Iron. All of these elements have unpaired electron spins in their outer shells and long relaxivities. A special group of negative contrast agents (appearing dark on MRI) include perfluorocarbons (perfluorochemicals), because their presence excludes the hydrogen atoms responsible for the signal in MR imaging.

The composition of the disclosure, in various aspects, is contemplated to comprise a nanoconjugate that comprises about 50 to about $2.5 \times 10^6$ contrast agents. In some embodiments, the nanoconjugate comprises about 500 to about $1 \times 10^6$ contrast agents.

Targeting Moiety

The term "targeting moiety" as used herein refers to any molecular structure which assists a compound or other molecule in binding or otherwise localizing to a particular target, a target area, entering target cell(*s*), or binding to a target receptor. For example and without limitation, targeting moieties may include proteins, including antibodies and protein fragments capable of binding to a desired target site in vivo or in vitro, peptides, small molecules, anticancer agents, polynucleotide-binding agents, carbohydrates, ligands for cell surface receptors, aptamers, lipids (including cationic, neutral, and steroidal lipids, virosomes, and liposomes), antibodies, lectins, ligands, sugars, steroids, hormones, and nutrients, may serve as targeting moieties. Targeting moieties are useful for delivery of the nanoconjugate to specific cell types and/or organs, as well as sub-cellular locations.

In some embodiments, the targeting moiety is a protein. The protein portion of the composition of the present disclosure is, in some aspects, a protein capable of targeting the composition to target cell. The targeting protein of the present disclosure may bind to a receptor, substrate, antigenic determinant, or other binding site on a target cell or other target site.

Antibodies useful as targeting proteins may be polyclonal or monoclonal. A number of monoclonal antibodies (MAbs) that bind to a specific type of cell have been developed. Antibodies derived through genetic engineering or protein engineering may be used as well.

The antibody employed as a targeting agent in the present disclosure may be an intact molecule, a fragment thereof, or a functional equivalent thereof. Examples of antibody fragments useful in the compositions of the present disclosure are F(ab')$_2$, Fab' Fab and Fv fragments, which may be produced by conventional methods or by genetic or protein engineering.

In some embodiments, the polynucleotide portion of the nanoconjugate may serve as an additional or auxiliary targeting moiety. The polynucleotide portion may be selected or designed to assist in extracellular targeting, or to act as an intracellular targeting moiety. That is, the polynucleotide portion may act as a DNA probe seeking out target cells. This additional targeting capability will serve to improve specificity in delivery of the composition to target cells. The polynucleotide may additionally or alternatively be selected or designed to target the composition within target cells, while the targeting protein targets the conjugate extracellularly.

It is contemplated that the targeting moiety can, in various embodiments, be associated with a nanoconjugate. In aspects wherein the nanoconjugate comprises a nanoparticle, it is contemplated that the targeting moiety is attached to either the nanoparticle, the biomolecule or both. In further aspects, the targeting moiety is associated with the nanoconjugate composition, and in other aspects the targeting moiety is administered before, concurrent with, or after the administration of a composition of the disclosure.

Short Internal Complementary Polynucleotide (sicPN)

In some aspects, the additional agent is a sicPN. A sicPN is a polynucleotide that associates with a polynucleotide that is part of a nanoconjugate, and that is displaced and/or released when a target polynucleotide hybridizes to the polynucleotide that is part of the nanoconjugate. In one aspect, the sicPN has a lower binding affinity or binding avidity for the polynucleotide that is part of the nanoconjugate such that association of the target molecule with the polynucleotide that is part of the nanoconjugate causes the sicPN to be displaced and/or released from its association with the polynucleotide that is part of the nanoconjugate.

"Displace" as used herein means that a sicPN is partially denatured from its association with a polynucleotide. A displaced sicPN is still in partial association with the polynucleotide to which it is associated. "Release" as used herein means that the sicPN is sufficiently displaced (i.e., completely denatured) so as to cause its disassociation from the polynucleotide to which it is associated. In some aspects wherein the sicPN comprises a detectable marker, it is contemplated that the release of the sicPN causes the detectable marker to be detected.

Methods for detecting a target molecule using a sicPN are described herein below.

Transcriptional Regulators

The present disclosure provides compositions comprising a nanoconjugate. In some aspects, the nanoconjugate comprises a polynucleotide, wherein the polynucleotide further comprises a transcriptional regulator. In these aspects, the transcriptional regulator induces transcription of a target polynucleotide in a target cell.

A transcriptional regulator as used herein is contemplated to be anything that induces a change in transcription of a mRNA. The change can, in various aspects, either be an increase or a decrease in transcription. In various embodiments, the transcriptional regulator is selected from the group consisting of a polypeptide, a polynucleotide, an artificial transcription factor (ATF) and any molecule known or suspected to regulate transcription.

Compositions and methods of the disclosure include those wherein the transcriptional regulator is a polypeptide. Any polypeptide that acts to either increase or decrease transcription of a mRNA is contemplated for use herein. A peptide is also contemplated for use as a transcriptional regulator.

In some embodiments, the polypeptide is a transcription factor. In general, a transcription factor is modular in structure and contain the following domains.

DNA-binding domain (DBD), which attach to specific sequences of DNA (for example and without limitation, enhancer or promoter sequences) adjacent to regulated genes. DNA sequences that bind transcription factors are often referred to as response elements.

Trans-activating domain (TAD), which contain binding sites for other proteins such as transcription co-regulators. These binding sites are frequently referred to as activation functions (AFs) [Wärnmark et al., Mol. Endocrinol. 17(10): 1901-9 (2003)].

An optional signal sensing domain (SSD) (for example and without limitation, a ligand binding domain), which senses external signals and, in response, transmits these signals to the rest of the transcription complex, resulting in up- or down-regulation of gene expression. Also, the DBD and signal-sensing domains may, in some aspects, reside on separate proteins that associate within the transcription complex to regulate gene expression.

Regulator Polynucleotides

In some embodiments, the transcription factor is a regulator polynucleotide. In certain aspects, the polynucleotide is RNA, and in further aspects the regulator polynucleotide is a noncoding RNA (ncRNA).

In some embodiments, the noncoding RNA interacts with the general transcription machinery, thereby inhibiting transcription [Goodrich et al., Nature Reviews Mol Cell Biol 7: 612-616 (2006)]. In general, RNAs that have such regulatory functions do not encode a protein and are therefore referred to as ncRNAs. Eukaryotic ncRNAs are transcribed from the genome by one of three nuclear, DNA-dependent RNA polymerases (Pol I, II or III). They then elicit their biological responses through one of three basic mechanisms: catalyzing biological reactions, binding to and modulating the activity of a protein, or base-pairing with a target nucleic acid.

ncRNAs have been shown to participate actively in many of the diverse biological reactions that encompass gene expression, such as splicing, mRNA turn over, gene silencing and translation [Storz, et al., Annu. Rev. Biochem. 74: 199-217 (2005)]. Notably, several studies have recently revealed that ncRNAs also actively regulate eukaryotic mRNA transcription, which is a key point for the control of gene expression.

In another embodiment, a regulatory polynucleotide is one that can associate with a transcription factor thereby titrating its amount. In some aspects, using increasing concentrations of the regulatory polynucleotide will occupy increasing amounts of the transcription factor, resulting in derepression of transcription of a mRNA.

In a further embodiment, a regulatory polynucleotide is an aptamer.

Coating

The coating can be any substance that is a degradable polymer, biomolecule or chemical that is non toxic. Alternatively, the coating can be a bioabsorbable coating. As used herein, "coating" refers to the components, in total, that are deposited on a nanoconjugate. The coating includes all of the coated layers that are formed on the nanoconjugate. A "coated layer" is formed by depositing a compound, and more typically a composition that includes one or more compounds suspended, dissolved, or dispersed, in a particular solution. As used herein, the term "biodegradable" or "degradable" is defined as the breaking down or the susceptibility of a material or component to break down or be broken into products, byproducts, components or subcomponents over time such as minutes, hours, days, weeks, months or years. As used herein, the term "bioabsorbable" is defined as the biologic elimination of any of the products of degradation by metabolism and/or excretion.

A non-limiting example of a coating that is a biodegradable and/or bioabsorbable material is a bulk erodible polymer (either a homopolymer, copolymer or blend of polymers) such as any one of the polyesters belonging to the poly(alpha-hydroxy acids) group. This includes aliphatic polyesters such poly(lactic acid); poly(glycolic acid); poly(caprolactone); poly(p-dioxanone) and poly(trimethylene carbonate); and their copolymers and blends. Other polymers useful as a bioabsorbable material include without limitation amino acid derived polymers, phosphorous containing polymers, and poly(ester amide). The rate of hydrolysis of the biodegradable and/or bioabsorbable material depends on the type of monomer used to prepare the bulk erodible polymer. For example, the absorption times (time to complete degradation or fully degrade) are estimated as follows: poly(caprolactone) and poly(trimethylene carbonate) takes more than 3 years; poly(lactic acid) takes about 2 years; poly(dioxanone) takes about 7 months; and poly(glycolic acid) takes about 3 months. Absorption rates for copolymers prepared from the monomers such as poly(lactic acid-co-glycolic acid); poly(glycolic acid-co-caprolactone); and poly(glycolic acid-co-trimethylene carbonate) depend on the molar amounts of the monomers.

The nanoconjugates may also be administered by other controlled-release means or delivery devices that are well known to those of ordinary skill in the art. These include, for example and without limitation, hydropropylmethyl cellulose, other polymer matrices, gels, permeable membranes, multilayer coatings (see below), liposomes, or a combination of any of the above to provide the desired release profile in varying proportions. Other methods of controlled-release delivery of compounds will be known to the skilled artisan and are within the scope of the invention.

Methods

Methods of Making a Nanoconjugate

The present disclosure provides strategies for crosslinking biomolecules on a nanoparticle. In one aspect, the strategy involves the use of alkyne-bearing ligands. These ligands self assemble on to the surface of gold nanoparticles, and the alkyne moieties of these ligands are activated by the gold surface for reaction with nucleophiles present within the ligand shell. This crosslinking reaction is suitable for formation of hollow nanoconjugates with any desired surface functionality. Furthermore, any biomolecule or non-biomolecule that can be attached to a polyalkyne or monoalkyne moiety will be incorporated into this ligand shell or form a ligand shell independently Biomolecule Crosslinking Poly Alkyne Chemistry Au(I) and Au(III) ions and their complexes display remarkable alkynophilicity, and have been increasingly recognized as potent catalysts for organic transformations [Hashmi, Chem. Rev. 107: 3180-3211 (2007); Li et al., Chem. Rev. 108: 3239 (2008); Fürstner et al., Angew. Chem. Int. Ed. 46: 3410 (2007); Hashmi et al., Angew. Chem. Int. Ed. 45: 7896 (2006)]. Recently, it has been demonstrated that Au(0) surfaces also adsorb terminal acetylene groups and form relatively densely packed and stable monolayers [Zhang et al., J. Am. Chem. Soc. 129: 4876 (2006)]. However, the type of interaction that exists between the alkyne and the gold surface is not well understood.

Moreover, it is not clear whether such interaction makes the acetylene group more susceptible to chemical reactions, such as nucleophilic additions typically observed with ionic gold-alkyne complexes. Bearing multiple side-arm propargyl ether groups, polymer 1 (Scheme 1) readily adsorbs onto citrate-stabilized 13 nm AuNPs prepared in an aqueous solution following the Turkevich-Frens method [Frens, Coll. Polym. Sci. 250: 736 (1972)]. Excess polymer is removed by iterative centrifugation and subsequent resuspension steps. The resulting polymer-coated AuNPs exhibit a plasmon resonance at 524 nm characteristic of dispersed particles, and there is no evidence of aggregation even after 8 weeks of storage at room temperature. Therefore, even though 1 is a potential inter-particle crosslinking agent, it does not lead to aggregation of the AuNPs, a conclusion that was corroborated by Dynamic Light Scattering (DLS) and electron microscopy (see Examples below).

In one embodiment, the disclosure provides a method for synthesizing nanoconjugates from a linear biomolecule bearing pendant propargyl ether groups (1), utilizing gold nanoparticles (AuNPs) as both the template for the formation of the shell and the catalyst for the crosslinking reaction (Scheme 1). No additional crosslinking reagents or synthetic operations are required. The reaction yields well-defined, homogeneous hollow nanoconjugates when the nanoparticle is removed after the biomolecules are crosslinked.

Scheme 1. Synthesis of polyvalent propargyl ether nanoconjugates.

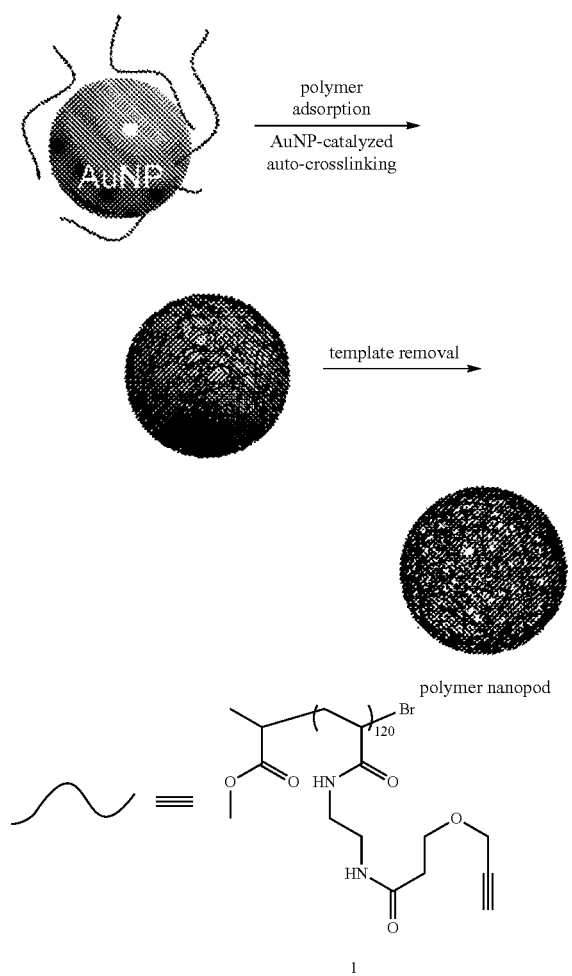

In one aspect, the biomolecule is a polynucleotide as defined herein. In these aspects, it is contemplated that the polynucleotide comprises an alkyne. In various embodiments, from 1 to 100 alkyne moieties are present on a polynucleotide. In further aspects, from about 5 to about 50 alkyne moieties, or about 10 to about 20 alkyne moieties are present on a polynucleotide. In one aspect, 10 alkyne moieties are present on the polynucleotide. In further aspects, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more alkyne moieties are present on a polynucleotide.

In another embodiment, the alkyne moieties on a polynucleotide are on the 5' end. In a further embodiment, the alkyne moieties on a polynucleotide are on the 3' end. It is contemplated that in some aspects the alkyne moieties represent only a portion of the length of a polynucleotide. By way of example, if a polynucleotide is 20 nucleotides in length, then it is contemplated that the first 10 nucleotides (counting, in various aspects from either the 5' or 3' end) comprise an alkyne moiety. Thus, 10 nucleotides comprising an alkyne moiety out of a total of 20 nucleotides results in 50% of the nucleotides in a polynucleotide being associated with an alkyne moiety. In various aspects it is contemplated that from about 0.01% to about 100% of the nucleotides in a polynucleotide are associated with an alkyne moiety. In further aspects, about 1% to about 70%, or about 2% to about 60%, or about 5% to about 50%, or about 10% to about 50%, or about 10% to about 40%, or about 20% to about 50%, or about 20% to about 40% of nucleotides in a polynucleotide are associated with an alkyne moiety. In still further aspects it is contemplated that about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% of nucleotides in a polynucleotide are associated with an alkyne moiety.

Figure 16:
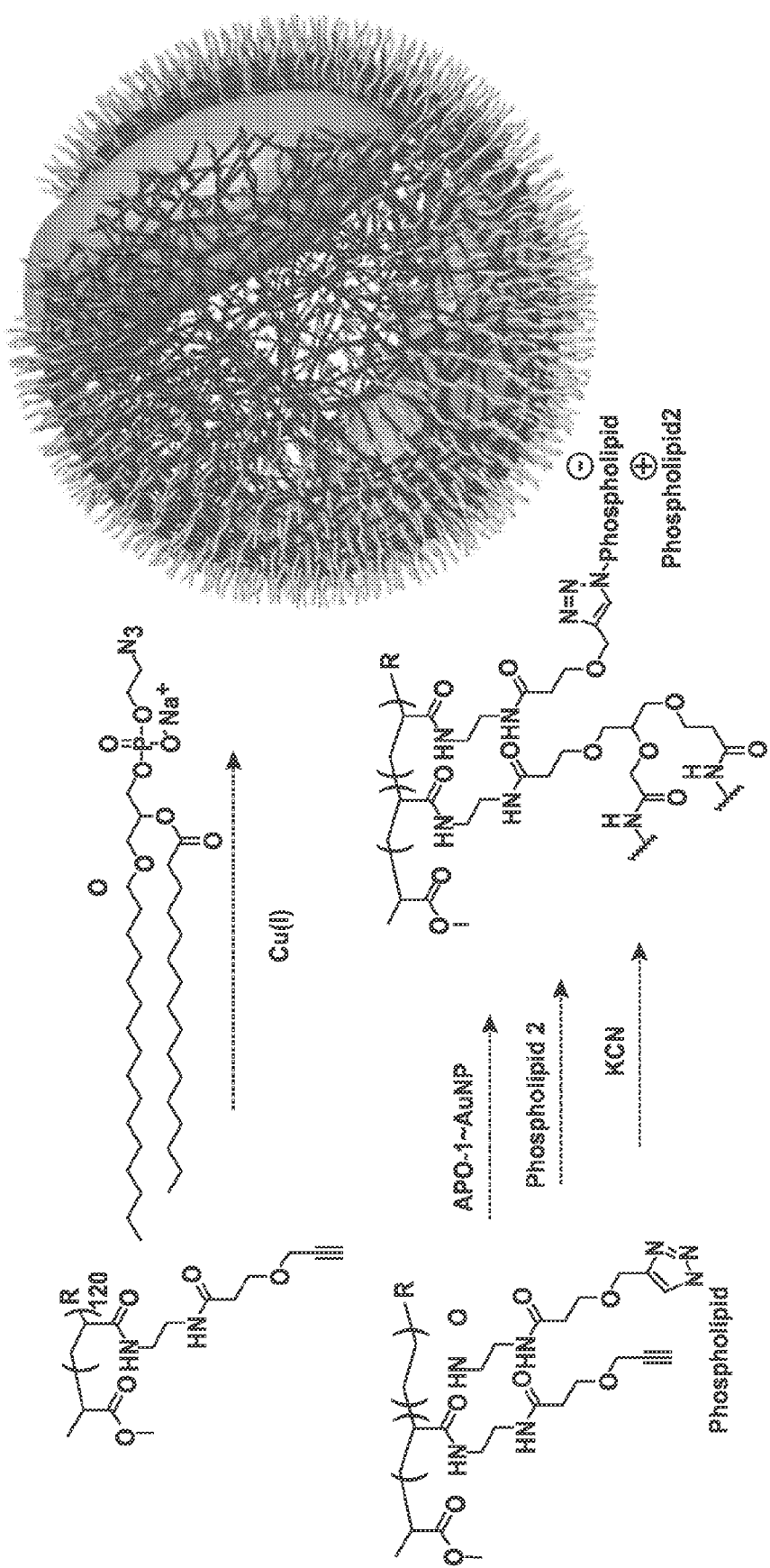
FIG. 16 depicts a potential pathway for formation of hollow HDL nanoparticles by using an alkyne moiety and a phospholipid-bearing polymer and APO1A proteins.

In one aspect, this crosslinking reaction can be utilized in the formation of hollow HDL nanoparticles by using an alkyne moiety and a phospholipid-bearing polymer and APO1A proteins (FIG. 16).

Returning to methods of carrying out the crosslinking using a poly alkyne crosslinking approach, the following steps are involved. First, a solution of nanoparticles is prepared (Nanoparticle preparation step) as described herein (Example 1). The solution is brought into contact with a solution comprising biomolecules comprising a poly-reactive group (Contacting step). Depending on the poly reactive group used, an optional activation step is included (Activation step). The resulting mixture is then incubated to allow the crosslinking to occur (Incubation step), and is then isolated (Isolation step). An optional dissolution of the nanoparticle core (Dissolution step) is then carried out to create a hollow nanoconjugate. A labeling step is also optionally included (Labeling step).

Nucleophiles contemplated for use by the disclosure include those described herein. In general, nucleophiles contemplated for use can be classified into carbon nucleophiles, HX nucleophiles (for example and without limitation, HF and HCl), oxygen and sulfur nucleophiles, and nitrogen nucleophiles. Any tandem combination of the above is also contemplated.

Nanoparticle Preparation Step. A solution of nanoparticles is prepared as described in Example 1. In the case of poly alkyne crosslinking, a gold nanoparticle solution is prepared in one aspect.

Contacting step. Biomolecules of interest, which either comprises a poly-reactive group or are modified to contain a poly-reactive group, are contacted with the nanoparticle solution. As used herein, a poly reactive group can be an alkyne, or the poly reactive group can be a light-reactive group, or a group that is activated upon, for example and without limitation, sonication or microwaves. Regardless of the poly reactive group that is used, the solution of biomolecules comprising the poly reactive groups is contacted with the nanoparticle solution to facilitate the crosslinking.

In some aspects, and regardless of the crosslinking strategy that is used, the amount of biomolecules to add relates to the property of the resulting nanoconjugate. In general, the disclosure provides nanoconjugates that are either more or less dense, depending on the concentration of biomolecules used to crosslink to the nanoconjugate. A lower concentration of biomolecules will result in a lower density on the nanoparticle, which will result in a more porous nanoconjugate. Conversely, a higher concentration of biomolecules will result in a higher density on the nanoparticle, which will result in a more rigid nanoconjugate. As it pertains to these aspects, a "lower density" is from about 2 pmol/cm$^2$ to about 100 pmol/cm$^2$. Also as pertains to these aspects, a "higher density" is from about 101 pmol/cm$^2$ to about 1000 pmol/cm$^2$.

Activation Step. In aspects of the disclosure wherein a poly reactive group present on a biomolecule and/or non-biomolecule requires activation, it is contemplated that an activation step is included in the methods. In this step, the source of activation is applied and can be, without limitation, a laser (when the poly reactive group is light reactive), or sound (when the poly reactive group is activated by sonication), or a microwave (when the poly reactive group is activated by microwaves).

In some embodiments, the surface itself can activate the poly reactive group present on a biomolecule and/or non-biomolecule. In these embodiments, the activation step is not required.

Incubation Step. Once the solution comprising the biomolecules comprising poly reactive groups is brought into contact with the nanoparticle solution, the mixture is incubated to allow crosslinking to occur. Incubation can occur at a temperature from about 4° C. to about 50° C. The incubation is allowed to take place for a time from about 1 minute to about 48 hours or more. It is contemplated that in some aspects the incubation can occur without regard to length of time.

Isolation Step. The crosslinked nanoconjugate can then be isolated. For isolation, the mixture is centrifuged, the supernatant is removed and the crosslinked nanoconjugates are resuspended in an appropriate buffer. In various aspects, more than one centrifugation step may be carried out to further purify the crosslinked nanoconjugates.

Dissolution Step. In any of the compositions or methods described herein, whether to retain the nanoparticle following the crosslinking of the biomolecules is optional and dependent of the intended use.

In those embodiments wherein a composition of the disclosure does not comprise a nanoparticle, it is contemplated that the nanoparticle is dissolved or otherwise removed following the crosslinking of the biomolecules to the nanoconjugate.

Dissolution of a nanoparticle core is within the ordinary skill in the art, and in one aspect is achieved by using KCN in the presence of oxygen. In further aspects, iodine or Aqua regia is used to dissolve a nanoparticle core. In one aspect, the nanoparticle core comprises gold. As described herein, when KCN is added to citrate stabilized AuNPs, the color of the solution changes from red to purple, resulting from the destabilization and aggregation of the AuNPs. However, for a polymer-coated AuNP, the color slowly changes to a slightly reddish orange color during the dissolution process until the solution is clear (FIG. 9A).

Figure 9:
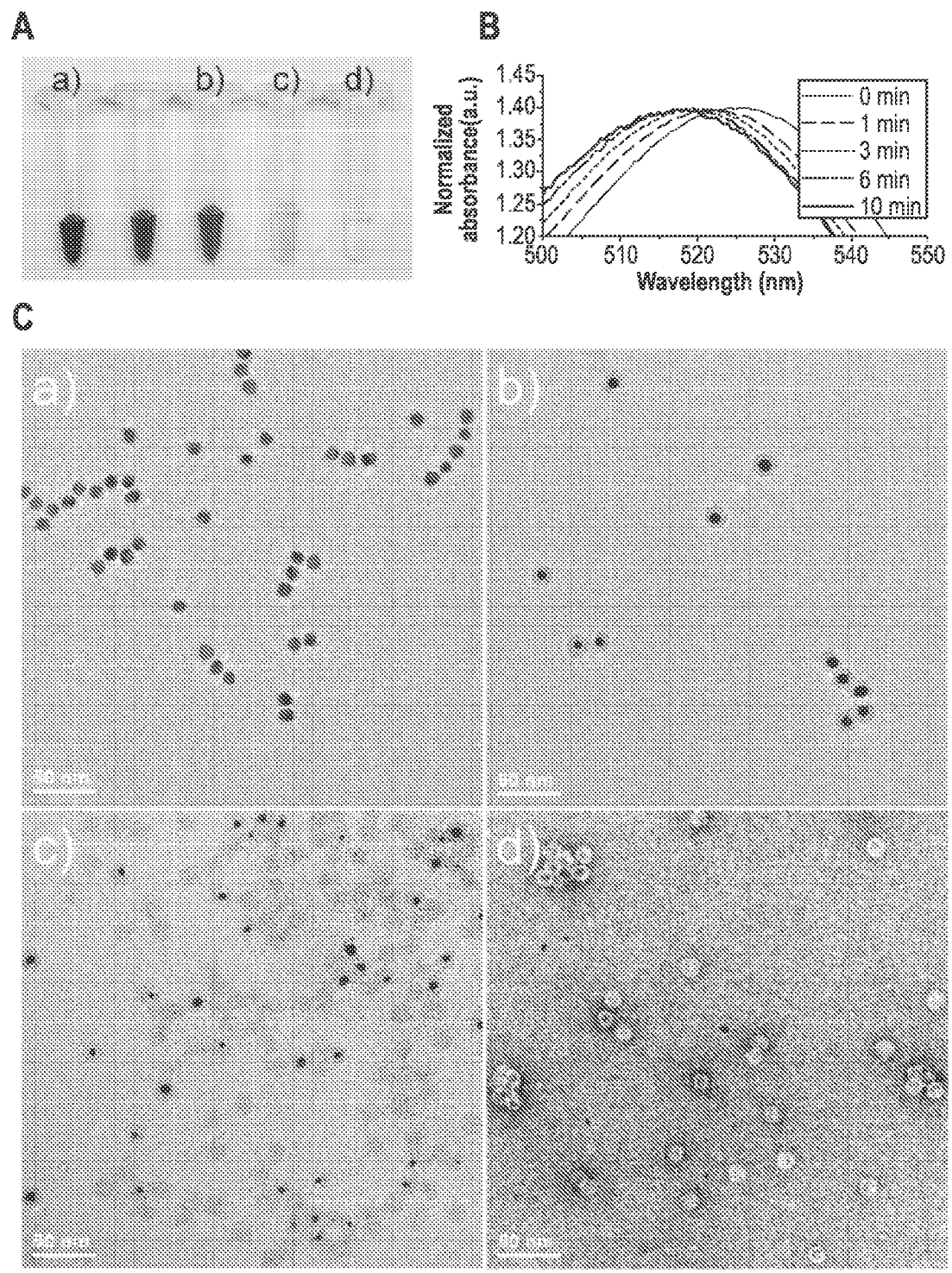
FIG. 9 shows A) Dissolution process of polymer-coated 13 nm AuNP. B) Normalized UV-Vis spectra of AuNP at various time points during the dissolution. C) TEM images of a) polymer-coated AuNP, b-c) partially formed nanoconjugates and d) fully formed nanoconjugates (negatively stained with 0.5% uranyl acetate).

The dissolution process can be visualized by transmission electron microscopy (TEM) (FIG. 9C). As the outer layer of the AuNP is partially dissolved, the protective shell mentioned above can be observed with uranyl-acetate staining of the TEM grid. Complete removal of the template affords hollow nanoconjugates that retain the size and shape of their template in high fidelity.

Additional Crosslinking Methods

Direct strand crosslinking (DSC) is a method whereby one or more nucleotides of a polynucleotide is modified with one or more crosslinking moieties that can be cross-linked through chemical means. The DSC method, in one aspect, is effected through the modification of one or more nucleotides of a polynucleotide with a moiety that can be crosslinked through a variety of chemical means. In various aspects, the one or more nucleotides that comprise the crosslinking moieties are in the spacer.

In an aspect, polynucleotides are synthesized that incorporate an amine-modified thymidine phosphoramidite (TN) into the spacer. The polynucleotide can consist entirely of this modified base to maximize cross-linking efficiency. The strands are crosslinked in one aspect with the use of a homobifunctional cross-linker like Sulfo-EGS, which has two amine reactive NHS-ester moities. Although amines are contemplated for use in one embodiment, this design is compatible with many other reactive groups (for example and without limitation, amines, amides, alcohols, esters, aldehydes, ketones, thiols, disulfides, carboxylic acids, phenols, imidazoles, hydrazines, hydrazones, azides, and alkynes).

An additional method, called surface assisted crosslinking (SAC), comprises a mixed monolayer of modified nucleic acids and reactive thiolated molecules that are assembled on the nanoparticle surface and crosslinked together.

The chemical that causes crosslinking of the biomolecules of interest are known to those of skill in the art, and include without limitation Disuccinimidyl glutarate, Disuccinimidyl suberate, Bis[sulfosuccinimidyl] suberate, Tris-succinimidyl aminotriacetate, succinimidyl 4-hydrazinonicotinate acetone hydrazone, succinimidyl 4-hydrazidoterephthalate hydrochloride, succinimidyl 4-formylbenzoate, Dithiobis[succinimidyl propionate], 3,3'-Dithiobis[sulfosuccinimidylpropionate], Disuccinimidyl tartarate, Bis[2-(succinimidooxycarbonyloxy)ethyl]sulfone, Ethylene glycol bis[succinimidylsuccinate], Ethylene glycol bis[sulfosuccinimidylsuccinate], Dimethyl adipimidate.2 HCl, Dimethyl pimelimidate.2 HCl, Dimethyl Suberimidate.2 HCl, 1,5-Difluoro-2,4-dinitrobenzene, β-[Tris(hydroxymethyl)phosphino]propionic acid, Bis-Maleimidoethane, 1,4-bismaleimidobutane, Bismaleimidohexane, Tris[2-maleimidoethyl]amine, 1,8-Bis-maleimido-diethyleneglycol, 1,11-Bis-maleimido-triethyleneglycol, 1,4 bismaleimidyl-2,3-dihydroxybutane, Dithio-bismaleimidoethane, 1,4-Di-[3'-(2'-pyridyldithio)-propionamido]butane, 1,6-Hexane-bis-vinylsulfone, Bis-[b-(4-Azidosalicylamido)ethyl]disulfide, N-(a-Maleimidoacetoxy) succinimide ester, N-[β-Maleimidopropyloxy]succinimide ester, N-[g-Maleimidobutyryloxy]succinimide ester, N-[g-Maleimidobutyryloxy]sulfosuccinimide ester, m-Maleimidobenzoyl-N-hydroxysuccinimide ester, m-Maleimidobenzoyl-N-hydroxysulfosuccinimide ester, Succinimidyl 4-[N-maleimidomethyl]cyclohexane-1-carboxylate, Sulfosuccinimidyl 4-[N-maleimidomethyl]cyclohexane-1-carboxylate, N-e-Maleimidocaproyloxy]succinimide ester, N-e-Maleimidocaproyloxy]sulfosuccinimide ester, Succinimidyl 4-[p-maleimidophenyl]butyrate, Sulfosuccinimidyl 4-[p-maleimidophenyl]butyrate, Succinimidyl-6-[β-maleimidopropionamido]hexanoate, Succinimidyl-4-[N-Maleimidomethyl]cyclohexane-1-carboxy-[6-amidocaproate], N-[k-Maleimidoundecanoyloxy]

sulfosuccinimide ester, N-Succinimidyl 3-(2-pyridyldithio)-propionate, Succinimidyl 6-(3-[2-pyridyldithio]-propionamido)hexanoate, 4-Succinimidyloxycarbonyl-methyl-a-[2-pyridyldithio]toluene, 4-Sulfosuccinimidyl-6-methyl-a-(2-pyridyldithio)toluamido]hexanoate), N-Succinimidyl iodoacetate, Succinimidyl 3-[bromoaceta-mido]propionate, N-Succinimidyl[4-iodoacetyl]aminoben-zoate, N-Sulfosuccinimidyl[4-iodoacetyl]aminobenzoate, N-Hydroxysuccinimidyl-4-azido salicylic acid, N-5-Azido-2-nitrobenzoyloxysuccinimide, N-Hydroxysulfosuccinim-idyl-4-azidobenzoate, Sulfosuccinimidyl[4-azidosalicyla-mido]-hexanoate, N-Succinimidyl-6-(4'-azido-2'-nitrophenylamino) hexanoate, N-Sulfosuccinimidyl-6-(4'-azido-2'-nitrophenylamino) hexanoate, Sulfosuccinimidyl-(perfluoroazidobenzamido)-ethyl-1,3'-dithioproprionate, Sulfosuccinimidyl-2-(m-azido-o-nitrobenzamido)-ethyl-1,3'-proprionate, Sulfosuccinimidyl 2-[7-amino-4-methylcou-marin-3-acetamido]ethyl-1,3'dithiopropionate, Succinim-idyl 4,4'-azipentanoate, Succinimidyl 6-(4,4'-azipentanamido)hexanoate, Succinimidyl 2-([4,4'-azipentanamido]ethyl)-1,3'-dithioproprionate, Sulfosuccinimidyl 4,4'-azipentanoate, Sulfosuccinimidyl 6-(4,4'-azipentanamido)hexanoate, Sulfosuccinimidyl 2-([4,4'-azipentanamido]ethyl)-1,3'-dithioproprionate, Dicyclo-hexylcarbodiimide, 1-Ethyl-3-[3-dimethylaminopropyl]car-bodiimide Hydrochloride, N-[4-(p-Azidosalicylamido) butyl]-3'-(2'-pyridyldithio)propionamide, N-[β-Maleimi-dopropionic acid] hydrazide, trifluoroacetic acid salt, [N-e-Maleimidocaproic acid]hydrazide, trifluoroacetic acid salt, 4-(4-N-Maleimidophenyl)butyric acid hydrazide hydrochlo-ride, N-[k-Maleimidoundecanoic acid]hydrazide, 3-(2-Py-ridyldithio)propionyl hydrazide, p-Azidobenzoyl hydrazide, N-[p-Maleimidophenyl]isocyanate, and Succinimidyl-[4-(psoralen-8-yloxy)]-butyrate.

DSC and SAC crosslinking of biomolecules has been generally discussed above. Steps of the methods for these crosslinking strategies will largely mirror those recited above for poly alkyne crosslinking, except the activation step will not be optional for these crosslinking strategies. As described herein, a chemical is used to facilitate the crosslinking of biomolecules. Thus, a nanoparticle preparation step, a contacting step, activation step, incubation step, isolation step and optional dissolution step are carried out. A labeling step is optionally included as well. These steps have been described herein above.

The above methods also optionally include a step wherein the nanoconjugates further comprise an additional agent as defined herein. The additional agent can, in various aspects be added to the mixture during crosslinking of the biomolecules and/or non-biomolecules, or can be added after production of the nanoconjugate.

Attachment of a Therapeutic Agent

The disclosure provides, in some embodiments, nanoconjugate compositions wherein the composition further comprises a therapeutic agent. The therapeutic agent is, in some aspects, attached to a biomolecule that is part of the nanoconjugate composition. In further aspects, the biomolecule is a polynucleotide. Methods of attaching a therapeutic agent or a chemotherapeutic agent to a polynucleotide are known in the art, and are described in Priest, U.S. Pat. No. 5,391,723, Arnold, Jr., et al., U.S. Pat. No. 5,585,481, Reed et al., U.S. Pat. No. 5,512,667 and PCT/US2006/022325, the disclosures of which are incorporated herein by reference in their entirety.

It will be appreciated that, in various aspects, a therapeutic agent as described herein is attached to the nanoparticle.

Methods Of Using A Nanoconjugate

Methods of Using a Hollow Nanoconjugate

Hollow nanoconjugates are useful, in some embodiments, as a delivery vehicle. Thus, a hollow nanoconjugate is made wherein, in one aspect, an additional agent as defined herein is localized inside the nanoconjugate. In related aspects, the additional agent is associated with the nanoconjugate as described herein. It is contemplated that the nanoconjugate that is utilized as a delivery vehicle is, in some aspects, made more porous, so as to allow placement of the additional agent inside the nanoconjugate. Porosity of the nanoconjugate can be empirically determined depending on the particular application, and is within the skill in the art. All of the advantages of the functionalized nanoparticle (for example and without limitation, increased cellular uptake and resistance to nuclease degradation) are imparted on the hollow nanoconjugate.

It is further contemplated that in some aspects the nanoconjugate used as a delivery vehicle is produced with a biomolecule that is at least partially degradable, such that once the nanoconjugate is targeted to a location of interest, it dissolves or otherwise degrades in such a way as to release the additional agent. Biomolecule degradation pathways are known to those of skill in the art and can include, without limitation, nuclease pathways, protease pathways and ubiquitin pathways.

In some aspects, a composition of the disclosure acts as a sustained-release formulation. In these aspects, the nanoconjugate is produced using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition [Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41, incorporated by reference herein in its entirety].

Methods of Increasing Hybridization Rate

In some embodiments, the biomolecule attached to a nanoparticle is a polynucleotide. Accordingly, methods provided include those that enable an increased rate of association of a polynucleotide with a target polynucleotide through the use of a sicPN. The increase in rate of association is, in various aspects, from about 2-fold to about 100-fold relative to a rate of association in the absence of a sicPN. According to the disclosure, the polynucleotide that associates with the target polynucleotide is part of a nanoconjugate. Additionally, a sicPN is added that overlaps with a portion of the target polynucleotide binding site on the polynucleotide used to produce the nanoconjugate, but not the complete sequence. Thus, there remains a single stranded portion of the polynucleotide that is part of the nanoconjugate. When the target polynucleotide associates with the single stranded portion of the polynucleotide that is part of the nanoconjugate, it displaces and/or releases the sicPN and results in an enhanced association rate of the polynucleotide that is part of the nanoconjugate with the target polynucleotide.

The association of the polynucleotide with the target polynucleotide additionally displaces and, in some aspects, releases the sicPN. The sicPN or the target polynucleotide, in various embodiments, further comprises a detectable label. Thus, in one aspect of a method wherein detection of the target polynucleotide is desired, it is the displacement and/or release of the sicPN that generates the detectable change through the action of the detectable label. In another method wherein detection of the target polynucleotide is desired, it is the target polynucleotide that generates the detectable change through its own detectable label. In methods wherein inhibition of the target polynucleotide expression is desired, it is the association of the polynucleotide that is part of the nanoconjugate with the target polynucleotide that generates the inhibition of target polynucleotide expression through an antisense mechanism.

The compositions of the disclosure comprise a plurality of sicPNs, able to associate with a plurality of polynucleotides, that may be used on one or more surfaces to specifically associate with a plurality of target polynucleotides. Thus, the steps or combination of steps of the methods described below apply to one or a plurality of polynucleotides that are part of one or more nanoconjugates, sicPNs and target polynucleotides.

In various aspects, the methods include use of a polynucleotide which is 100% complementary to the target polynucleotide, i.e., a perfect match, while in other aspects, the polynucleotide is at least (meaning greater than or equal to) about 95% complementary to the polynucleotide over the length of the polynucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the polynucleotide to the extent that the polynucleotide is able to achieve the desired of inhibition of a target gene product. It will be understood by those of skill in the art that the degree of hybridization is less significant than a resulting detection of the target polynucleotide, or a degree of inhibition of gene product expression.

Methods of Detecting a Target Polynucleotide

The disclosure provides methods of detecting a target biomolecule comprising contacting the target biomolecule with a composition as described herein. The contacting results, in various aspects, in regulation of gene expression as provided by the disclosure. In another aspect, the contacting results in a detectable change, wherein the detectable change indicates the detection of the target biomolecule. Detection of the detectable label is performed by any of the methods described herein, and the detectable label can be on a biomolecule that is part of a nanoconjugate, or can be on the target biomolecule.

In some aspects, and as described above, it is the displacement and/or release of the sicPN that generates the detectable change. The detectable change is assessed through the use of a detectable label, and in one aspect, the sicPN is labeled with the detectable label. Further according the methods, the detectable label is quenched when in proximity with a surface used to template the nanoconjugate. While it is understood in the art that the term "quench" or "quenching" is often associated with fluorescent markers, it is contemplated herein that the signal of any marker that is quenched when it is relatively undetectable. Thus, it is to be understood that methods exemplified throughout this description that employ fluorescent markers are provided only as single embodiments of the methods contemplated, and that any marker which can be quenched can be substituted for the exemplary fluorescent marker.

The sicPN is thus associated with the nanoconjugate in such a way that the detectable label is in proximity to the surface to quench its detection. When the polynucleotide that is part of the nanoconjugate comes in contact and associates with the target polynucleotide, it causes displacement and/or release of the sicPN. The release of the sicPN thus increases the distance between the detectable label present on the sicPN and the surface to which the polynucleotide was templated. This increase in distance allows detection of the previously quenched detectable label, and indicates the presence of the target polynucleotide.

Thus, in one embodiment a method is provided in which a plurality of polynucleotides are used to produce a nanoconjugate by a method described herein. The polynucleotides are designed to be able to hybridize to one or more target polynucleotides under stringent conditions. Hybridization can be performed under different stringency conditions known in the art and as discussed herein. Following production of a nanoconjugate with the plurality of polynucleotides, a plurality of sicPNs optionally comprising a detectable label is added and allowed to hybridize with the polynucleotides that are part of the nanoconjugate. In some aspects, the plurality of polynucleotides and the sicPNs are first hybridized to each other, and then duplexes used to produce the nanoconjugate. Regardless of the order in which the plurality of polynucleotide is hybridized to the plurality of sicPNs and the duplex is used to produce the nanoconjugate, the next step is to contact the nanoconjugate with a target polynucleotide. The target polynucleotide can, in various aspects, be in a solution, or it can be inside a cell. It will be understood that in some aspects, the solution is being tested for the presence or absence of the target polynucleotide while in other aspects, the solution is being tested for the relative amount of the target polynucleotide.

After contacting the duplex with the target polynucleotide, the target polynucleotide will displace and/or release the sicPN as a result of its hybridization with the polynucleotide that is part of the nanoconjugate. The displacement and release of the sicPN allows an increase in distance between the surface and the sicPN, thus resulting in the label on the sicPN being rendered detectable. The amount of label that is detected as a result of displacement and release of the sicPN is related to the amount of the target polynucleotide present in the solution. In general, an increase in the amount of detectable label correlates with an increase in the number of target polynucleotides in the solution.

In some embodiments it is desirable to detect more than one target polynucleotide in a solution. In these embodiments, more than one sicPN is used, and each sicPN comprises a unique detectable label. Accordingly, each target polynucleotide, as well as its relative amount, is individually detectable based on the detection of each unique detectable label.

In some embodiments, the compositions of the disclosure are useful in nano-flare technology. The nano-flare has been previously described in the context of polynucleotide-functionalized nanoparticles that can take advantage of a sicPN architecture for fluorescent detection of biomolecule levels inside a living cell [described in WO 2008/098248, incorporated by reference herein in its entirety]. In this system the sicPN acts as the "flare" and is detectably labeled and displaced or released from the surface by an incoming target polynucleotide. It is thus contemplated that the nano-flare technology is useful in the context of the nanoconjugates described herein.

In further aspects, the nanoconjugate is used to detect the presence or amount of cysteine in a sample, comprising providing a first mixture comprising a complex comprising Hg2+ and a population of nanoconjugates, wherein the population comprises nanoconjugates comprising one of a pair of single stranded polynucleotides and nanoconjugates comprising the other single stranded polynucleotide of the pair, wherein the pair forms a double stranded duplex under appropriate conditions having at least one nucleotide mismatch, contacting the first mixture with a sample suspected of having cysteine to form a second mixture, and detecting the melting point of the double stranded duplex in the second mixture, wherein the melting point is indicative of the presence or amount of cysteine in the sample. In some aspects, the nucleotide mismatch is an internal nucleotide mismatch. In a further aspect, the mismatch is a T-T mismatch. In still a further aspect, the sample comprising cysteine has a melting point at least about 5° C. lower than a sample without cysteine.

Methods of Inhibiting Gene Expression

Additional methods provided by the disclosure include methods of inhibiting expression of a gene product expressed from a target polynucleotide comprising contacting the target polynucleotide with a composition as described herein, wherein the contacting is sufficient to inhibit expression of the gene product. Inhibition of the gene product results from the hybridization of a target polynucleotide with a composition of the disclosure.

It is understood in the art that the sequence of a polynucleotide that is part of a nanoconjugate need not be 100% complementary to that of its target polynucleotide in order to specifically hybridize to the target polynucleotide. Moreover, a polynucleotide that is part of a nanoconojugate may hybridize to a target polynucleotide over one or more segments such that intervening or adjacent segments are not involved in the hybridization event (for example and without limitation, a loop structure or hairpin structure). The percent complementarity is determined over the length of the polynucleotide that is part of the nanoconjugate. For example, given a nanoconjugate comprising a polynucleotide in which 18 of 20 nucleotides of the polynucleotide are complementary to a 20 nucleotide region in a target polynucleotide of 100 nucleotides total length, the polynucleotide that is part of the nanoconjugate would be 90 percent complementary. In this example, the remaining noncomplementary nucleotides may be clustered or interspersed with complementary nucleotides and need not be contiguous to each other or to complementary nucleotides. Percent complementarity of a polynucleotide that is part of a nanoconjugate with a region of a target polynucleotide can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a nanoconjugate comprising a biomolecule and/or non-biomolecule. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in vitro in a cell culture assay, generally as a predictable measure of a degree of inhibition that can be expected in vivo resulting from use of a composition as described herein. It is contemplated by the disclosure that the inhibition of a target polynucleotide is used to assess the effects of the inhibition on a given cell. By way of non-limiting examples, one can study the effect of the inhibition of a gene product wherein the gene product is part of a signal transduction pathway. Alternatively, one can study the inhibition of a gene product wherein the gene product is hypothesized to be involved in an apoptotic pathway.

It will be understood that any of the methods described herein can be used in combination to achieve a desired result. For example and without limitation, methods described herein can be combined to allow one to both detect a target polynucleotide as well as regulate its expression. In some embodiments, this combination can be used to quantitate the inhibition of target polynucleotide expression over time either in vitro or in vivo. The quantitation over time is achieved, in one aspect, by removing cells from a culture at specified time points and assessing the relative level of expression of a target polynucleotide at each time point. A decrease in the amount of target polynucleotide as assessed, in one aspect, through visualization of a detectable label, over time indicates the rate of inhibition of the target polynucleotide.

Thus, determining the effectiveness of a given polynucleotide to hybridize to and inhibit the expression of a target polynucleotide, as well as determining the effect of inhibition of a given polynucleotide on a cell, are aspects that are contemplated.

Imaging Methods

Magnetic Resonance Imaging (MRI)

In certain embodiments, the MRI contrast agent conjugated to a polynucleotide is iron or paramagnetic radiotracers and/or complexes, including but not limited to gadolinium, xenon, iron oxide, and copper.

Fluorescence

Methods are provided wherein presence of a composition of the disclosure is detected by an observable change. In one aspect, presence of the composition gives rise to a color change which is observed with a device capable of detecting a specific marker as disclosed herein. For example and without limitation, a fluorescence microscope can detect the presence of a fluorophore that is conjugated to a polynucleotide, which is part of a nanoconjugate.

Complex Visualization through Catalytic Metal Deposition

Methods described herein include depositing a metal on a complex formed between a nanoconjugate as defined herein and a target molecule to enhance detection of the complex. Metal is deposited on the nanoparticle/target molecule when the nanoparticle/target molecule complex is contacted with a metal enhancing solution under conditions that cause a layer of the metal to deposit on the complex. Thus, the present disclosure also provides a composition comprising a nanoconjugate, the nanoconjugate having a single catalytic metal deposit, the composition having an average diameter of at least about 250 nanometers. In some embodiments, the average diameter is from about 250 nanometers to about 5000 nanometers. In some aspects, more than one catalytic metal deposit is contemplated.

A metal enhancing solution, as used herein, is a solution that is contacted with a nanoconjugate-target molecule complex to deposit a metal on the complex. In various aspects and depending on the type of metal being deposited, the metal enhancing solution comprises, for example and without limitation, $HAuCl_4$, silver nitrate, $NH_2OH$ and hydroquinone.

In some embodiments, the target molecule is immobilized on a support when it is contacted with the nanoconjugate. A support, as used herein, includes but is not limited to a column, a membrane, or a glass or plastic surface. A glass surface support includes but is not limited to a bead or a slide. Plastic surfaces contemplated by the present disclosure include but are not limited to slides, and microtiter plates. Microarrays are additional supports contemplated by the present disclosure, and are typically either glass, silicon-based or a polymer. Microarrays are known to those of ordinary skill in the art and comprise target molecules arranged on the support in addressable locations. Microarrays can be purchased from, for example and without limitation, Affymetrix, Inc.

In some embodiments, the target molecule is in a solution. In this type of assay, a nanoconjugate is contacted with the target molecule in a solution to form a nanoparticle/target molecule complex that is then detected following deposition of a metal on the complex. Methods of this type are useful whether the target molecule is in a solution or in a body fluid. For example and without limitation, a solution as used herein means a buffered solution, water, or an organic solution. Body fluids include without limitation blood (serum or plasma), lymphatic fluid, cerebrospinal fluid, semen, urine, synovial fluid, tears, mucous, and saliva and can be obtained by methods routine to those skilled in the art.

The disclosure also contemplates the use of the compositions and methods described herein for detecting a metal ion (for example and without limitation, mercuric ion ($Hg^{2+}$)). In these aspects, the method takes advantage of the cooperative binding and catalytic properties of the nanoconjugates comprising a DNA polynucleotide and the selective binding of a thyminethymine mismatch for $Hg^{2+}$ [Lee et al., Anal. Chem. 80: 6805-6808 (2008)].

Methods described herein are also contemplated for use in combination with the biobarcode assay. The biobarcode assay is generally described in U.S. Pat. Nos. 6,974,669 and 7,323,309, each of which is incorporated herein by reference in its entirety.

Methods of the disclosure include those wherein silver or gold or combinations thereof are deposited on a nanoconjugate in a complex with a target molecule.

In one embodiment, methods of silver deposition on a nanoconjugate as described herein yield a limit of detection of a target molecule of about 3 pM after a single silver deposition. In another aspect, a second silver deposition improves the limit of detection to about 30 fM. Thus, the number of depositions of silver relates to the limit of detection of a target molecule. Accordingly, one of ordinary skill in the art will understand that the methods of the present disclosure may be tailored to correlate with a given concentration of target molecule. For example and without limitation, for a target molecule concentration of 30 fM, two silver depositions can be used. Concentrations of target molecule suitable for detection by silver deposition are about 3 pM, about 2 pM, about 1 pM, about 0.5 pM, about 400 fM, about 300 fM, about 200 fM, about 100 fM or less.

In methods provided, a nanoconjugate is contacted with a sample comprising a first molecule under conditions that allow complex formation between the nanoconjugate and the first molecule.

Methods are also provided wherein a second molecule is contacted with the first molecule under conditions that allow complex formation prior to the contacting of the nanoconjugate with the first molecule.

Method are also contemplated wherein a target molecule is attached to a second nanoconjugate that associates with the first nanoconjugate. In some aspects, the second nanoconjugate is immobilized on a solid support. In other aspects, the second nanoconjugate is in a solution.

Methods provided also generally contemplate contacting a composition comprising a nanoconjugate with more than one target molecules. Accordingly, in some aspects it is contemplated that a nanoconjugate comprising more than one polypeptide and/or polynucleotide, is able to simultaneously recognize and associate with more than one target molecule.

In further embodiments, a target polynucleotide is identified using a "sandwich" protocol for high-throughput detection and identification. For example and without limitation, a polynucleotide that recognizes and selectively associates with the target polynucleotide is immobilized on a solid support. The sample comprising the target polynucleotide is contacted with the solid support comprising the polynucleotide, thus allowing an association to occur. Following removal of non-specific interactions, a composition comprising a nanoconjugate as described herein is added. In these aspects, the nanoconjugate comprises a molecule that selectively associates with the target polynucleotide, thus generating the "sandwich" of polynucleotide-target polynucleotide-nanoconjugate. This complex is then exposed to a metal deposition process as described herein, resulting in highly sensitive detection. Quantification of the interaction allows for determinations relating but not limited to disease progression, therapeutic effectiveness, disease identification, and disease susceptibility.

Additional description of catalytic deposition of metal on a complex formed between a nanoconjugate as defined herein and a target molecule to enhance detection of the complex is found in U.S. application Ser. No. 12/770,488, which is incorporated by reference herein in its entirety.

Detecting Modulation of Transcription of a Target Polynucleotide

Methods provided by the disclosure include a method of detecting modulation of transcription of a target polynucleotide comprising administering a nanoconjugate and a transcriptional regulator and measuring a detectable change, wherein the transcriptional regulator increases or decreases transcription of the target polynucleotide in a target cell relative to a transcription level in the absence of the transcriptional regulator.

The disclosure also contemplates methods to identify the target polynucleotide. In some aspects of these methods, a library of polynucleotides is screened for its ability to detect the increase or decrease in transcription of the target polynucleotide. The library, in various aspects, is a polynucleotide library. In some aspects of these methods, a double stranded polynucleotide comprising a known sequence is used to produce a nanoconjugate, creating a first nanoconjugate. In some aspects, one strand of the double stranded polynucleotide further comprises a detectable marker that is quenched while the two strands of the polynucleotide remain hybridized to each other. The nanoconjugate is then contacted with a target cell concurrently with a transcriptional regulator. If the polynucleotide of known sequence that is used to produce the nanoconjugate hybridizes with the target polynucleotide, it results in a detectable change. The detectable change, in some aspects, is fluorescence. Observation of a detectable change that is significantly different from the detectable change observed by contacting the target cell with a second nanoconjugate in which the polynucleotide comprises a different sequence than the first nanoconjugate is indicative of identifying the target polynucleotide. Thus, in further aspects, each nanoconjugate comprises a polynucleotide of known sequence, and in still further aspects, an increase or decrease in the detectable change when the transcriptional regulator is administered relative to the detectable change measured when a different nanoparticle comprising a polynucleotide within the library is administered is indicative of identifying the target polynucleotide. Accordingly, in some aspects the methods provide for the identification of a mRNA that is regulated by a given transcriptional regulator. In various aspects, the mRNA is increased, and in some aspects the mRNA is decreased.

Local delivery of a composition comprising a nanoconjugate to a human is contemplated in some aspects of the disclosure. Local delivery involves the use of an embolic agent in combination with interventional radiology and a composition of the disclosure.

Use of a Nanoconjugate as a Probe

The nanoconjugates are, in one aspect, used as probes in diagnostic assays for detecting nucleic acids.

Some embodiments of the method of detecting a target nucleic acid utilize a substrate. Any substrate can be used which allows observation of the detectable change. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes), and conducting solid surfaces (e.g., indium-tin-oxide (ITO)). The substrate can be any shape or thickness, but generally will be flat and thin. Preferred are transparent substrates such as glass (e.g., glass slides) or plastics (e.g., wells of microtiter plates). Methods of attaching polynucleotides to a substrate and uses thereof with respect to nanoconjugates are disclosed in U.S. Patent Application 20020172953, incorporated herein by reference in its entirety.

By employing a substrate, the detectable change can be amplified and the sensitivity of the assay increased. In one aspect, the method comprises the steps of contacting a target polynucleotide with a substrate having a polynucleotide attached thereto, the polynucleotide (i) having a sequence complementary to a first portion of the sequence of the target nucleic acid, the contacting step performed under conditions effective to allow hybridization of the polynucleotide on the substrate with the target nucleic acid, and (ii) contacting the target nucleic acid bound to the substrate with a first type of nanoconjugate having a polynucleotide attached thereto, the polynucleotide having a sequence complementary to a second portion of the sequence of the target nucleic acid, the contacting step performed under conditions effective to allow hybridization of the polynucleotide that is part of the nanoconjugate with the target nucleic acid. Next, the first type of nanoconjugate bound to the substrate is contacted with a second type of nanoconjugate comprising a polynucleotide, the polynucleotide on the second type of nanoconjugate having a sequence complementary to at least a portion of the sequence of the polynucleotide used to produce the first type of nanoconjugate, the contacting step taking place under conditions effective to allow hybridization of the polynucleotides on the first and second types of nanoconjugates. Finally, a detectable change produced by these hybridizations is observed.

The detectable change that occurs upon hybridization of the polynucleotides on the nanoconjugates to the nucleic acid may be a color change, the formation of aggregates of the nanoconjugates, or the precipitation of the aggregated nanoconjugates. The color changes can be observed with the naked eye or spectroscopically. The formation of aggregates of the nanoconjugates can be observed by electron microscopy or by nephelometry. The precipitation of the aggregated nanoconjugates can be observed with the naked eye or microscopically. Preferred are changes observable with the naked eye. Particularly preferred is a color change observable with the naked eye.

The methods of detecting target nucleic acid hybridization based on observing a color change with the naked eye are cheap, fast, simple, robust (the reagents are stable), do not require specialized or expensive equipment, and little or no instrumentation is required. These advantages make them particularly suitable for use in, e.g., research and analytical laboratories in DNA sequencing, in the field to detect the presence of specific pathogens, in the doctor's office for quick identification of an infection to assist in prescribing a drug for treatment, and in homes and health centers for inexpensive first-line screening.

A nanoconjugate comprising a polynucleotide can be used in an assay to target a target molecule of interest. Thus, the nanoconjugate comprising a polynucleotide can be used in an assay such as a bio barcode assay. See, e.g., U.S. Pat. Nos. 6,361,944; 6,417,340; 6,495,324; 6,506,564; 6,582,921; 6,602,669; 6,610,491; 6,678,548; 6,677,122; 6682,895; 6,709,825; 6,720,147; 6,720,411; 6,750,016; 6,759,199; 6,767,702; 6,773,884; 6,777,186; 6,812,334; 6,818,753; 6,828,432; 6,827,979; 6,861,221; and 6,878,814, the disclosures of which are incorporated herein by reference.

Dosing And Pharmaceutical Compositions

It will be appreciated that any of the compositions described herein may be administered to a mammal in a therapeutically effective amount to achieve a desired therapeutic effect.

The term "therapeutically effective amount", as used herein, refers to an amount of a composition sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by an assay described herein. The precise effective amount for a subject will depend upon the subject's body weight, size, and health; the nature and extent of the condition; and the antibiotic composition or combination of compositions selected for administration. Therapeutically effective amounts for a given situation can be determined by routine experimentation that is within the skill and judgment of the clinician.

The compositions described herein may be formulated in pharmaceutical compositions with a pharmaceutically acceptable excipient, carrier, or diluent. The compound or composition can be administered by any route that permits treatment of, for example and without limitation, a disease, disorder or infection as described herein. A preferred route of administration is oral administration. Additionally, the compound or composition comprising the antibiotic composition may be delivered to a patient using any standard route of administration, including parenterally, such as intravenously, intraperitoneally, intrapulmonary, subcutaneously or intramuscularly, intrathecally, transdermally (as described herein), rectally, orally, nasally or by inhalation.

Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or the compound of the embodiments can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition. Administration of combinations of therapeutic agents (i.e., combination therapy) is also contemplated, provided at least one of the therapeutic agents is in association with a nanoconjugate as described herein.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions comprises in various aspects a therapeutically or prophylactically effective amount of at least one composition as described herein, together with one or more pharmaceutically acceptable excipients. As described herein, the pharmaceutical compositions may optionally comprise a combination of the compounds described herein.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using suitable dispersing or wetting agents and suspending agents. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

Transdermal Delivery

In some aspects of the disclosure, a method of dermal delivery of a nanoconjugate is provided comprising the step of administering a composition comprising the nanoconjugate and a dermal vehicle to the skin of a patient in need thereof.

In one aspect, the delivery of the nanoconjugate is transdermal. In another aspect, the delivery of the nanoconjugate is topical. In another aspect, the delivery of the nanoconjugate is to the epidermis and dermis after topical application. In some embodiments, the dermal vehicle comprises an ointment. In some aspects, the ointment is Aquaphor.

In further embodiments of the methods, the administration of the composition ameliorates a skin disorder. In various embodiments, the skin disorder is selected from the group consisting of cancer, a genetic disorder, aging, inflammation, infection, and cosmetic disfigurement.

See PCT/US2010/27363, incorporated by reference herein in its entirety, for further description of dermal delivery of nanoparticle compositions and methods of their use.

Vehicles

In some embodiments, compositions and methods of the present disclosure comprise vehicles. As used herein, a "vehicle" is a base compound with which an nanoconjugate composition is associated.

Vehicles useful in the compositions and methods of the present disclosure are known to those of ordinary skill in the art and include without limitation an ointment, cream, lotion, gel, foam, buffer solution (for example and without limitation, Ringer's solution and isotonic sodium chloride solution) or water. In some embodiments, vehicles comprise one or more additional substances including but not limited to salicylic acid, alpha-hydroxy acids, or urea that enhance the penetration through the stratum corneum.

In various aspects, vehicles contemplated for use in the compositions and methods of the present disclosure include, but are not limited to, Aquaphor® healing ointment, A+D, polyethylene glycol (PEG), glycerol, mineral oil, Vaseline Intensive Care cream (comprising mineral oil and glycerin), petroleum jelly, DML (comprising petrolatum, glycerin and PEG 20), DML (comprising petrolatum, glycerin and PEG 100), Eucerin moisturizing cream, Cetaphil (comprising petrolatum, glycerol and PEG 30), Cetaphil, CeraVe (comprising petrolatum and glycerin), CeraVe (comprising glycerin, EDTA and cholesterol), Jergens (comprising petrolatum, glycerin and mineral oil), and Nivea (comprising petrolatum, glycerin and mineral oil). One of ordinary skill in the art will understand from the above list that additional vehicles are useful in the compositions and methods of the present disclosure.

An ointment, as used herein, is a formulation of water in oil. A cream as used herein is a formulation of oil in water. In general, a lotion has more water than a cream or an ointment; a gel comprises alcohol, and a foam is a substance that is formed by trapping gas bubbles in a liquid. These terms are understood by those of ordinary skill in the art.

Embolic Agents

Administration of an embolic agent in combination with a composition of the disclosure is also contemplated. Embolic agents serve to increase localized drug concentration in target sites through selective occlusion of blood vessels by purposely introducing emboli, while decreasing drug washout by decreasing arterial inflow. Thus, a composition comprising a nanoparticle comprising a polynucleotide, wherein the polynucleotide is conjugated to a contrast agent through a conjugation site would remain at a target site for a longer period of time in combination with an embolic agent relative to the period of time the composition would remain at the target site without the embolic agent. Accordingly, in some embodiments, the present disclosure contemplates the use of a composition as described herein in combination with an embolic agent.

In various aspects of the compositions and methods of the disclosure, the embolic agent to be used is selected from the group consisting of a lipid emulsion (for example and without limitation, ethiodized oil or lipiodol), gelatin sponge, tris acetyl gelatin microspheres, embolization coils, ethanol, small molecule drugs, biodegradable microspheres, non-biodegradable microspheres or polymers, and self-assembling embolic material.

The compositions disclosed herein are administered by any route that permits imaging of the tissue or cell that is desired, and/or treatment of the disease or condition. In one aspect the route of administration is intraarterial administration. Additionally, the composition comprising a nanoconjugate is delivered to a patient using any standard route of administration, including but not limited to orally, parenterally, such as intravenously, intraperitoneally, intrapulmonary, intracardiac, intraosseous infusion ("IO"), subcutaneously or intramuscularly, intrathecally, transdermally, intradermally, rectally, orally, nasally or by inhalation or transmucosal delivery. Direct injection of a composition provided herein is also contemplated and, in some aspects, is delivered via a hypodermic needle. Slow release formulations may also be prepared from the compositions described herein in order to achieve a controlled release of one or more components of a composition as described herein in contact with the body fluids and to provide a substantially constant and effective level of one or more components of a composition in the blood plasma.

Target Site Identification and Composition Delivery

Provided herein are methods of delivering a contrast agent to a cell comprising contacting the cell with a composition of the disclosure under conditions sufficient to deliver the contrast agent to the cell. Following delivery of the composition, in some aspects the method further comprises the step of detecting the contrast agent. Detecting the contrast agent is performed by any of the methods known in the art, including those described herein.

In a specific embodiment, the contrast agent is detected using an imaging procedure, and in various aspects, the imaging procedure is selected from the group consisting of MRI, CT, and fluorescence.

Methods provided also include those wherein a composition of the disclosure is locally delivered to a target site. Once the target site has been identified, a composition of the disclosure is delivered, in one aspect, intraarterially. In another aspect, a composition of the disclosure is delivered intravenously. Target cells for delivery of a composition of the disclosure are, in various aspects, selected from the group consisting of a cancer cell, a stem cell, a T-cell, and a β-islet cell.

In various aspects, the target site is a site of pathogenesis. In some aspects, the site of pathogenesis is cancer. In various aspects, the cancer is selected from the group consisting of liver, pancreatic, stomach, colorectal, prostate, testicular, renal cell, breast, bladder, ureteral, brain, lung, connective tissue, hematological, cardiovascular, lymphatic, skin, bone, eye, nasopharyngeal, laryngeal, esophagus, oral membrane, tongue, thyroid, parotid, mediastinum, ovary, uterus, adnexal, small bowel, appendix, carcinoid, gall bladder, pituitary, cancer arising from metastatic spread, and cancer arising from endodermal, mesodermal or ectodermally-derived tissues.

In some embodiments, the site of pathogenesis is a solid organ disease. In various aspects, the solid organ is selected from the group consisting of heart, liver, pancreas, prostate, brain, eye, thyroid, pituitary, parotid, skin, spleen, stomach, esophagus, gall bladder, small bowel, bile duct, appendix, colon, rectum, breast, bladder, kidney, ureter, lung, and a endodermally-, ectodermally- or mesodermally-derived tissues.

Activation of a Chemotherapeutic Agent

According to the disclosure, it is contemplated that a chemotherapeutic agent that is attached to a nanoconjugate as described herein is activated upon entry into a cell. In some aspects, the activated chemotherapeutic agent confers an increase in cytotoxicity relative to a chemotherapeutic agent that is not attached to a polynucleotide, wherein the polynucleotide is part of a nanoconjugate, and wherein the increase in cytotoxicity is measured using an in vitro cell culture assay. The in vitro cell culture assay is, for example and without limitation, a (3-(4,5-dimethylthiazol-2-yl)-2,5-diphenyltetrazolium bromide) (MTT) assay. Accordingly, the increase in cytotoxicity described above is coupled with the reduced toxicity of the chemotherapeutic agent which is attached to a polynucleotide that is part of a nanoconjugate prior to its entry into a cell.

Target Molecules

It is contemplated by the disclosure that any of the compositions described herein can be used to detect a target molecule. In various aspects, the target molecule is a polynucleotide, and the polynucleotide is either eukaryotic, prokaryotic, or viral.

In some aspects, the target molecule is a polynucleotide. If a polynucleotide is present in small amounts, it may be amplified by methods known in the art. See, e.g., Sambrook et al., Molecular Cloning: A Laboratory Manual (2nd ed. 1989)

and B. D. Hames and S. J. Higgins, Eds., Gene Probes 1 (IRL Press, New York, 1995). Generally, but without limitation, polymerase chain reaction (PCR) amplification can be performed to increase the concentration of a target nucleic acid to a degree that it can be more easily detected.

In various embodiments, methods provided include those wherein the target polynucleotide is a mRNA encoding a gene product and translation of the gene product is inhibited, or the target polynucleotide is DNA in a gene encoding a gene product and transcription of the gene product is inhibited. In methods wherein the target polynucleotide is DNA, the polynucleotide is in certain aspects DNA which encodes the gene product being inhibited. In other methods, the DNA is complementary to a coding region for the gene product. In still other aspects, the DNA encodes a regulatory element necessary for expression of the gene product. "Regulatory elements" include, but are not limited to enhancers, promoters, silencers, polyadenylation signals, regulatory protein binding elements, regulatory introns, ribosome entry sites, and the like. In still another aspect, the target polynucleotide is a sequence which is required for endogenous replication. In further embodiments, the target molecule is a microRNA (miRNA).

Anti-Prokaryotic Target Polynucleotides

For prokaryotic target polynucleotides, in various aspects, the polynucleotide is genomic DNA or RNA transcribed from genomic DNA. For eukaryotic target polynucleotides, the polynucleotide is an animal polynucleotide, a plant polynucleotide, a fungal polynucleotide, including yeast polynucleotides. As above, the target polynucleotide is either a genomic DNA or RNA transcribed from a genomic DNA sequence. In certain aspects, the target polynucleotide is a mitochondrial polynucleotide. For viral target polynucleotides, the polynucleotide is viral genomic RNA, viral genomic DNA, or RNA transcribed from viral genomic DNA.

In one embodiment, the polynucleotides of the invention are designed to hybridize to a target prokaryotic sequence under physiological conditions.

It will be understood that one of skill in the art may readily determine appropriate targets for nanoconjugates comprising a polynucleotide, and design and synthesize polynucleotides using techniques known in the art. Targets can be identified by obtaining, e.g., the sequence of a target nucleic acid of interest (e.g. from GenBank) and aligning it with other nucleic acid sequences using, for example, the MacVector 6.0 program, a ClustalW algorithm, the BLOSUM 30 matrix, and default parameters, which include an open gap penalty of 10 and an extended gap penalty of 5.0 for nucleic acid alignments.

Any essential prokaryotic gene is contemplated as a target gene using the methods of the present disclosure. As described above, an essential prokaryotic gene for any prokaryotic species can be determined using a variety of methods including those described by Gerdes for *E. coli* [Gerdes et al., *J Bacteriol.* 185(19): 5673-84, 2003]. Many essential genes are conserved across the bacterial kingdom thereby providing additional guidance in target selection. Target gene sequences can be identified using readily available bioinformatics resources such as those maintained by the National Center for Biotechnology Information (NCBI).

Nanoconjugates comprising a polynucleotide showing optimal activity are then tested in animal models, or veterinary animals, prior to use for treating human infection.

Target Sequences for Cell-Division and Cell-Cycle Target Proteins

The polynucleotides of the present disclosure are designed to hybridize to a sequence of a prokaryotic nucleic acid that encodes an essential prokaryotic gene. Exemplary genes include but are not limited to those required for cell division, cell cycle proteins, or genes required for lipid biosynthesis or nucleic acid replication.

For each of these three proteins, Table 1 of U.S. Patent Application Number 20080194463, incorporated by reference herein in its entirety, provides exemplary bacterial sequences which contain a target sequence for each of a number of important pathogenic bacteria. The gene sequences are derived from the GenBank Reference full genome sequence for each bacterial strain.

Target Sequences for Prokaryotic 16S Ribosomal RNA

In one embodiment, the polynucleotides of the invention are designed to hybridize to a sequence encoding a bacterial 16S rRNA nucleic acid sequence under physiological conditions, with a $T_m$ substantially greater than 37° C., e.g., at least 45° C. and preferably 60° C.-80° C.

Exemplary bacteria and associated GenBank Accession Nos. for 16S rRNA sequences are provided in Table 1 of U.S. Pat. No. 6,677,153, incorporated by reference herein in its entirety.

Additional Target Molecules

The target molecule may be in cells, tissue samples, or biological fluids, as also known in the art.

In various embodiments the disclosure contemplates that more than one target polynucleotide is detected in the target cell.

In further embodiments the target molecule is an ion. The present disclosure contemplates that in one aspect the ion is nitrite (NO2-). In some aspects, the ion is a metal ion that is selected from the group consisting of mercury (Hg2+), Cu2+ and UO2+.

Kits

Also provided are kits comprising a composition of the disclosure. In one embodiment, the kit comprises at least one container, the container holding at least one type of nanoconjugate as described herein comprising one or more polynucleotides as described herein. The polynucleotides that are part of the first type of nanoconjugate have one or more sequences complementary (or sufficiently complementary as disclosed herein) to one or more sequences of a first portion of a target polynucleotide. The container optionally includes one or more additional type of nanoconjugates comprising a polynucleotide with a sequence complementary to one or more sequence of a second portion of the target polynucleotide.

In another embodiment, the kit comprises at least two containers. The first container holds one or more nanoconjugates as disclosed herein comprising one or more biomolecules and/or non-biomolecules as described herein which can associate with one or more portions of a target biomolecule and/or non-biomolecule. The second container holds one or more nanoconjugates comprising one or more biomolecules and/or non-biomolecules can associate with one or more sequences of the same or a different portion of the target biomolecule and/or non-biomolecule.

In another embodiment, the kits have biomolecules and/or non-biomolecules and nanoparticles in separate containers, and the nanoconjugates are produced prior to use for a method described herein. In one aspect, the biomolecules and/or non-biomolecules and/or the nanoparticles are functionalized so that the nanoconjugates can be produced. Alternatively, the biomolecules and/or non-biomolecules and/or nanoparticles are provided in the kit without functional groups, in which case they must be functionalized prior to performing the assay. In additional aspects, a chemical is provided that facilitates the crosslinking of the biomolecules and/or non-biomolecules.

In various aspects of the kits provided, biomolecules and/or non-biomolecules include a label or the kit includes a label which can be attached to the biomolecules and/or non-biomolecules. Alternatively, the kits include labeled nanoparticles or labels which can be attached to the nanoparticles. In each embodiment, the kit optionally includes instructions, each container contains a label, the kit itself includes a label, the kit optionally includes one or more non-specific biomolecules (for use as controls).

EXAMPLES

Example 1

Materials

All materials were purchased from Sigma-Aldrich and used without further purification, unless otherwise indicated. TEM characterization was conducted on a Hitachi H8100 electron microscope. NMR experiments were performed using a Bruker Avance III 500 MHz coupled with a DCH CryoProbe. DLS data were acquired from a MALVERN Zetasizer, Nano-ZS. IR results were obtained from a Bruker TENSOR 37, and analyzed using the OPUS software. MALDI-TOF measurements were carried out on a Bruker Autoflex III SmartBeam mass spectrometer.

Synthesis of poly(N-(2-(3-(prop-2-ynyloxy)propanamido)ethyl)acrylamide) 1

Figure 12A:
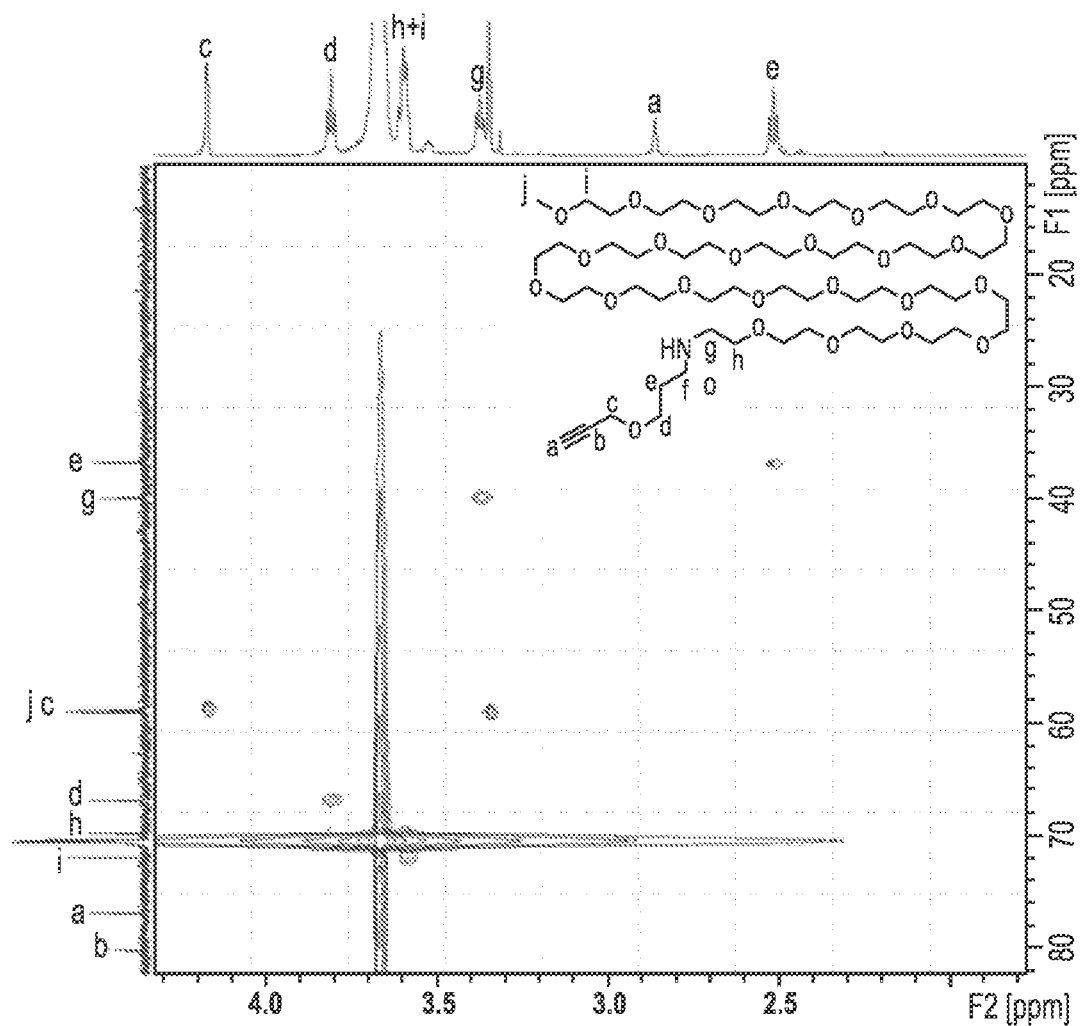
FIG. 12 shows A) HSQC for 5. B) HSQC for 5 after reaction. C) MALDI-TOF MS for 5 before and after reaction.
Figure 12B:
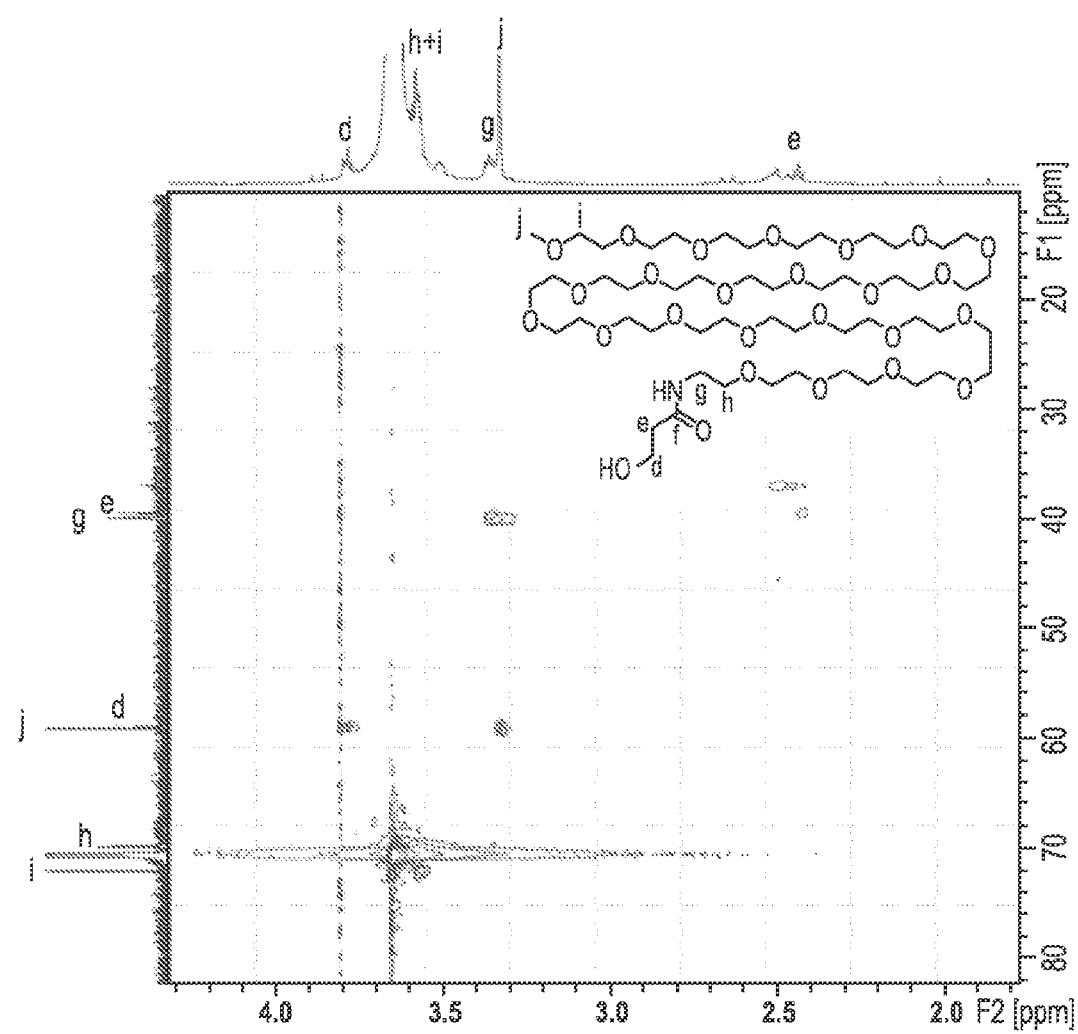
Figure 12C:
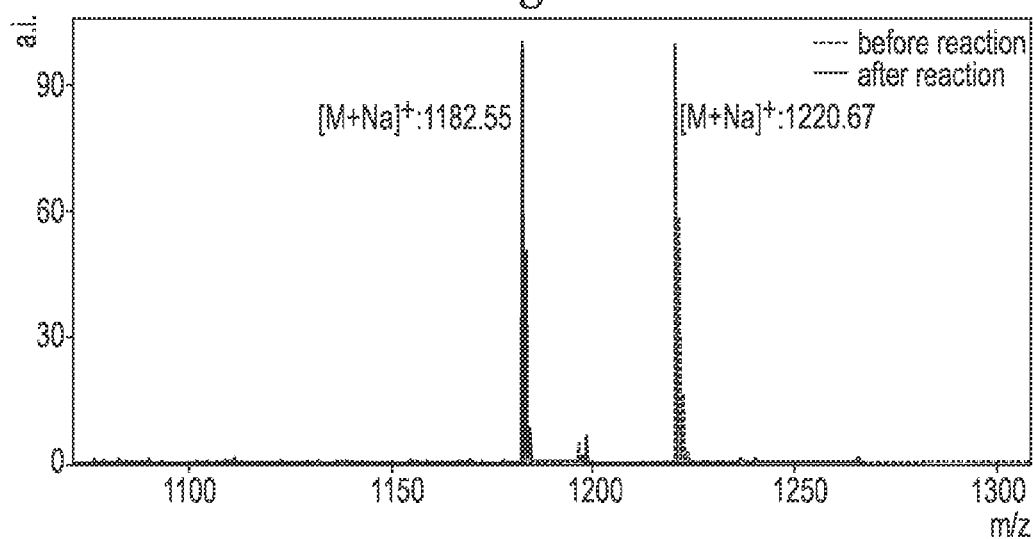

Polyacrylamidoethylamine120 (PAEAl20) was prepared following literature reported methods [Zhang et al., Biomaterials 31: 1805 (2010); Zhang et al., Biomaterials 30: 968 (2009)]. PAEAl20 (67.5 mg, 4.9 μmol) was dissolved in anhydrous DMSO (2 mL), and stirred for 3 hours, before 1 mL DMSO solution containing propargyl-dPEG1-NHS ester (150 mg, 660 μmol, Quanta Biodesign) and diisopropylethylamine (DIPEA, 204 μL 1.17 mmol) was added. The reaction mixture was allowed to stir overnight, diluted by the addition of DMSO (10 mL), transferred to pre-soaked dialysis tubing (MWCO=3.5 kDa), and dialyzed against nanopure water (>18.0 MΩ.cm) for 3 days. The solution was then lyophilized and re-suspended in water (15 mL). A small amount of cloudiness was observed, which was removed by filtering through a 0.2 μm syringe filter. No residual amine group was detected by a ninhydrin test. IR and 1H-13C HSQC NMR spectra of 1 are shown in FIG. 12.

Synthesis of methyl-terminated poly(ethylene glycol)-propargyl ether conjugate 5

Monodisperse mPEG24-amine (39.0 mg, 34.6 μmol, Quanta Biodesign) was dissolved in 1.0 mL pH=8.0 phosphate buffer, to which propargyl-dPEG1-NHS ester (12.1 mg, 53.7 μmol) was added. The mixture was allowed to be shaken for 12 hours at 4° C. The desired conjugate was isolated from the reaction mixture by reverse phase HPLC (water/acetonitrile, Varian DYNAMAX C18 column (250×10.0 mm)). MALDI-TOF: 1220.553 [M+Na]+. 1H-13C HSQC NMR: FIG. 11.

Synthesis of 13 nm AuNPs

An aqueous solution of HAuC14 (1 mM, 500 mL) was brought to reflux while stirring, and then trisodium citrate solution (50 mL, 77.6 mM) was added quickly to the boiling mixture. The solution was refluxed for an additional 15 minutes, and allowed to cool to room temperature. The average diameter of the gold nanoparticles was determined by TEM (12.8±1.2 nm). AuNPs of other sizes used in this study were purchased from Ted Pella.

General Method for the Preparation of Nanoconjugates

To 10 mL AuNP solution (10 nM), 10 μL of 10% sodium dodecyl sulfate solution was added. Then, an aqueous solution containing 1 was added to give a final concentration of 20 nM. The solution was stirred for 2 days before being subjected to centrifugation using an Eppendorf 5424 centrifuge at 15,000 rpm for 30 minutes. Supernatant was removed by careful pipetting, and the AuNP was resuspended in nanopure water. The process was repeated three times to ensure complete removal of excess polymers. After the final centrifugation, the polymer-coated AuNP were concentrated to 1 mL, and 50 μL of 1.0 M KCN aqueous solution was added to remove the gold core. The resulting solution was then dialyzed against nanopure water (>18.0 MΩ.cm) using pre-soaked dialysis tubing (MWCO=6-8 kDa) for 3 days. The final nanoconjugate solution appeared clear and slightly yellow. A large volume of gold nanoparticle templates (>500 mL) was required to prepare sufficient quantity of nanoconjugates for NMR and IR analyses.

Example 2

In searching for appropriate orthogonal chemistries that could crosslink a dense monolayer of DNA together on the gold surface, it was discovered that poly-alkyne bearing DNA strands autocrosslink on the gold nanoparticle surface without any additional catalysts. In initial experiments, DNA strands were synthesized that utilized synthetically modified bases that could be modified with desired chemical moieties. Because of the modular nature of phosphoramidite chemistry, these bases are incorporated into a polynucleotide sequence at any location. The modified base that was chosen for this system is an amine-modified thymidine residue that can be reacted with an alkyne-NHS ester to produce an alkyne modified thymidine within the sequence (FIG. 1). However, any moiety that can be converted to an alkyne can be used. Strands were then synthesized that incorporated a thiol moiety for attachment, a crosslinking region (CR) of 10 amine-modified T monomers a spacer of 5 T residues, and a programmable DNA or RNA binding region (BR). The CR was then modified with the alkyne NHS ester, which resulted in a strand with 10 alkyne units in the BR. Two example sequences used were 5' TCA-CTA-TTA-TTTTT-(alkyne-modified T)10-SH 3' (SEQ ID NO: 1) and 5' TAA-TAG-TGA-TTTTT-(alkyne-modified T)10-SH 3' (SEQ ID NO: 2).

In a typical experiment, 1 O.D. of DTT-treated alkyne-DNA is added to 1mL of 13 nm gold nanoparticles at a concentration of approximately 10 nM. Polysorbate 20 (Tween-20) and phosphate buffer (pH 7.4) are then added to the nanoparticles for a final concentration of 0.01% Tween-20 and 50 mM phosphate buffer. Because the polynucleotides must be as close as possible for crosslinking, the nanoparticles were brought up to a high sodium chloride concentration of 1.0 M to maximize loading. The particles were then centrifuged (13.2 k rpm) and resuspended in PBS/SDS three times to remove excess DNA.

Figure 2:
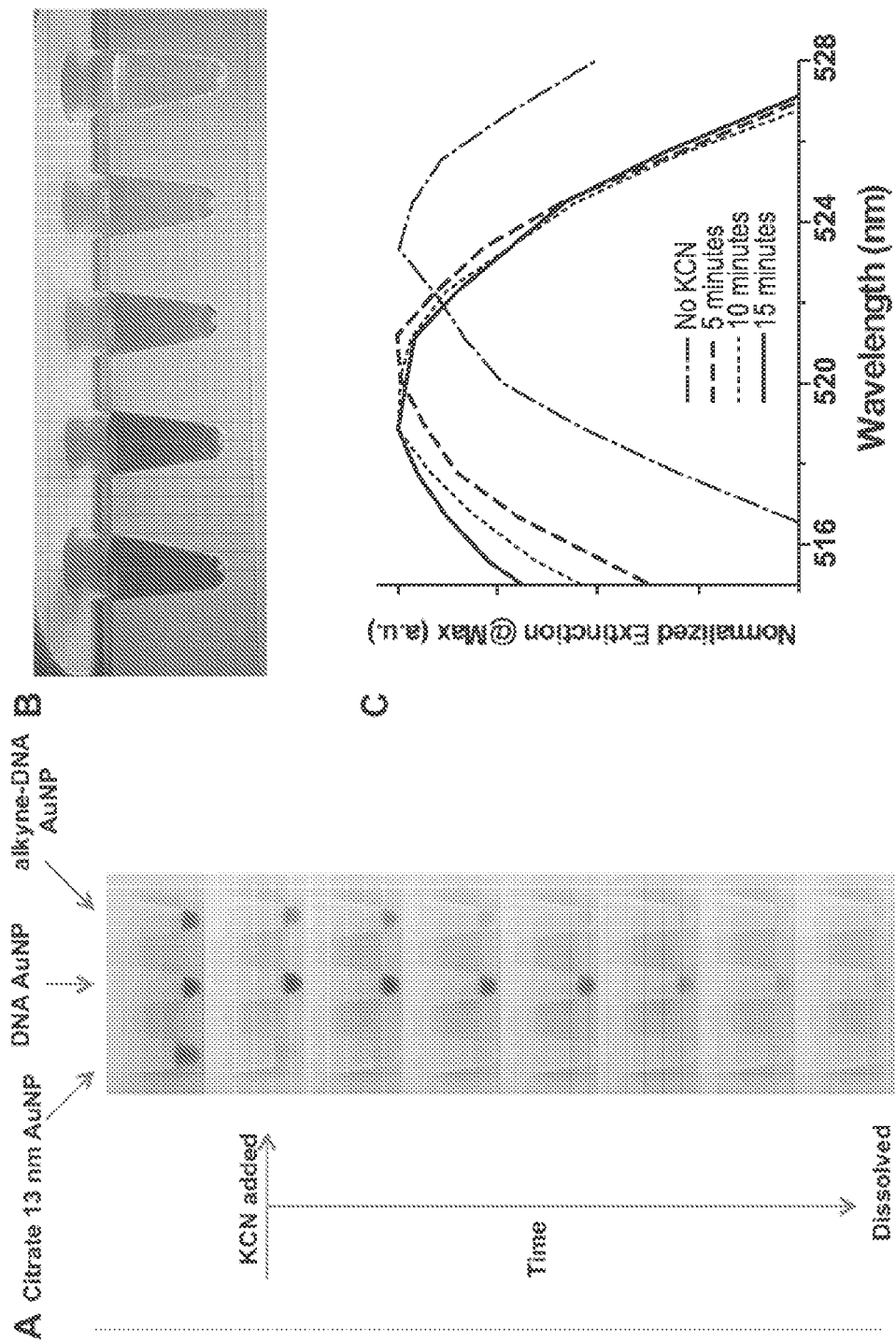
FIG. 2 shows A) Dissolution of multiple citrate stabilized, DNA functionalized, and alkyne-DNA functionalized AuNPs. B) Alkyne-DNA functionalized AuNPs at various stages in the dissolution process. C) UV-Vis spectra of the corresponding time points in B.

Dissolution of the AuNP core was achieved by using KCN in the presence of oxygen. When KCN was added to citrate stabilized AuNPs, the color of the solution instantly changed from red to purple, resulting from the destabilization and aggregation of the AuNPs (FIG. 2A). A similar effect is observed for AuNPs densely functionalized with thiolated polynucleotides, but the process is slower (FIG. 2A). However, for the alkyne-DNA AuNP, the color slowly changed to a slightly reddish orange color during the dissolution process until the solution was clear (FIG. 2B). This observation suggested that the alkyne modified DNA formed a dense crosslinked shell, which prevented the typical aggregation that is typical of AuNPs being oxidatively dissolved. Furthermore, UV-Vis spectra showed a gradual decrease of the plasmon resonance from 524 nm to 518 nm (FIG. 2B), as expected from the decrease of AuNP size (FIG. 2C) [Link et al., J. Phys. Chem. B 103(21): 4212-4217 (1999)].

Figure 3:
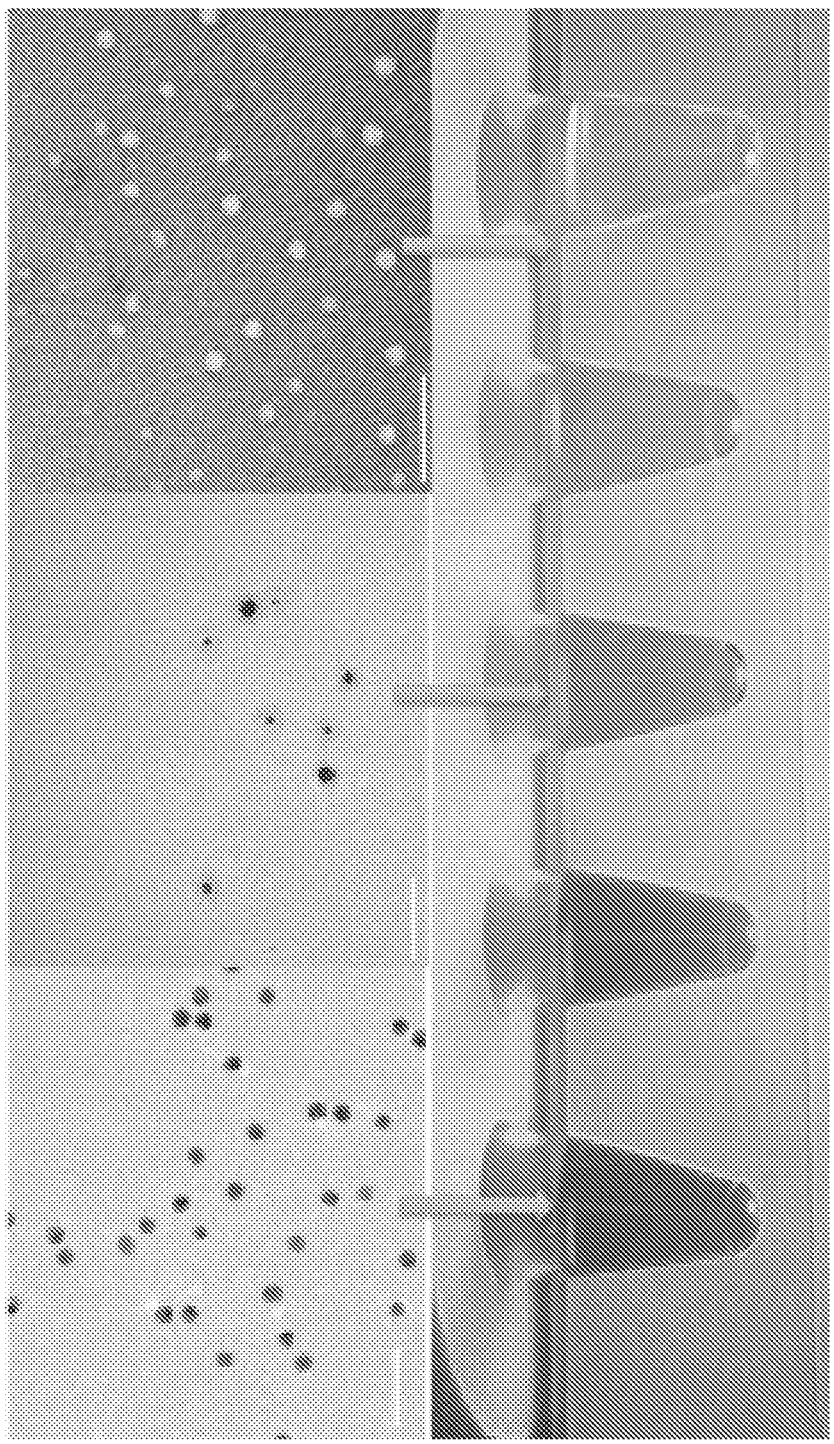
FIG. 3 shows TEM images of the indicated solutions of gold nanoparticles during the dissolution process.

After dialysis, the structures were analyzed by TEM at different stages of the dissolution process with uranyl acetate staining (FIG. 3). The dissolution reaction was quenched by rapid spin filtering, which removes all of the KCN and retains the particles on the filter. It was clear that as the particles dissolve, a dense ligand shell is responsible for the particles' remarkable stability in KCN. At an intermediate time point, staining revealed a dense shell around the particle surface as the particle shrank in size. After the dissolution process was complete, spherical particles of DNA could clearly be observed.

Example 3

Figure 4:
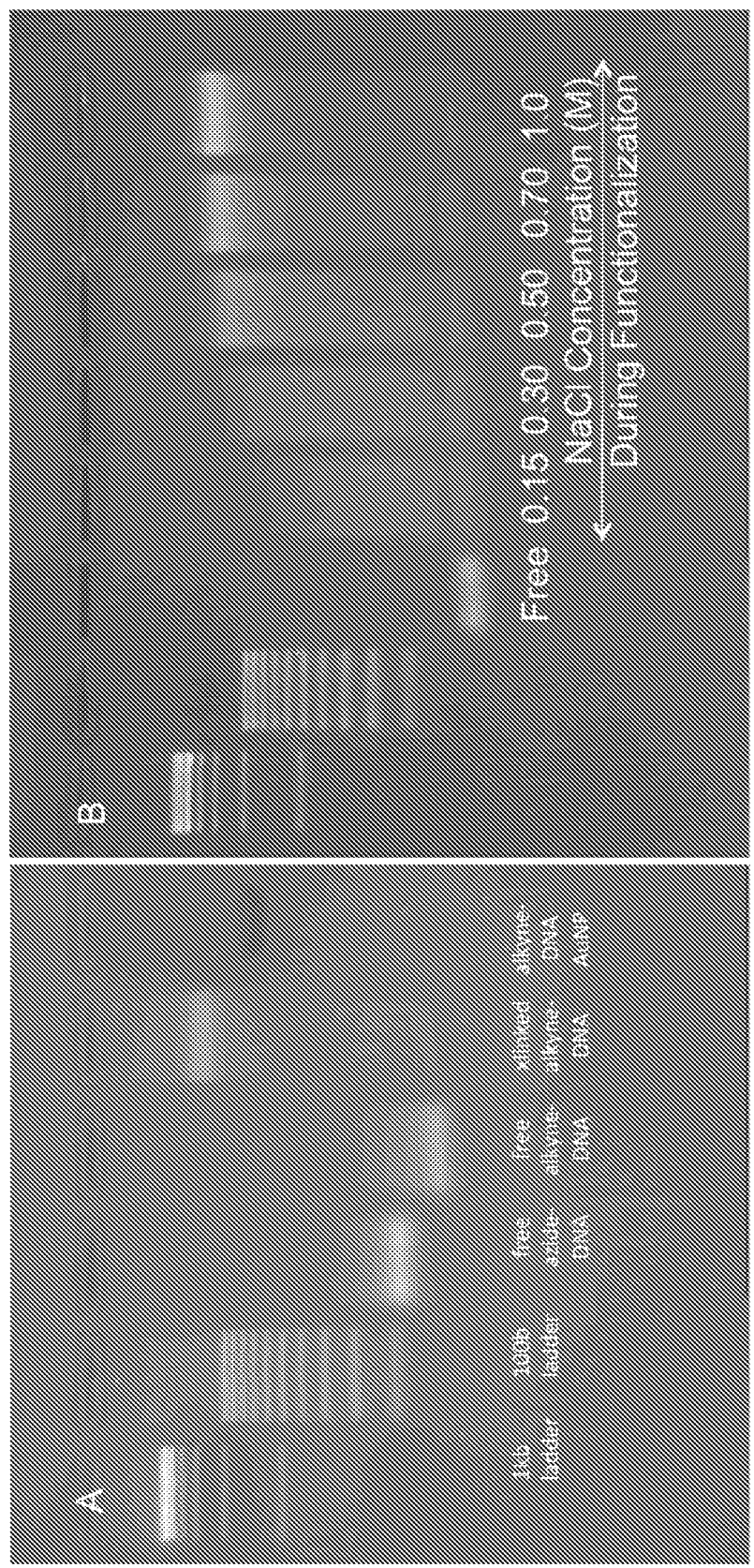
FIG. 4 shows A) Gel electrophoresis comparison of free strand DNA to crosslinked structures and DNA functionalized AuNPs. B) Gel electrophoresis analysis of crosslinked structures obtained from alkyne-DNA-AuNPs with a range of densities.

Because these structures were made almost entirely of DNA, gel electrophoresis was a powerful method to analyze the completeness of the crosslinking reaction and the quality of the resulting structures. After dialysis, the unreacted alkyne-DNA strand was compared with the particles formed from the templated method. The hollow particles migrated much more slowly than the free strands and similarly to the undissolved DNA-AuNP conjugate. Next, the role the density of the DNA plays in the formation of these hollow DNA nanoconjugates was analyzed (FIG. 4). The density of the DNA on the nanoparticle surface could easily be controlled with the concentration of sodium ions in the DNA/gold nanoparticle solution during functionalization. At low DNA surface densities, it was clear that a distribution of crosslinked products was obtained, and with increasing surface density, a dramatic increase in the size of the crosslinked products was evident. At a critical density obtained from particles salt-aged to 0.5 M NaCl, a sharp band appeared at high molecular weight numbers. This band became the majority product (approximately 99% by densitometry) from particles that were salt-aged to 1.0 M NaCl, which have the maximum surface densities.

Example 4

Figure 5:
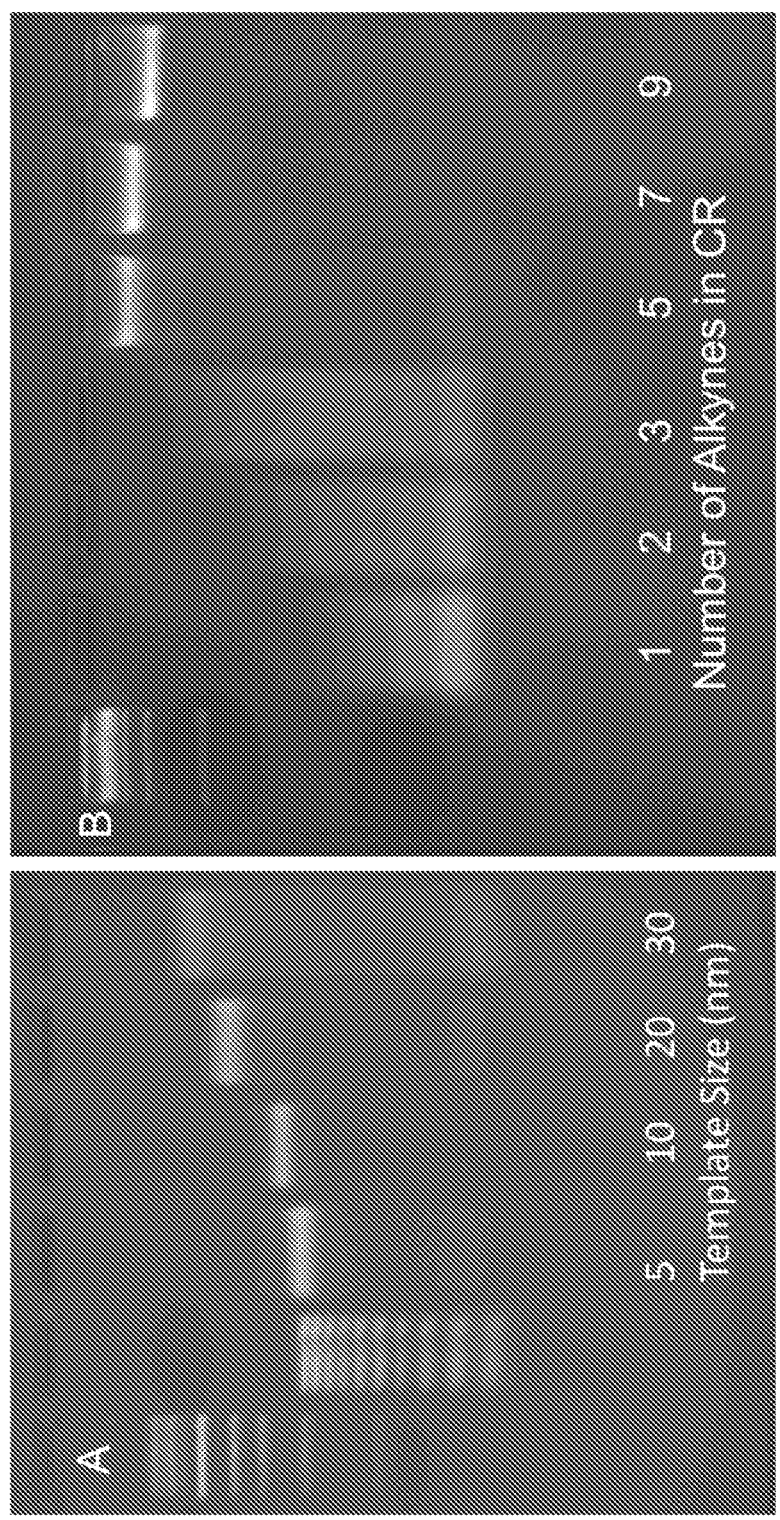
FIG. 5 depicts A) Gel electrophoresis of hollow DNA nanoconjugates formed from a range of different sized templates. B) Gel electrophoresis of crosslinked structures obtained from AuNPs functionalized with alkyne-DNA that were modified with varying numbers of alkyne units.

Next, the ability to obtain hollow DNA nanoconjugate from gold nanoparticles of a range of sizes was tested. Indeed, the migration of the hollow particles through the gel was directly related to the size of the resulting hollow structures, with larger hollow particles migrating slower than the small ones (FIG. 5A). The number of alkynes in the CR was then varied, while keeping the number of total residues constant, to determine the minimum alkyne density of this process (by way of example, a strand with 3 alkynes has 7 unmodified T residues in the CR). At a threshold of approximately 5 alkynes in the CR, particles of a similar size to the ones from the previous experiment are obtained (FIG. 5b). However, as the number of alkyne units is increased from 5 to larger numbers, the particles migrated slightly faster, which indicates more densely crosslinked nanoconjugates.

Example 5

After establishing that this method could produce nanoconjugates composed entirely of crosslinked DNA, their functional properties were investigated. When polynucleotides are densely arranged on a AuNP's surface, many new behaviors emerge including but not limited to elevated and narrow melting transitions, enhanced binding to targets, reversible directed assembly, high cellular uptake without transfect agents, dramatic nuclease resistance and robust antisense/RNAi engagement. These properties emerge due to the dense polyvalent arrangement of DNA on the gold nanoparticle's surface. So, if the DNA in the hollow nanoconjugate maintained their binding ability, the binding properties characteristic of polyvalent DNA would be observable.

Figure 6:
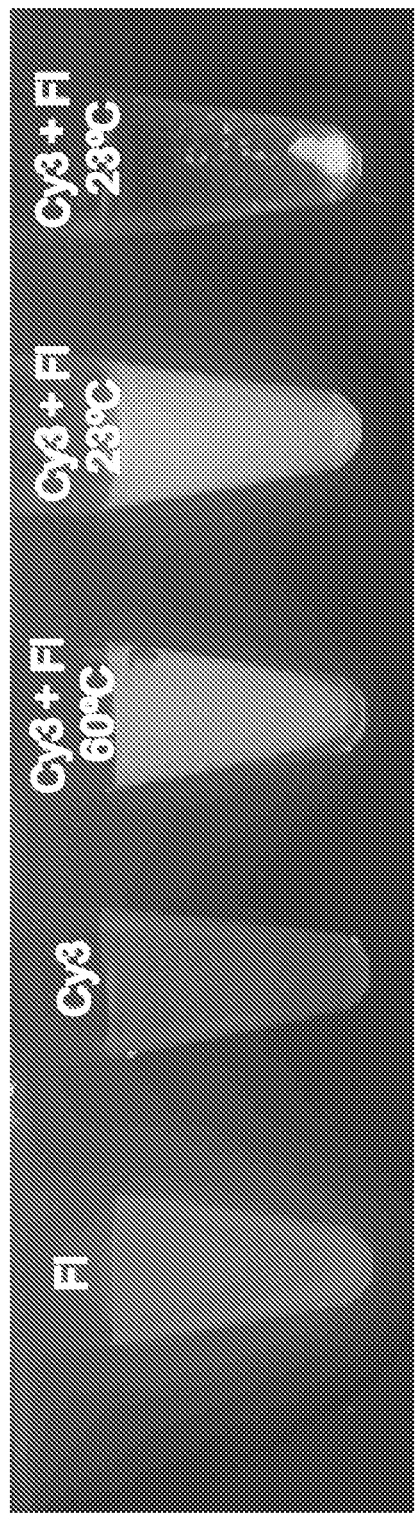
FIG. 6 shows the two strand system of Fl and Cy3 modified hollow DNA nanoconjugates. At 60° C., these particles were dehybridized and the green fluorescence of fluorescein was observed. At room temperature, the particles hybridized and FRET from fluorescein to Cy3 produced the orange fluorescence of Cy3. After time, these particles form macroscopic aggregates that settle out of solution.

To that end, a two nanoparticle system was designed wherein the strands on the nanoparticles were designed such that there is no self complementarity within one sequence, so particles functionalized with one of the strands will be stable in solution. However, when the two particles are mixed together, the complementarity of the strands will bring together nanoparticles into a macroscopic polymeric assembly. Because the hollow nanoconjugates have no absorbance in the visible spectrum, in contrast to AuNPs that have very strong visible optical properties, the system was designed to include fluorescence resonance energy transfer (FRET) active fluorophores (Fluorescein (Fl) and Cy3) at the end of the sequences. Therefore, when the particles hybridize, Fl will transfer energy to Cy3, and the orange fluorescence of Cy3 is observed. Hollow DNA nanoconjugates were synthesized successfully with these new strands, and showed similar migration through an agarose gel. Fluorescein can be excited with a UV light source, whereas Cy3 cannot. A solution of Fl modified particles appeared bright green and the Cy3 particles exhibited no typical orange fluorescence. However, when these particles were mixed together, the orange fluorescence of Cy3 was easily visible under a UV lamp. After time, these particles formed macroscopic aggregates that settled out of solution over time (FIG. 6). Interestingly, when these particles were heated, the bright green fluorescence of fluorescein was visible, indicating that this process was reversible. This engineered green to orange color change is analogous to the red to purple shift evident when DNA-AuNPs are similarly hybridized.

That these particles formed macroscopic aggregates over time indicated they are binding in a cooperative fashion analogous to DNA-AuNP aggregates. A UV-Vis melting assay was conducted to analyze the degree of cooperativity between particles. It is well known that the density of the DNA on a nanoparticle's surface is directly related to the breadth and temperature of the melting transition of the resulting aggregates [Jin et al., J. Am. Chem. Soc. 125(6): 1643-1654 (2003)].

Figure 7:
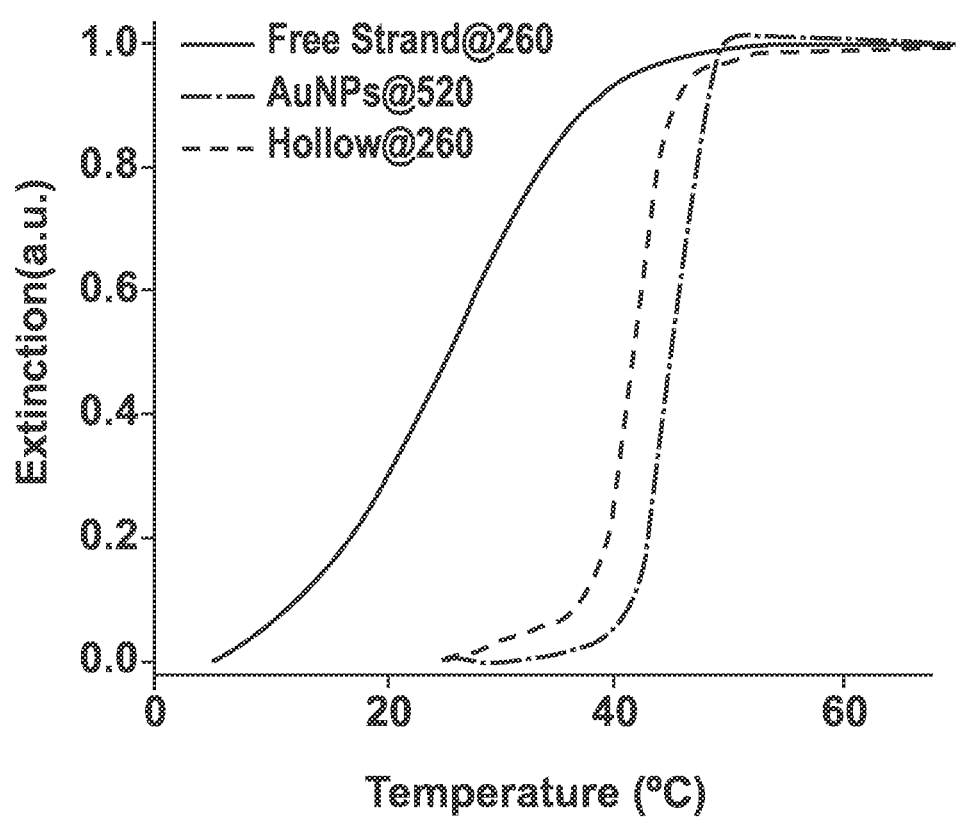
FIG. 7 depicts extinction as a function of temperature for free strand DNA at 260 nm. DNA-AuNP aggregates formed from these strands at 520 nm and hollow DNA nanoconjugate aggregates at 260 nm formed from the same strands.

The extinction of the free strand, DNA-AuNP aggregates and hollow DNA aggregates were monitored at 260 nm of light as a function of temperature (FIG. 7). The free strands in this system had a melting transition at approximately 23° C. When AuNPs were functionalized with these strands and mixed together, the typical red to purple plasmonic shift occurs, and aggregates were formed [Mirkin et al., Nature 382(6592): 607-609 (1996)]. These aggregates melted sharply (full width at half maximum (FWHM) of the derivative of the melting transition was approximately 2° C.) at approximately 43° C. as expected. The aggregates formed from the hollow nanoconjugates exhibited a similarly sharp melting transition at approximately 40° C., with the FWHM of the derivative of the melting transition spanning approximately 2° C. This extremely similar melting behavior was a direct indication that the polyvalent melting behavior associated with the DNA-AuNP conjugate was preserved after crosslinking of the ligand shell and dissolution of the gold core.

Example 6

Having demonstrated that hollow DNA nanoconjugates maintain the size, shape, and function of their DNA-AuNP counterparts, their effectiveness as gene regulation agents was next investigated. RNA hollow particles were synthesized in the same fashion as DNA hollow particles, but in this case a DNA/RNA chimera was used, wherein the CR of the strand still comprised 10 alkyne-T units, and the CPGs from the synthesis were transferred to the RNA synthesis to complete the synthesis. Additionally, the antisense RNA strand was labeled with Cy5, so that the hollow particles would be visualized in cells with fluorescence microscopy. After dialysis of the hollow particles, the antisense complement of the crosslinking strand was added to the hollow particles in a 100-fold excess to form duplexes on the surface of the particles. HeLa cells were transfected with these particles for 24 hours and imaged with confocal microscopy. Particles harvested after transfection were visibly blue as compared to untreated cells, which indicated a very high number of particles within the cells.

Figure 8:
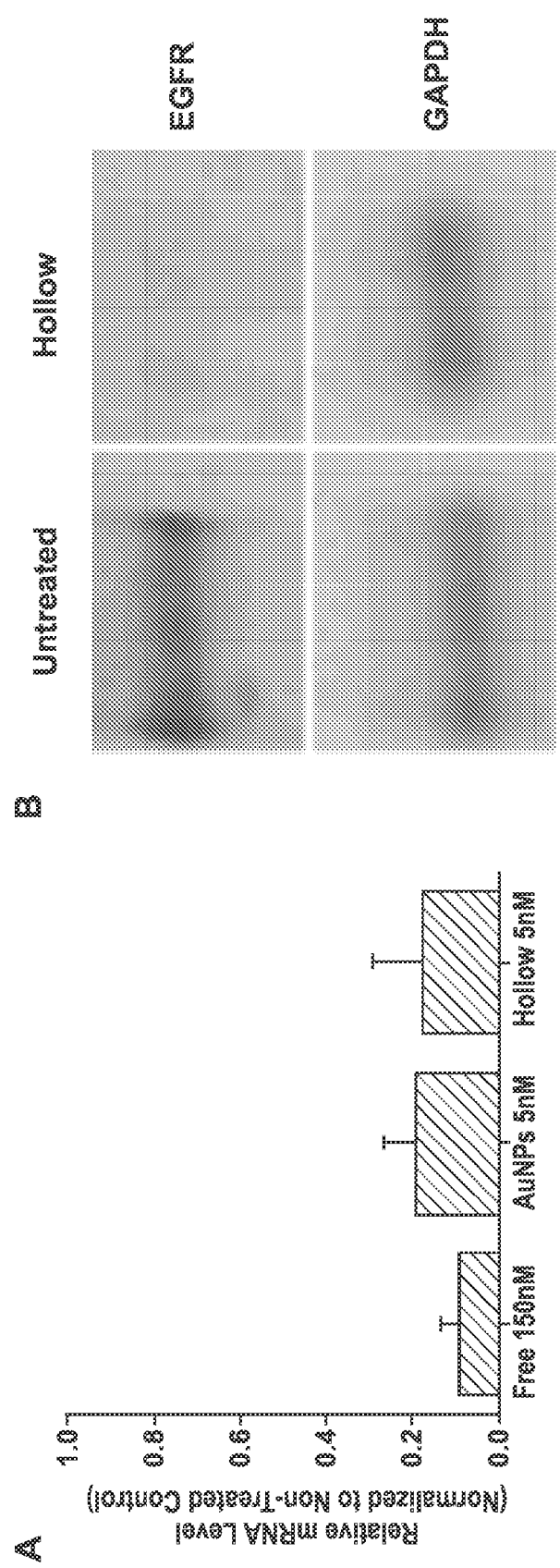
FIG. 8 depicts A) RT-qPCR quantification of EGFR mRNA for cells treated with dharmafect (free), siRNA-AuNPs and siRNA-hollow nanoparticles normalized to GAPDH. B) Western blot for EGFR and GAPDH in cells treated with siRNA-hollow nanoparticles.

RNA sequences targeted against EGFR were then synthesized. EGFR is an important target associated with cancer. SCC12 (human squamous carcinoma) cells were transfected for various periods of time (48, 72, 96 hours) and harvested for their protein and mRNA content. Initial experiments showed robust knockdown of EGFR normalized to a reference gene, GAPDH (FIG. 8A). Furthermore, western blots showed significant knockdown of EGFR as compared to untreated cells (FIG. 8B).

Example 7

The above examples show that hollow nanoconjugates can be created; next, the nature of the chemistry in this process was investigated. To that end, multiple model systems were created to investigate the mechanism of formation for these structures. All of these model systems incorporated alkynes into the ligand shell for crosslinking. A polymer system, a single alkyne DNA system, and a single alkyne PEG system were designed.

A polymer with alkyne moieties 1 was readily prepared through post-polymerization modification of polyacrylamidoethylamine120 with a narrow polydispersity index of 1.10 [Zhang et al., Biomaterials 30 (5), 968-977 (2009)]. Containing no charged groups, 1 exhibited moderate solubility in water at room temperature. Solubility increased at lower temperatures. Bearing multiple side-arm propargyl ether groups, 1 readily adsorbed onto citrate-stabilized 13 nm AuNPs prepared in an aqueous solution by the Turkevich-Frens method (See Scheme 1). Excess polymers were removed by multiple centrifugation-resuspension steps. The resulting polymer-coated AuNP retained the plasmon resonance at 524 nm and was stable for months, in contrast to the unmodified polyamine polymer, which crashes the particles instantaneously under the same conditions.

Dissolution of the AuNP core was achieved using 1 mM KCN in the presence of oxygen. When KCN was added to citrate stabilized AuNPs, the color of the solution instantly changed from red to purple, resulting from the destabilization and aggregation of the AuNPs. However, for the polymer-coated AuNP, the color slowly changed to a slightly reddish orange color during the dissolution process until the solution was clear (FIG. 9A). This observation suggested that 1 formed a dense crosslinked shell, which prevented the typical aggregation that is typical of AuNPs being oxidatively dissolved. Furthermore, UV-Vis spectra showed a gradual decrease of the plasmon resonance from 524 nm to 517 nm (FIG. 9B), as expected from the decrease of AuNP size.

Figure 10:
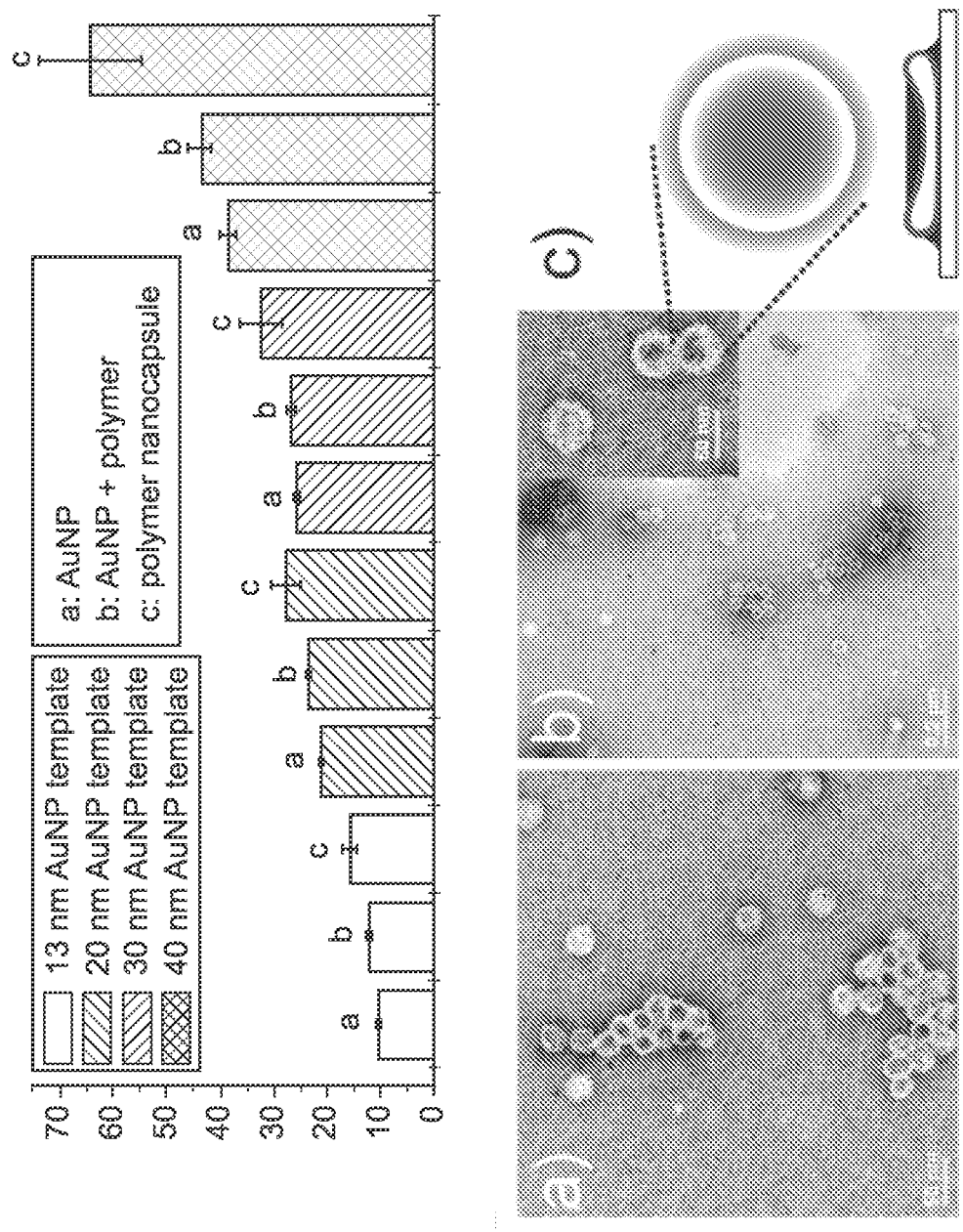
FIG. 10 shows A.) Number-average hydrodynamic diameters of AuNPs (13, 20, 30 and 40 nm), polymer-coated AuNPs and polymer nanoconjugates (PNSs) measured by dynamic light scattering. B.) TEM images of a) 20 nm PNSs and b) 40 nm PNSs (negatively stained with 0.5% uranyl acetate). In c) it is illustrated why nanocapsules appear as donut-shaped in TEM. Black: uranyl acetate stain. Blue: a collapsed PNS on a surface.

The dissolution process was visualized by transmission electron microscopy (TEM) (FIG. 9C). As the outer layer of the AuNP was partially dissolved, the protective shell mentioned above was observed with uranyl-acetate staining of the TEM grid. Complete removal of the template afforded hollow nanoconjugates that retained the size and shape of their template in high fidelity. When AuNP templates over a range of sizes were used (10, 20, 30 and 40 nm), the sizes of the resulting polymer nanoconjugates (PNSs) were directly related to the size of the original template as measured by dynamic light scattering (DLS) and TEM (FIG. 10). These results indicated that the AuNP can serve not only as the template but also the catalyst for the formation of the PNSs through the alkyne moieties. However, they raised the question as to what kind of chemical pathway was accessed in the transformation of 1 to the resulting PNS.

Example 8

IR spectroscopy of 1 before and after crosslinking on the surface of 13 nm AuNPs showed the complete loss of the acetylene C≡C stretching (2114 cm-1), C—H stretching (3805 cm-1) and bending (1274, 646 cm-1) vibrations, indicating that the propargyl ether group was involved in the reaction. NMR spectroscopy of the PNSs made from 13 nm AuNP was not possible, perhaps due to reduced solvent accessibility to the relatively large structures (FIG. 11D).

Figure 17:
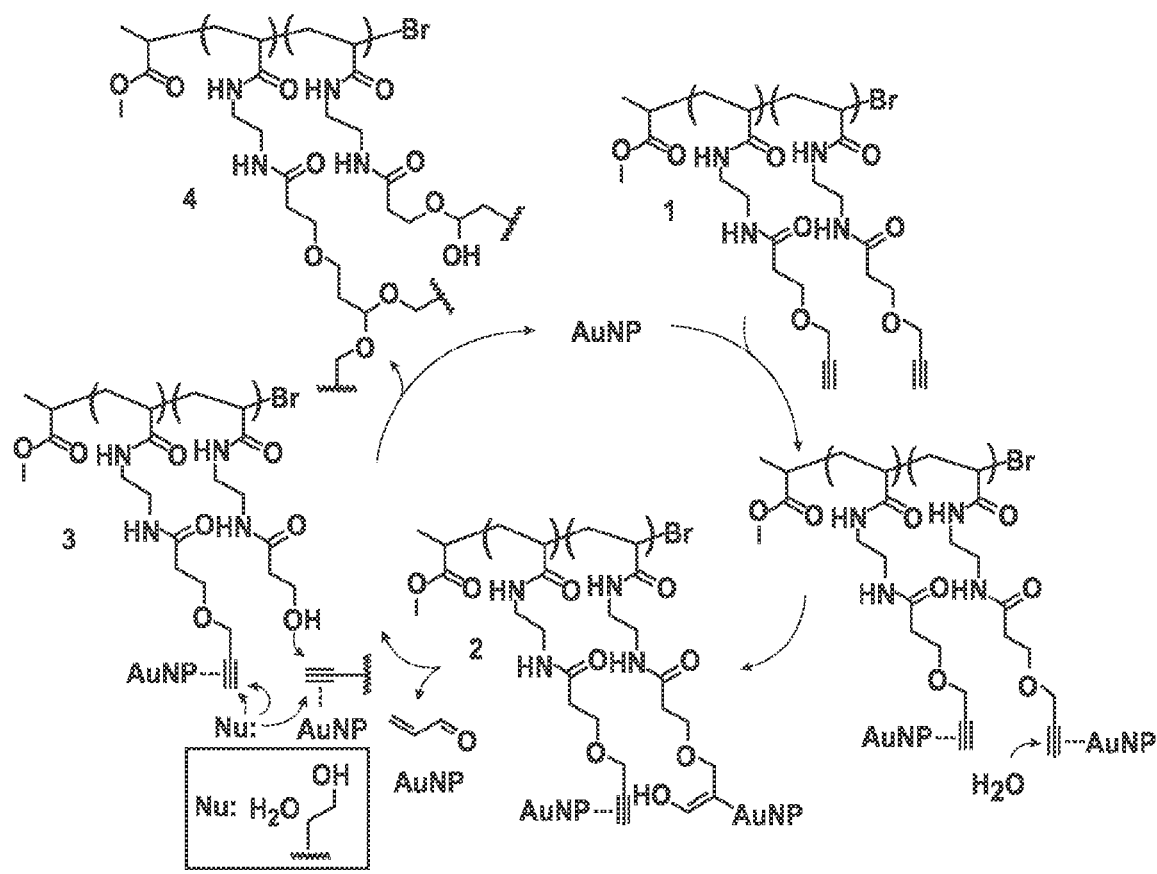
FIG. 17 depicts a potential pathway for poly alkyne crosslinking.

However, 5 nm AuNPs produced PNSs that were suitable for analysis. 1H and 13C NMR spectroscopy showed the loss of resonances from the propargyl group, which is likely to leave behind a hydroxyl group through elimination of acrylaldehyde (FIG. 11B) [Fukuda et al., Bull. Chem. Soc. Jpn. 64: 2013-2015 (1991)]. The resulting hydroxyl group could then serve as a new nucleophile for remaining alkyne-Au complexes to generate acetal linkages [Fukuda et al., J. Org. Chem. 56(11): 3729-3731 (1991)]. Indeed, 1H-13C HSQC spectra showed the appearance of resonances from the α-H of primary alcohol ($\delta$ 3.81 ppm, 1H), alkyl ether ($\delta$ 3.74 ppm, 1H) and acetal ($\delta$ 4.32 ppm, 1H) groups. Such transformations are previously known to be possible only with ionic gold catalysts. Without being bound by theory, a plausible pathway can be proposed (FIG. 17).

Coordination of the alkynophilic AuNP to 1 is followed by the nucleophilic addition of water to yield intermediate 2, which forms 3 by elimination. Because of high local concentrations on the surface of the AuNP, reaction between the hydroxyl groups and Au-alkyne complexes is possible without high temperatures, giving acetal and ether crosslinks 4 with regeneration of the catalytic AuNP surface sites. However, the AuNP cannot catalyze further reactions because the dense shell that forms should prevent access of free polymers.

Indeed, the polymers remaining in solution were found to be exclusively the starting material 1. Furthermore, this pathway also indicates that a single alkyne moiety can form a 3-arm crosslink.

Figure 11A:
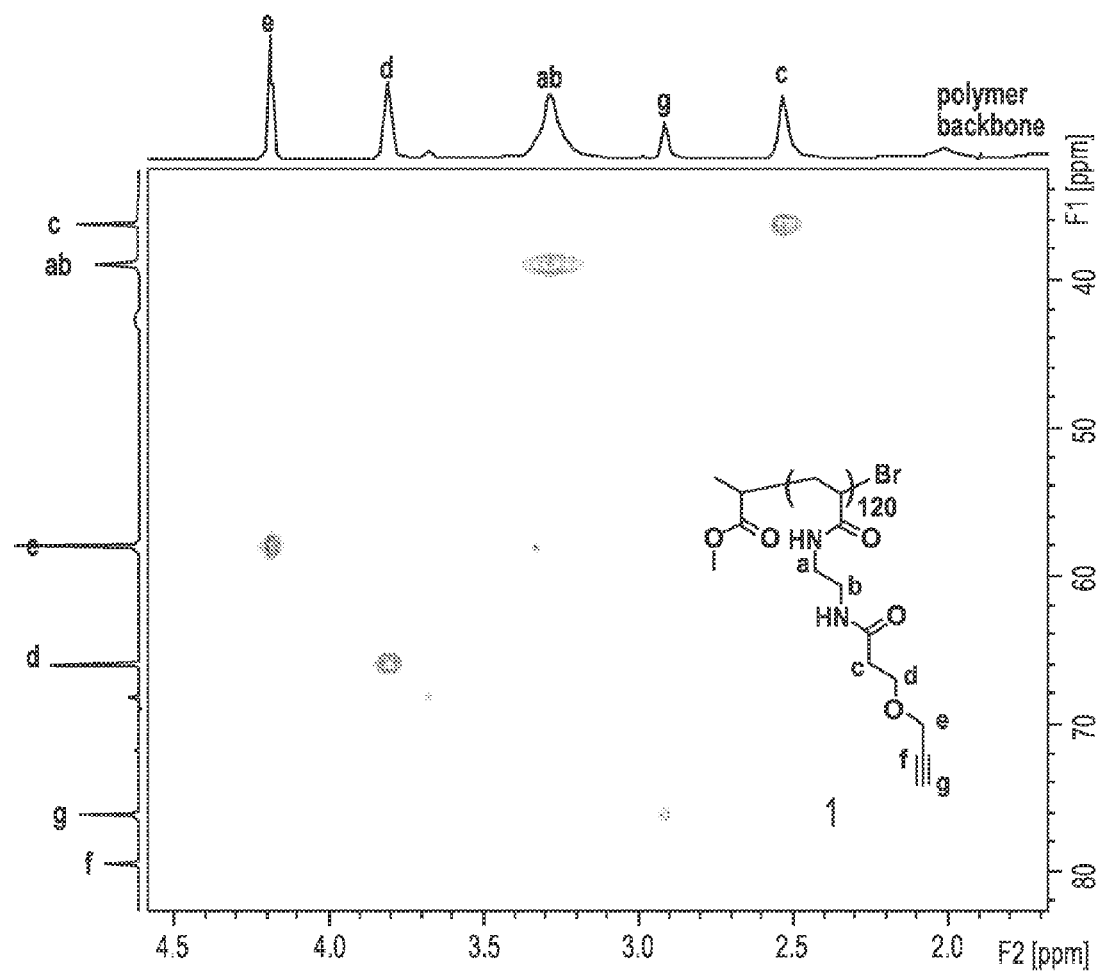
FIG. 11 shows A.) 1H-13C NMR spectrum of 1. B.) 1H-13C NMR spectrum of 4. C.) 1H-1H COSY of 4. D.) IR spectrum of 1 (dashed line) and 4 (solid line).
Figure 11B:
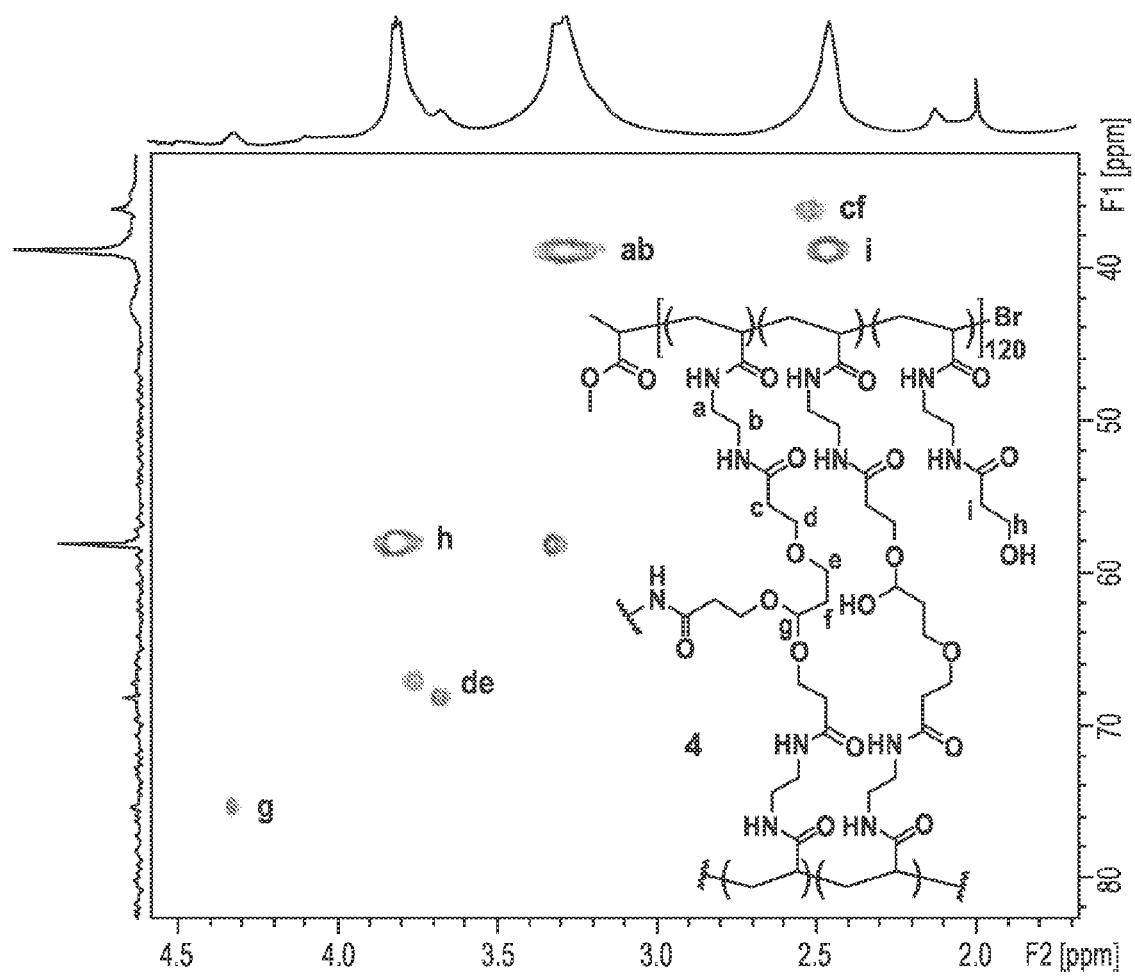
Figure 11C:
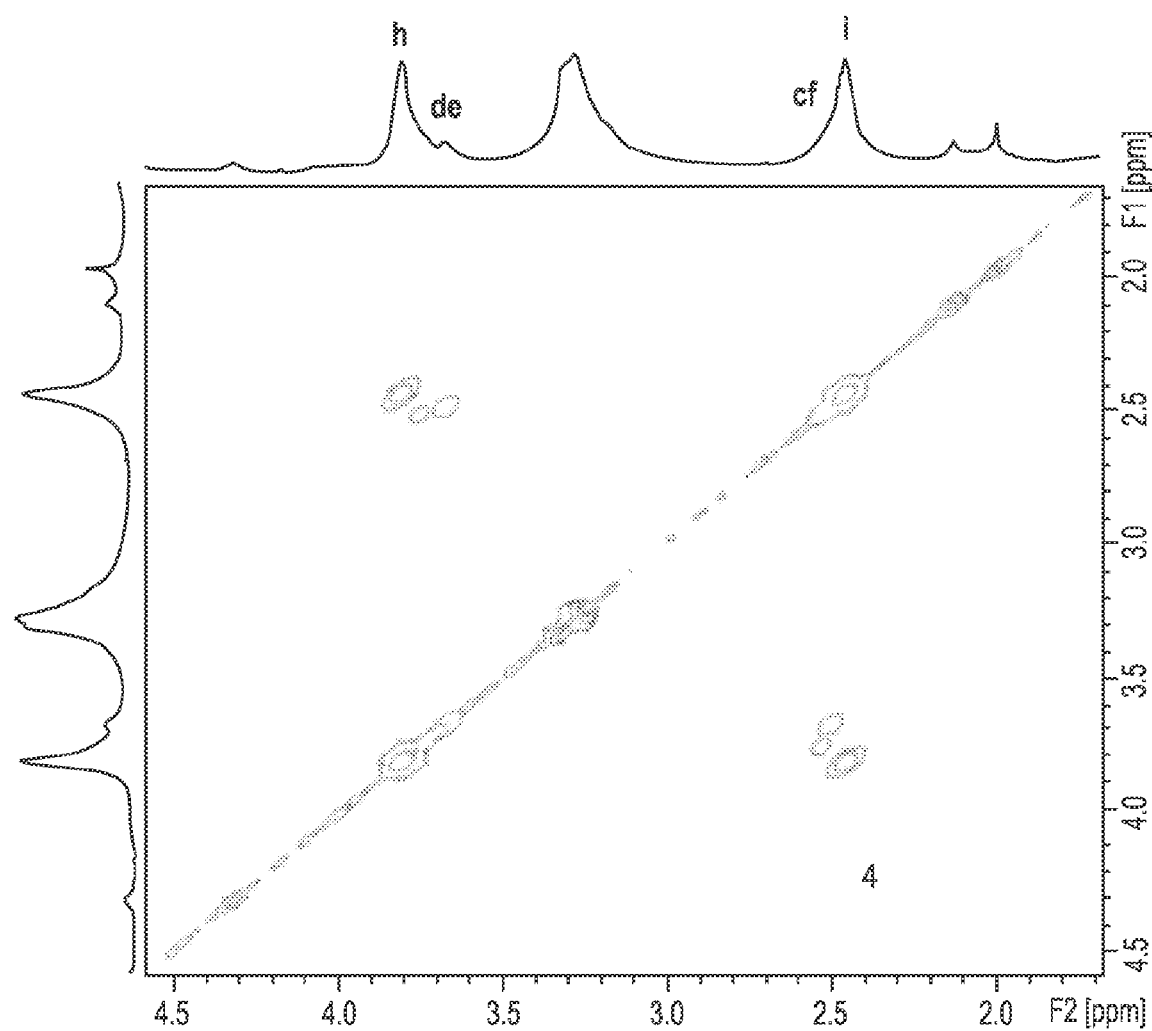
Figure 11D:
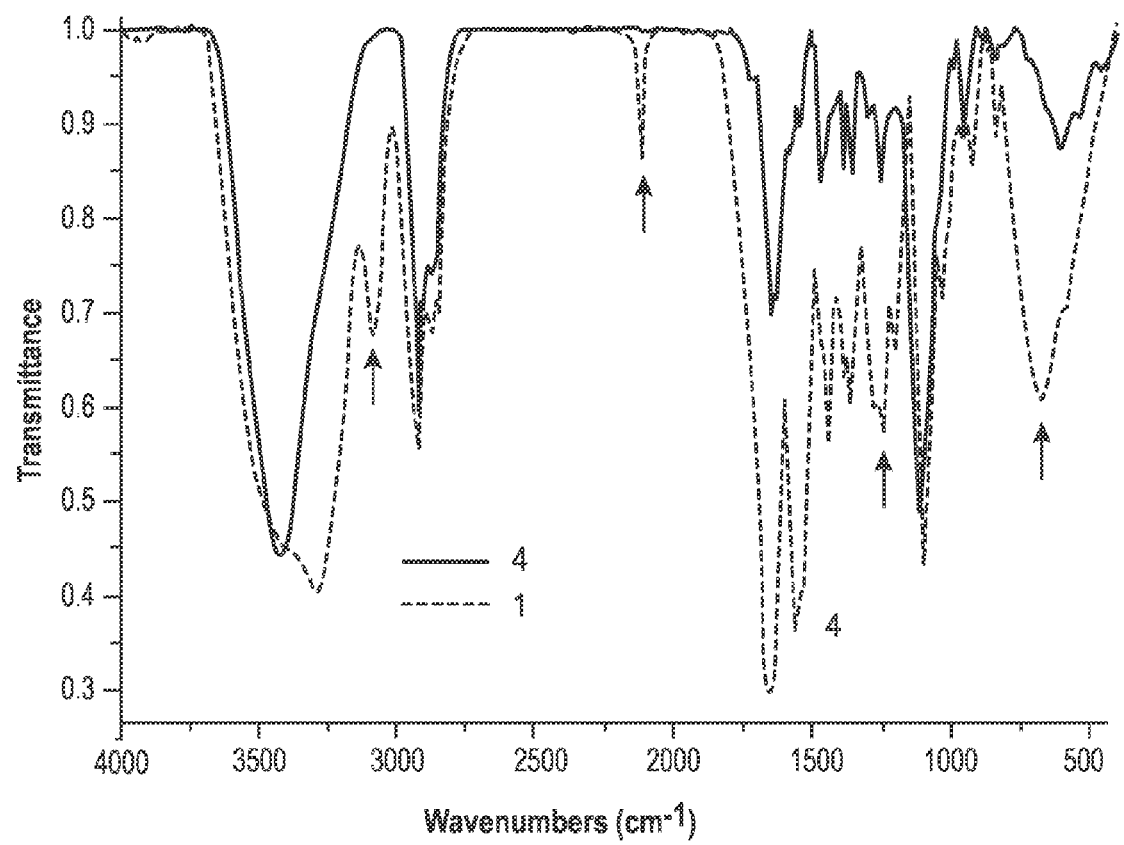
Figure 13:
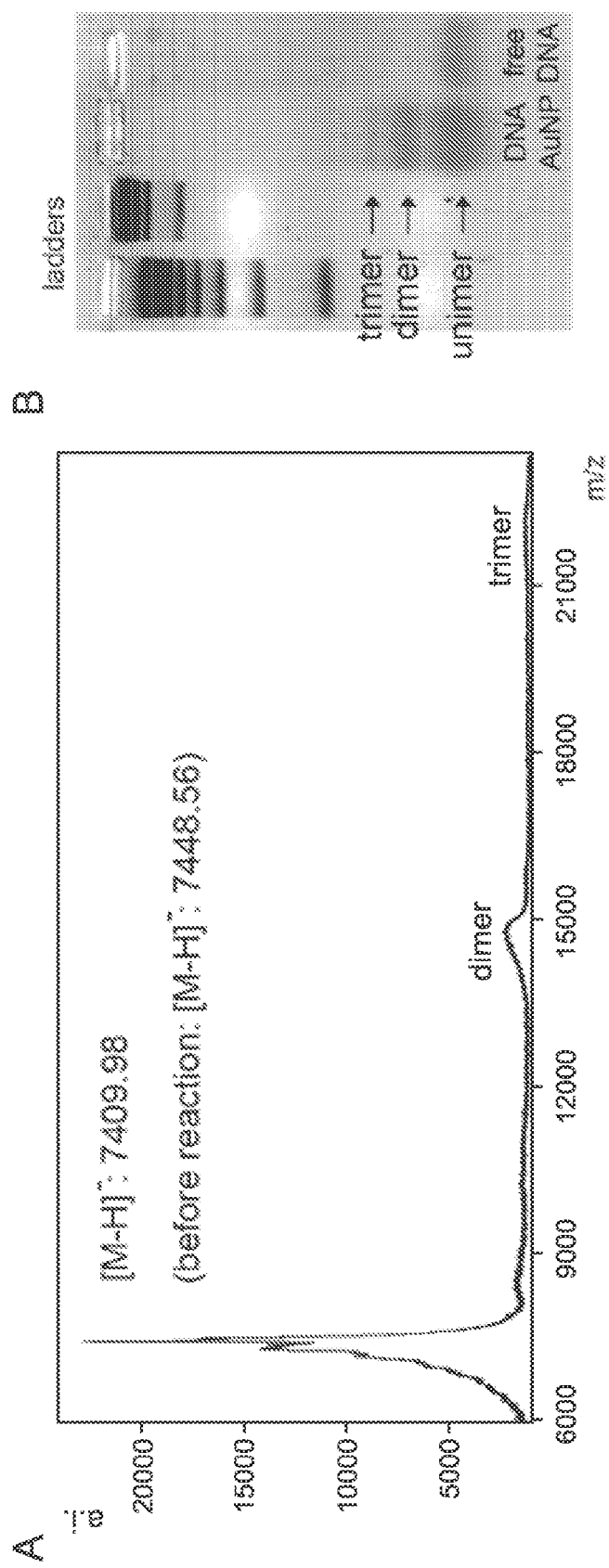
FIG. 13 shows A) MALDI-TOF of DNA-propargyl ether conjugate 6 after incubation with AuNP. B) Agarose gel (3%) electrophoresis of 6 after incubation with AuNP of 6, con-firming the prediction of the proposed crosslinking mechanism that a 3-arm crosslink is possible with a single acetylene group (FIG. 12).

To support the proposed mechanism, a monodisperse poly (ethylene glycol)24-propargyl ether conjugate 5 was synthesized, which allowed for convenient mass and NMR analyses (FIG. 11B). Upon incubation with AuNP, 5 was converted to a primary alcohol quantitatively as evidenced by matrix-assisted laser desorption/ionization time-of-flight mass spectrometry (MALDI-TOF MS) and NMR spectroscopy (FIG. 12). To demonstrate that the chemistry is compatible with complex molecules containing various functional groups, a DNA-derivatized alkyne 6 was synthesized, and incubated with AuNP. Again, 6 was found to lose 38 mass units to give a primary alcohol. More interestingly, from agarose gel electrophoresis and MALDI-TOF MS, dimers and trimers were observed (FIG. 13).

Example 9

Next the polymer that was synthesized was utilized in a functional model system. Functional proteins can be incorporated into the outer shell of the polymer nanoconjugates by co-forming the shell on the AuNP template with polyvalent propargyl ether 1 (FIG. 14A). Such constructs are termed proteonanoconjugates. As a demonstration, streptavidin and horseradish peroxidase (HRP) were used as model proteins. Streptavidin can bind to surfaces with tethered biotin moieties, thereby immobilizing the proteonanoconjugate. If present, HRP can then provide a means of readout by catalyzing a chromogenic reaction between tetramethylbenzidine (TMB) and hydrogen peroxide. In principle, only when both proteins are present in the proteonanoconjugates, and when both proteins remain active after the AuNP dissolution process, will a signal be observed (FIG. 14B). Indeed, signal was only observed when streptavidin, HRP and polymer 1 were used in the creation of the proteonanoconjugate shell (FIG. 15). Absence of either HRP or polymer 1 rendered the system non-functional.

Example 10

The present disclosure provides, in various aspects, methods for crosslinking polynucleotides on a nanoconjugate. This example provides additional methods for effecting the crosslinking. As described above, the additional methods include DSC and SAC.

In a typical experiment, 1 O.D. of DNA is added to 1 mL of 13 nm gold nanoparticles at a concentration of approximately 10 nM. Polysorbate 20 (Tween-20) and phosphate buffer (pH 7.4) are then added to the nanoparticles for a final concentration of 0.01% and 50 mM, respectively. Because the polynucleotides must be as close as possible for crosslinking, the nanoparticles are brought up to a high sodium chloride concentration of 1M to maximize loading. The particles are then centrifuged (13.2 k rpm) and resuspended in PBS/SDS three times to remove excess DNA.

The crosslinking step is performed by the slow addition of Sulfo-EGS to a final concentration of 1 μM. A slow addition is necessary to prevent interparticle crosslinking, and also to prevent saturation of the DNA strands with crosslinker, which would result in no crosslinking. The solution retains its bright red color, and no aggregation is observed. The particles are then purified by centrifugation (3 times at 13.2 k rpm) and are ready to be dissolved.

To dissolve the gold core, potassium cyanide is added to the nanoparticle solution. As the particles dissolve, the bright red color of the solution fades completely, resulting in a clear solution. Interestingly, in comparison to particles that have been functionalized with the amine-modified strand but have not been cross-linked, the cross-linked particles take a significantly longer time to dissolve. Non-crosslinked particles are dissolved within a minute, but the crosslinked particles can take up to 10 minutes to completely dissolve even with some light heating. This same effect has been observed elsewhere (Langmuir, 2008, 24 (19), pp 11169-11174), which is evidence for a cross-linked structure.

To further test the properties of the hollow structures, the overall coulombic charges present at the surface were analyzed with zeta potential measurements. Gold nanoparticle-DNA conjugates are highly negatively charged due to the tight arrangement of negatively charged DNA strands on the surface. The hollow structures should maintain this property if the crosslinking is effective. Three samples were analyzed: DNA-nanoparticle conjugates, dissolved DNA-nanoparticle conjugates that had not been cross-linked, and dissolved DNA-nanoparticles that have been crosslinked—hollow structures. As expected, the dissolved particles exhibited zeta potential measurements that were nearly identical to and within error of the measurements for pure gold nanoparticle-DNA conjugates as represented in Table 4, below.

TABLE 4

| Zeta Potential Measurements | | |
| --- | --- | --- |
| AuNP-DNA | Non Crosslinked Dissolved | Crosslinked Dissolved |
| −38 ± 3 mV | −5 ± 3 mV | −36 ± 4 mV |

Finally, the structural properties of the hollow structures were tested by gel-electrophoresis. In electrophoretic analysis, one can gather information concerning both the size and charge of a molecule or nanoconjugate. Using a 2% agarose gel with ethidium bromide stain at 120V, the movement of DNA from dissolved uncrosslinked and crosslinked (hollow) particles was compared. The DNA from the crosslinked structures moved faster than the free strands liberated from the uncrosslinked particles. This can be explained by the fact that supercoiled DNA, which can be in a spherical shape like a hollow particle, travels faster than free strand DNA of a smaller size through a gel.

In an additional approach, polynucleotides are synthesized bearing two distinct polynucleotide nanoconjugates. The first is a nucleotide sequence specific to a target. The other region is a spacer region harboring a number of pendent alkylamines. These amines are used as synthetic handles to crosslink the polynucleotides with an amine reactive homobifunctional linker, as shown in Scheme 2 (below). Alternatively, these amines can be converted to azides and alkynes via NHS esters bearing those groups. In that case, "click" chemistry can be used to crosslink the polynucleotides. An additional approach to synthesizing a dense polynucleotide nanoconjugate without gold nanoparticles is to conjugate polynucleotides to the surface of an poly(amidoamine) (PAMAM) dendrimer. Polynucleotides functionalized with a terminal decanoic acid moiety are activated with EDC and NHS, and are mixed with PAMAM dendrimers. Alternatively, PAMAM dendrimers terminated in carboxylate groups are activated with EDC and NHS, and reacted with amine-terminated polynucleotides.

Scheme 2. Potential route to polynucleotide nanoconjugates with amine containing polynucleotides and a homobifunctional crosslinker.

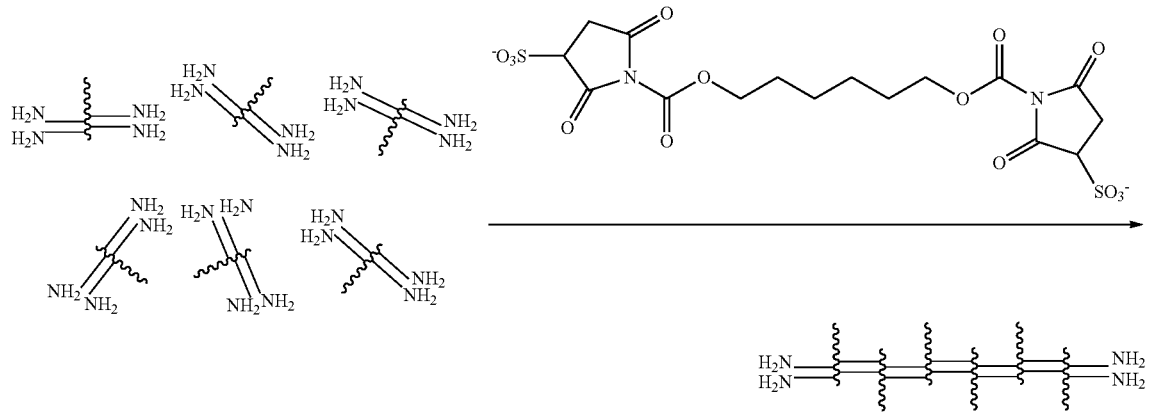

The polynucleotide nanoconjugate is characterized with gel electrophoresis to measure its mass and polydispersity. Next, the cooperative properties of the polynucleotide nanoconjugate are investigated with melting experiments, enzymatic assays, and cellular studies. In the melting studies, two kinds of polynucleotide nanoconjugate are synthesized with complementary sequences. After annealing, the polynucleotide nanoconjugate is melted and the melting temperature profile is compared to that of the same free polynucleotide sequences. The polynucleotide nanoconjugates have sharp and elevated melting transitions versus free polynucleotides. The cooperative properties of the polynucleotide nanoconjugates are investigated with nuclease assays. In these experiments, the rate of strand degradation is measured and compared for nanoconjugate and free polynucleotides.

All templated systems designed in this manner resist enzymatic degradation when compared to free polynucleotides. Cellular uptake studies are performed to examine enhancement of endocytosis for these structures. In addition, gene knockdown studies are performed to measure the ability of the structures to regulate protein expression.

The present example provides additional methods to, in one aspect, obtain hollow and core-less polynucleotide nanoconjugates through the use of templated assembly on a nanoparticle surface, crosslinking, and homobifunctional crosslinkers. These matters are useful in gene regulation methods directed to intracellular targets through the use of both DNA and siRNA strategies.

What is claimed is:

1. A composition comprising a nanoconjugate, the nanoconjugate having a defined structure and comprising a plurality of polynucleotides crosslinked to each other in a monolayer, said structure defined by a surface providing a template upon which the structure is assembled.

2. The composition of claim 1 wherein the surface is a nanoparticle.

3. The composition of claim 1 wherein each polynucleotide in the plurality of polynucleotides is the same.

4. The composition of claim 1 wherein the composition comprises a plurality of nanoconjugates, and the plurality of polynucleotides is monodisperse.

5. The composition of claim 4 wherein the monodispersity is such that there is about 25% variation in the diameter of the plurality of nanoconjugates.

6. The composition of claim 1 wherein the nanoconjugate further comprises an additional agent selected from the group consisting of a polynucleotide, peptide, polypeptide, phospholipid, oligosaccharide, metal complex, small molecule, therapeutic agent, contrast agent and combinations thereof.

7. The composition of claim 6 wherein the additional agent is associated with at least one polynucleotide of the plurality of polynucleotides.

8. The composition of claim 7 wherein the additional agent is associated with at least one biomolecule polynucleotide of the plurality of polynucleotides through hybridization, or the additional agent is covalently associated with at least one biomolecule of the plurality of biomolecules, or the additional agent is entrapped in the crosslinked biomolecules of the nanoconjugate.

9. A method of crosslinking a structured nanoconjugate, the method comprising the step of activating a first biomolecule which is a polynucleotide by contacting the first biomolecule with a surface, the activation allowing the first biomolecule to crosslink to a second biomolecule.

10. The method of claim 9 wherein the surface provides a template upon which the structure is assembled.

11. The method of claim 9 wherein the surface is a nanoparticle.

12. The method of claim 9 wherein the surface is at least partially removed after the crosslinking.

13. The method of claim 9 wherein the second biomolecule is selected from the group consisting of a polynucleotide, peptide, polypeptide, phospholipid, oligosaccharide, small molecule, therapeutic agent, contrast agent and combinations thereof.

14. The method of claim 9 wherein the first biomolecule and the second biomolecule each comprise at least one alkyne moiety, or wherein the first biomolecule and the second biomolecule each comprise about 10 alkyne moieties.

15. The method of claim 14 wherein the alkyne moiety is activated upon contact with the surface.

16. The method of claim 15 wherein the activation renders the alkyne susceptible to a nucleophile.

17. The method of claim 15 wherein activation causes crosslinking of the first biomolecule to the second biomolecule.

18. The method of claim 9 wherein the first biomolecule and the second biomolecule are a a DNA polynucleotide or a RNA polynucleotide.

19. The method of claim 9 wherein an additional agent is added to the first biomolecule and the second biomolecule during the activating step, or wherein an additional agent is added to the nanoconjugate after formation of the nanoconjugate but before the at least partial removal of the surface or wherein an additional agent is added to the nanoconjugate after formation of the nanoconjugate and after the at least partial removal of the surface.

20. A composition comprising a polyvalent nanoconjugate comprising a surface, the nanoconjugate further comprising a plurality of polynucleotides wherein a spacer end of each of the polynucleotides in the plurality is modified such that contacting the plurality of polynucleotides with a chemical crosslinks the plurality of polynucleotides to each other.

21. The composition of claim 20 wherein the modification is selected from the group consisting of an amine, amide, alcohol, ester, aldehyde, ketone, thiol, disulfide, carboxylic acid, phenol, imidazole, hydrazine, hydrazone, azide and an alkyne.

22. The composition of claim 20 wherein the surface comprises a nanoparticle.

23. A method of detecting a target molecule comprising contacting the target molecule with the composition of claim 1, wherein contact between the target molecule and the composition results in a detectable change.

24. The method of claim 23 wherein the detecting is in vitro.

25. A method of inhibiting expression of a gene product encoded by a target polynucleotide comprising contacting the target polynucleotide with a composition of claim 1 under conditions sufficient to inhibit expression of the gene product.

26. The method of claim 25 wherein expression of the gene product is inhibited in vivo.

27. The composition of claim 4 wherein the monodispersity is such that there is about 10% variation in the diameter of the plurality of nanoconjugates.

28. The composition of claim 4 wherein the monodispersity is such that there is about 1% variation in the diameter of the plurality of nanoconjugates.

29. The composition of claim 1, wherein the surface is at least partially removed after the structure has been defined.

30. The composition of claim 29 wherein the surface is a nanoparticle.

31. The composition of claim 29 wherein each polynucleotide in the plurality of polynucleotides is the same.

32. The composition of claim 29 wherein the nanoconjugate further comprises an additional agent selected from the group consisting of a polynucleotide, peptide, polypeptide, phospholipid, oligosaccharide, metal complex, small molecule, therapeutic agent, contrast agent and combinations thereof.

33. The composition of claim 29 wherein the additional agent is associated with at least one polynucleotide of the plurality of polynucleotides.

34. The composition of claim 29 wherein the nanoconjugate is hollow in the absence of the surface.

35. The composition of claim 34 wherein an additional agent is encapsulated in the nanoconjugate which is otherwise hollow.

36. The composition of claim 20 wherein the surface is at least partially removed after the crosslinking.

37. The composition of claim 36 wherein the modification is selected from the group consisting of an amine, amide, alcohol, ester, aldehyde, ketone, thiol, disulfide, carboxylic acid, phenol, imidazole, hydrazine, hydrazone, azide and an alkyne.

38. The method of claim 23 wherein the detecting is in vivo.

39. The method of claim 25 wherein expression of the gene product is inhibited in vitro.

40. The composition of claim 1 wherein the polynucleotide is selected from the group consisting of DNA and RNA.

41. The composition of claim 40 wherein the DNA is double stranded.

42. The composition of claim 40 wherein the RNA is small interfering RNA (siRNA).

43. The composition of claim 20 wherein the polynucleotide is selected from the group consisting of DNA and RNA.

44. The composition of claim 43 wherein the DNA is double stranded.

45. The composition of claim 43 wherein the RNA is small interfering RNA (siRNA).

\* \* \* \* \*

UNITED STATES PATENT AND TRADEMARK OFFICE
CERTIFICATE OF CORRECTION

PATENT NO. : 9,376,690 B2
APPLICATION NO. : 13/504842
DATED : June 28, 2016
INVENTOR(S) : Chad A. Mirkin et al.

Page 1 of 1

It is certified that error appears in the above-identified patent and that said Letters Patent is hereby corrected as shown below:

In the Specification

At Column 1, Line 17:
"This invention was made with government support under Grant Number W911NF-09-0069, awarded by the U.S. Army RDECOM, and Grant Number U54 CA119341, awarded by the National Institutes of Health (NCI-CCNE). The government has certain rights in the invention."

Should be:
"This invention was made with government support under U54 CA119341 awarded by the National Institutes of Health, and W911NF-09-1-0069 awarded by the Army Research Laboratory - Army Research Office. The government has certain rights in the invention.".

In the Claims

At Column 97, Line 35:
"one biomolecule"

Should be:
"one".

Signed and Sealed this
Seventh Day of January, 2025

Derrick Brent
*Acting Director of the United States Patent and Trademark Office*

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (15)..(15)
<223> OTHER INFORMATION: alkyne modified
<220> FEATURE:
<221> NAME/KEY: modified_base
<222> LOCATION: (16)..(16)
<223> OTHER INFORMATION: alkyne modified
<220> FEATURE:
<221> NAME/KEY: modified_base
<222> LOCATION: (17)..(17)
<223> OTHER INFORMATION: alkyne modified
<220> FEATURE:
<221> NAME/KEY: modified_base
<222> LOCATION: (18)..(18)
<223> OTHER INFORMATION: alkyne modified
<220> FEATURE:
<221> NAME/KEY: modified_base
<222> LOCATION: (19)..(19)
<223> OTHER INFORMATION: alkyne modified
<220> FEATURE:
<221> NAME/KEY: modified_base
<222> LOCATION: (20)..(20)
<223> OTHER INFORMATION: alkyne modified
<220> FEATURE:
```

```
<221> NAME/KEY: modified_base
<222> LOCATION: (21)..(21)
<223> OTHER INFORMATION: alkyne modified
<220> FEATURE:
<221> NAME/KEY: modified_base
<222> LOCATION: (22)..(22)
<223> OTHER INFORMATION: alkyne modified
<220> FEATURE:
<221> NAME/KEY: modified_base
<222> LOCATION: (23)..(23)
<223> OTHER INFORMATION: alkyne modified
<220> FEATURE:
<221> NAME/KEY: modified_base
<222> LOCATION: (24)..(24)
<223> OTHER INFORMATION: alkyne modified
<220> FEATURE:
<221> NAME/KEY: misc_feature
<222> LOCATION: (24)..(24)
<223> OTHER INFORMATION: Thiol

<400> SEQUENCE: 1
tcactattat tttttttttt tttt                                              24

<210> SEQ ID NO 2
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (15)..(15)
<223> OTHER INFORMATION: alkyne modified
<220> FEATURE:
<221> NAME/KEY: modified_base
<222> LOCATION: (16)..(16)
<223> OTHER INFORMATION: alkyne modified
<220> FEATURE:
<221> NAME/KEY: modified_base
<222> LOCATION: (17)..(17)
<223> OTHER INFORMATION: alkyne modified
<220> FEATURE:
<221> NAME/KEY: modified_base
<222> LOCATION: (18)..(18)
<223> OTHER INFORMATION: alkyne modified
<220> FEATURE:
<221> NAME/KEY: modified_base
<222> LOCATION: (19)..(19)
<223> OTHER INFORMATION: alkyne modified
<220> FEATURE:
<221> NAME/KEY: modified_base
<222> LOCATION: (20)..(20)
<223> OTHER INFORMATION: alkyne modified
<220> FEATURE:
<221> NAME/KEY: modified_base
<222> LOCATION: (21)..(21)
<223> OTHER INFORMATION: alkyne modified
<220> FEATURE:
<221> NAME/KEY: modified_base
<222> LOCATION: (22)..(22)
<223> OTHER INFORMATION: alkyne modified
<220> FEATURE:
<221> NAME/KEY: modified_base
<222> LOCATION: (23)..(23)
<223> OTHER INFORMATION: alkyne modified
<220> FEATURE:
<221> NAME/KEY: modified_base
<222> LOCATION: (24)..(24)
<223> OTHER INFORMATION: alkyne modified
<220> FEATURE:
<221> NAME/KEY: misc_feature
<222> LOCATION: (24)..(24)
<223> OTHER INFORMATION: Thiol
```

```
<400> SEQUENCE: 2
taatagtgat ttttttttt tttt                                              24
```